US012600731B2

(12) United States Patent
Cheng et al.

(10) Patent No.: US 12,600,731 B2
(45) Date of Patent: Apr. 14, 2026

(54) ISOXAZOLO[5,4-H]QUINAZOLINE COMPOUNDS AS PROTEIN KINASE INHIBITORS

(71) Applicant: CHENGDU CYNOGEN BIO-PHARMACEUTICAL TECHNOLOGY CO., LTD., Chengdu (CN)

(72) Inventors: Hang Cheng, Chengdu (CN); Weiyan Xiong, Chengdu (CN); Bin Yu, Chengdu (CN); Wei Niu, Chengdu (CN)

(73) Assignee: Chengdu Cynogen Bio-Pharmaceutical Technology Co., Ltd., Chengdu (CN)

(*) Notice: Subject to any disclaimer, the term of this patent is extended or adjusted under 35 U.S.C. 154(b) by 994 days.

(21) Appl. No.: 17/640,115

(22) PCT Filed: Sep. 3, 2020

(86) PCT No.: PCT/CN2020/113139
§ 371 (c)(1),
(2) Date: Mar. 3, 2022

(87) PCT Pub. No.: WO2021/043190
PCT Pub. Date: Mar. 11, 2021

(65) Prior Publication Data

US 2022/0363690 A1 Nov. 17, 2022

(30) Foreign Application Priority Data

Sep. 5, 2019 (CN) ......................... 201910835769.8

(51) Int. Cl.
*C07D 498/04* (2006.01)
*A61P 35/00* (2006.01)

(52) U.S. Cl.
CPC ............ *C07D 498/04* (2013.01); *A61P 35/00* (2018.01)

(58) Field of Classification Search
CPC .............................. A61P 35/00; C07D 498/04
See application file for complete search history.

(56) References Cited

U.S. PATENT DOCUMENTS

2022/0315584 A1* 10/2022 Cheng .................. C07D 487/14

FOREIGN PATENT DOCUMENTS

| | | | |
|---|---|---|---|
| WO | 2004104007 | A1 | 12/2004 |
| WO | 2005037843 | A1 | 4/2005 |
| WO | 2018177403 | A1 | 10/2018 |
| WO | 2019029663 | A1 | 2/2019 |

OTHER PUBLICATIONS

Dudkin, V. Y. "Bioisosteric equivalence of five-membered heterocycles." Chemistry of Heterocyclic Compounds 48 (2012): 27-32. ( Year: 2012).*

Braga, Dario, Simone d'Agostino, Elena Dichiarante, Lucia Maini, and Fabrizia Grepioni. "Dealing with crystal forms (the kingdom of serendip?)." Chemistry—An Asian Journal 6, No. 9 (2011): 2214-2223 (Year: 2011).*

Ettmayer, Peter, Gordon L. Amidon, Bernd Clement, and Bernard Testa. "Lessons learned from marketed and investigational prodrugs." Journal of medicinal chemistry 47, No. 10 (2004): 2393-2404 (Year: 2004).*

Hanahan, Douglas, and Robert A. Weinberg. "The Hallmarks of Cancer." Cell 100, No. 1 (2000): 57-70 (Year: 2000).*

Wang, Qiushi, Ann M. Bode, and Tianshun Zhang. "Targeting CDK1 in cancer: mechanisms and implications." NPJ precision oncology 7, No. 1 (2023): 58. (Year: 2023).*

Huang, Xiaoling, Shidi Xu, Lei Duan, Shan Xu, and Wufu Zhu. "A patent review of small molecule CDK4/6 inhibitors in the treatment of cancer: 2020 to the present." Expert Opinion on Therapeutic Patents 34, No. 9 (2024): 825-842. (Year: 2024).*

(Continued)

*Primary Examiner* — James H Alstrum-Acevedo
*Assistant Examiner* — Carolyn L. Ladd
(74) *Attorney, Agent, or Firm* — Lowenstein Sandler LLP

(57) ABSTRACT

The present disclosure provides a class of isoxazolo[5,4-H] quinazoline compounds represented by general formula (I), which can be used to treat cell proliferation disorders, and are effective cyclin-dependent kinase (CDK) inhibitors, which have a broad-spectrum and strong inhibitory activity against CDK. The present disclosure also provides a pharmaceutical composition comprising the compound, and a method of treating and/or preventing a CDK-mediated disease in a subject, including administering the compound or the composition of the present disclosure.

(I)

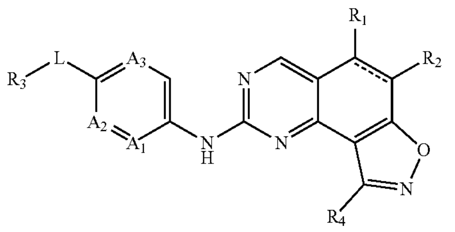

23 Claims, No Drawings

(56) References Cited

OTHER PUBLICATIONS

T. Higuchi and V. Stella, Prodrugs as Novel Delivery Systems, A.C.S. Symposium Series, vol. 14, 6 pages.
D. Fleisher, S. Ramon and H. Barbra "Improved oral drug delivery: solubility limitations overcome by the use of prodrugs", Advanced Drug Delivery Reviews (1996) 19(2) 115-130.
International Search Report for PCT/CN2020/113139 mailed Dec. 7, 2020, 8 pages.

* cited by examiner

ISOXAZOLO[5,4-H]QUINAZOLINE COMPOUNDS AS PROTEIN KINASE INHIBITORS

CROSS-REFERENCE TO RELATED APPLICATION(S)

The present application is a national stage entry under 35 U.S.C. § 371 of International Application No. PCT/CN2020/113139, filed on Sep. 3, 2020, which claims priority to Chinese Patent Application No. 201910835769.8, filed on Sep. 5, 2019. The contents of these applications are hereby incorporated by reference in their entirety.

FIELD OF THE INVENTION

The present disclosure provides a class of isoxazolo[5,4-H]quinazoline compounds as inhibitors of cyclin-dependent kinase (CDK), which have a broad-spectrum and strong inhibitory activity against CDK. The compounds of the present disclosure are effective in treating diseases such as cancer, inflammation, etc.

BACKGROUND OF THE INVENTION

Cyclin-dependent kinase (CDK) and cyclin are important factors in cell cycle regulation. CDK can combine with cyclin to form a heterodimer, in which CDK is the catalytic subunit and cyclin is the regulatory subunit. Various cyclin-CDK complexes thus formed phosphorylate different substrates, and promote and transform different phases of the cell cycle.

In the past decade, CDK inhibitors have become a hot topic in the development of new anti-tumor drugs, and more than 20 CDK inhibitors have entered the clinical stage. Although the preclinical pharmacodynamic results of CDK inhibitors are remarkable, the results of most clinical trials are not satisfactory. Problems include lack of efficacy in solid tumors and greater toxicity. Some CDK inhibitor drugs lack selectivity for CDK subtypes, resulting in greater toxicity.

CDK4 and CDK6 are two closely related kinases that bind to Cyclin D during the tumor cell cycle to promote cell cycle progress from G1 phase to S phase and are required for cell cycle progression. It has been shown that in human tumors (such as breast cancer and myeloma), activation of CDK4 and CDK6 leads to cell cycle changes. Inhibition of CDK4 and CDK6 prevents the inactivation of the tumor suppressor protein Rb and interferes with tumor cell cycle progression.

Currently, there are multiple selective CDK4/6 inhibitors in clinical stage (e.g. Palbociclib, Dinaciclib, LY2835219 and LEE011). The clinical evaluation of these drugs also includes metastatic breast cancer, ovarian cancer, liposarcoma, non-small cell lung cancer, liver cancer, glioblastoma, melanoma, multiple myeloma and lymphoma, etc.

Although many CDK inhibitor compounds have been published, there is still a need for more CDK inhibitors (especially CDK4/6 selective inhibitors) to treat CDK-related diseases.

SUMMARY OF THE INVENTION

The present disclosure provides a class of isoxazolo[5,4-H]quinazoline compounds as inhibitors of cyclin-dependent kinase, which have a strong inhibitory activity. Compared with the existing drugs, the compounds of the present disclosure can further improve the pharmacokinetic properties, including the significant improvement in the metabolic stability and clearance rate over the existing compounds.

In one aspect, the present disclosure provides a compound of formula (I), or a pharmaceutically acceptable salt, an enantiomer, a diastereomer, a racemate, a solvate, a hydrate, a polymorph, a prodrug, or an isotope variant thereof, and mixtures thereof:

(I)

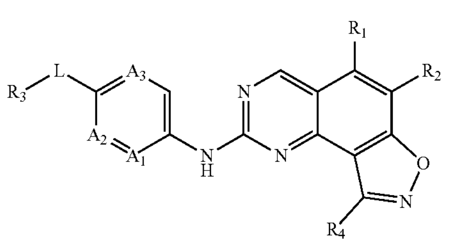

wherein:

$\overline{\overline{\ \ }}$ indicates a single bond or a double bond;

$A_1$ is selected from $CR_5$ or N;

$A_2$ is selected from $CR_6$ or N;

$A_3$ is selected from $CR_7$ or N;

$R_1$ is selected from H, D, halogen, —CN, —$OR_a$, —$SR_a$, —$NR_bR_c$, —C(O)$R_a$, —C(O)O$R_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl; wherein the said $C_{3-7}$ cycloalkyl or 3- to 7-membered heterocyclyl is optionally substituted by oxo or thioxo;

$R_2$ is selected from H, D, halogen, —CN, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl; wherein the said $C_{3-7}$ cycloalkyl or 3- to 7-membered heterocyclyl is optionally substituted by oxo or thioxo;

$R_3$ is selected from H, D, halogen, —CN, —$NO_2$, —$OR_a$, —$SR_a$, —$NR_bR_c$, —C(O)$R_a$, —C(O)O$R_a$, —C(O)$NR_bR_c$, —$S(O)_mR_a$, —$S(O)_mOR_a$, —$S(O)_mNR_bR_c$, —O—$C_{1-6}$ alkylene-$R_8$, $C_{1-6}$ alkyl, $C_{1-6}$ haloalkyl, $C_{3-7}$ cycloalkyl, 3- to 11-membered heterocyclyl, $C_{6-10}$ aryl, or 5- to 10-membered heteroaryl, each of which is optionally substituted by 1, 2, 3, 4, or 5 $R_8$ groups;

$R_4$ is selected from H, —C(O)$R_a$, —C(O)O$R_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl;

L is selected from a chemical bond, —O—, —NH—, —C(O)—, —C(O)NH—, —NHC(O)—, —$C_{1-6}$ alkylene-, —$C_{2-6}$ alkenylene- or —$C_{2-6}$ alkynylene-;

and wherein, $R_5$ is selected from H, D, halogen, —CN, —$OR_a$, —$SR_a$, —$NR_bR_c$, —C(O)$R_a$, —C(O)O$R_a$, —C(O)$NR_bR_c$, —$S(O)_mR_a$, —$S(O)_mOR_a$, —$S(O)_mNR_bR_c$, $C_{1-6}$ alkyl or $C_{1-6}$ haloalkyl;

$R_6$ is selected from H, D, halogen, —CN, —$OR_a$, —$SR_a$, —$NR_bR_c$, —C(O)$R_a$, —C(O)O$R_a$, —C(O)$NR_bR_c$, —$S(O)_mR_a$, —$S(O)_mOR_a$, —$S(O)_mNR_bR_c$, $C_{1-6}$ alkyl or $C_{1-6}$ haloalkyl;

$R_7$ is selected from H, D, halogen, —CN, —$OR_a$, —$SR_a$, —$NR_bR_c$, —C(O)$R_a$, —C(O)O$R_a$, —C(O)$NR_bR_c$, —$S(O)_mR_a$, —$S(O)_mOR_a$, —$S(O)_mNR_bR_c$, $C_{1-6}$ alkyl or $C_{1-6}$ haloalkyl;

$R_8$ is selected from H, D, —$NH_2$, —$NHC_{1-6}$ alkyl, —N($C_{1-6}$ alkyl$)_2$, $C_{1-6}$ alkyl, $C_{1-6}$ haloalkyl, —$C_{0-6}$ alkylene-$OR_a$, $C_{3-7}$ cycloalkyl, 3- to 7-membered heterocyclyl, $C_{6-10}$ aryl, or 5- to 10-membered heteroaryl; or two $R_8$ on the same atom are taken together to form oxo or thioxo;

$R_a$ is independently selected from H, —$C_{0-6}$ alkylene-CN, —$C_{0-6}$ alkylene-$NO_2$, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C(O)OR', —$C_{0-6}$ alkylene-C(O)NR"R'", —$C_{0-6}$ alkylene-$S(O)_m$R', —$C_{0-6}$ alkylene-$S(O)_m$OR', —$C_{0-6}$ alkylene-$S(O)_m$NR"R'", $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl;

$R_b$ and $R_c$ are independently selected from H, —$C_{0-6}$ alkylene-CN, —$C_{0-6}$ alkylene-$NO_2$, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C(O)OR', —$C_{0-6}$ alkylene-C(O)NR"R'", —$C_{0-6}$ alkylene-$S(O)_m$R', —$C_{0-6}$ alkylene-$S(O)_m$OR', —$C_{0-6}$ alkylene-$S(O)_m$NR"R'", $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or, $R_b$, $R_c$ and N atom are taken together to form 3- to 7-membered heterocyclyl;

R' is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl;

R" and R'" are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl; or, R", R'" and N atom are taken together to form 3- to 7-membered heterocyclyl;

m represents 0, 1, or 2;

and, $R_1$-$R_2$ and $R_4$-$R_8$ are optionally substituted with 1, 2 or 3 R groups, wherein the R is independently selected from H, —OH, halogen, —$NO_2$, carbonyl, —CN, —$OR_a$, —$SR_a$, —$NR_bR_c$, —C(O)$R_a$, —C(S)$R_a$, —C(O)$OR_a$, —C(S)$OR_a$, —C(O)—$NR_bR_c$, —C(S)—$NR_bR_c$, —O—C(O)$R_a$, —O—C(S)$R_a$, —N($R_b$)—C(O)—$R_a$, —N($R_b$)—C(S)—$R_a$, —$S(O)_mR_a$, —$S(O)_mOR_a$, —$S(O)_mNR_bR_c$, —N($R_b$)—$S(O)_m$—$R_a$, —N($R_b$)—$S(O)_m$—$NR_bR_c$, —N($R_b$)—C(O)$OR_a$, —N($R_b$)—C(S)$OR_a$, —O—$C_{1-6}$ alkylene-$OR_a$, —C(O)—$C_{1-6}$ alkylene-$NR_bR_c$, —N($R_b$)—C(O)—$NR_bR_c$, —N($R_b$)—C(S)—$NR_bR_c$, —O—C(O)—$NR_bR_c$, —O—C(S)—$NR_bR_c$, $C_{1-6}$ alkyl, $C_{1-6}$ haloalkyl, $C_{2-6}$ alkenyl, $C_{2-6}$ alkynyl, $C_{3-7}$ cycloalkyl, 3- to 7-membered heterocyclyl, $C_{6-10}$ aryl, or 5- to 10-membered heteroaryl; wherein the said $C_{1-6}$ alkyl, $C_{1-6}$ haloalkyl, $C_{2-6}$ alkenyl, $C_{2-6}$ alkynyl, $C_{3-7}$ cycloalkyl, 3- to 7-membered heterocyclyl, $C_{6-10}$ aryl or 5- to 10-membered heteroaryl is each further optionally substituted by one or more groups consisting of the following:

—CN, —$NO_2$, carbonyl, —$OR_a$, —$SR_a$, —$NR_bR_c$, —C(O)$R_a$, —C(S)$R_a$, —C(O)$OR_a$, —C(S)$OR_a$, —C(O)—$NR_bR_c$, —C(S)—$NR_bR_c$, —O—C(O)$R_a$, —O—C(S)$R_a$, —N($R_b$)—C(O)—$R_a$, —N($R_b$)—C(S)—$R_a$, —$S(O)_mR_a$, —$S(O)_mOR_a$, —$S(O)_mNR_bR_c$, —N($R_b$)—$S(O)_m$—$R_a$, —N($R_b$)—$S(O)_m$—$R_bR_c$, —N($R_b$)—C(O)$OR_a$, —N($R_b$)—C(S)$OR_a$, —O—$C_{1-6}$ alkylene-$OR_a$, —C(O)—$C_{1-6}$ alkylene-$NR_bR_c$, —N($R_b$)—C(O)—$NR_bR_c$, —N($R_b$)—C(S)—$NR_bR_c$, —O—C(O)—$NR_bR_c$ or —O—C(S)—$NR_bR_c$;

$R_a$, $R_b$ and $R_c$ are each further optionally substituted by one or more groups consisting of the following:

$C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl.

In another aspect, the present disclosure provides a compound of formula (I), or a pharmaceutically acceptable salt, an enantiomer, a diastereomer, a racemate, a solvate, a hydrate, a polymorph, a prodrug, or an isotope variant thereof, and mixtures thereof:

(I)

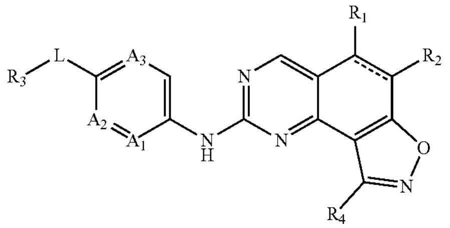

wherein:

⎓ indicates a single bond or a double bond;

$A_1$ is selected from $CR_5$ or N;

$A_2$ is selected from $CR_6$ or N;

$A_3$ is selected from $CR_7$ or N;

$R_1$ is selected from H, halogen, —CN, —$OR_a$, —$SR_a$, —$NR_bR_c$, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl; wherein the said $C_{3-7}$ cycloalkyl or 3- to 7-membered heterocyclyl is optionally substituted by oxo or thioxo;

$R_2$ is selected from H, halogen, —CN, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl; wherein the said $C_{3-7}$ cycloalkyl or 3- to 7-membered heterocyclyl is optionally substituted by oxo or thioxo;

$R_3$ is selected from H, halogen, —CN, —$NO_2$, —$OR_a$, —$SR_a$, —$NR_bR_c$, —C(O)$R_a$, —C(O)$OR_a$, —C(O)$NR_bR_c$, —$S(O)_mR_a$, —$S(O)_mOR_a$, —$S(O)_mNR_bR_c$, —O—$C_{1-6}$ alkylene-$R_8$, $C_{1-6}$ alkyl, $C_{1-6}$ haloalkyl, $C_{3-7}$ cycloalkyl, 3- to 11-membered heterocyclyl, $C_{6-10}$ aryl, or 5- to 10-membered heteroaryl, each of which is optionally substituted by 1, 2, 3, 4, or 5 $R_8$ groups;

$R_4$ is selected from H, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl;

L is selected from a chemical bond, —O—, —NH—, —C(O)—, —C(O)NH—, —NHC(O)—, —$C_{1-6}$ alkylene-, —$C_{2-6}$ alkenylene- or —$C_{2-6}$ alkynylene-;

and wherein, $R_5$ is selected from H, halogen, —CN, —$OR_a$, —$SR_a$, —$NR_bR_c$, —C(O)$R_a$, —C(O)$OR_a$, —C(O)$NR_bR_c$, $C_{1-6}$ alkyl or $C_{1-6}$ haloalkyl;

$R_6$ is selected from H, halogen, —CN, —$OR_a$, —$SR_a$, —$NR_bR_c$, —C(O)$R_a$, —C(O)$OR_a$, —C(O)$NR_bR_c$, $C_{1-6}$ alkyl or $C_{1-6}$ haloalkyl;

$R_7$ is selected from H, halogen, —CN, —$OR_a$, —$SR_a$, —$NR_bR_c$, —C(O)$R_a$, —C(O)$OR_a$, —C(O)$NR_bR_c$, $C_{1-6}$ alkyl or $C_{1-6}$ haloalkyl;

$R_8$ is selected from H, —$NH_2$, —$NHC_{1-6}$ alkyl, —N($C_{1-6}$ alkyl)$_2$, $C_{1-6}$ alkyl, $C_{1-6}$ haloalkyl, —$C_{0-6}$ alkylene-$OR_a$, $C_{3-7}$ cycloalkyl, 3- to 7-membered heterocyclyl, $C_{6-10}$ aryl, or 5- to 10-membered heteroaryl; or two $R_8$ on the same atom are taken together to form oxo or thioxo;

$R_a$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl;

$R_b$ and $R_c$ are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl; or, $R_b$, $R_c$ and N atom are taken together to form 3- to 7-membered heterocyclyl;

m represents 0, 1, or 2;

and, $R_1$-$R_2$ and $R_4$-$R_8$ are optionally substituted with 1, 2 or 3 R groups, wherein the R is independently selected from H, —OH, halogen, —$NO_2$, carbonyl, —CN, —$OR_a$, —$SR_a$, —$NR_bR_c$, —C(O)$R_a$, —C(S)$R_a$, —C(O)$OR_a$, —C(S)$OR_a$, —C(O)—$NR_bR_c$, —C(S)—$NR_bR_c$, —O—C(O)$R_a$, —O—C(S)$R_a$, —N($R_b$)—C(O)—$R_a$, —N($R_b$)—C(S)—$R_a$, —$S(O)_mR_a$, —$S(O)_mOR_a$, —$S(O)_mNR_bR_c$, —N($R_b$)—$S(O)_m$—$R_a$, —N($R_b$)—S$(O)_m$—$NR_bR_c$, —N($R_b$)—C(O)$OR_a$, —N($R_b$)—C(S)$OR_a$, —O—$C_{1-6}$ alkylene-$OR_a$, —C(O)—$C_{1-6}$ alkylene-$NR_bR_c$, —N($R_b$)—C(O)—$NR_bR_c$, —N($R_b$)—C(S)—$NR_bR_c$, —O—C(O)—$NR_bR_c$, —O—C(S)—$NR_bR_c$, $C_{1-6}$ alkyl, $C_{1-6}$ haloalkyl, $C_{2-6}$ alkenyl, $C_{2-6}$ alkynyl, $C_{3-7}$ cycloalkyl, 3- to 7-membered heterocyclyl, $C_{6-10}$ aryl, or 5- to 10-membered heteroaryl; wherein the said $C_{1-6}$ alkyl, $C_{1-6}$ haloalkyl, $C_{2-6}$ alkenyl, $C_{2-6}$ alkynyl, $C_{3-7}$ cycloalkyl, 3- to 7-membered heterocyclyl, $C_{6-10}$ aryl or 5- to 10-membered heteroaryl is each further optionally substituted by one or more groups consisting of the following:

—CN, —$NO_2$, carbonyl, —$OR_a$, —$SR_a$, —$NR_bR_c$, —C(O)$R_a$, —C(S)$R_a$, —C(O)$OR_a$, —C(S)$OR_a$, —C(O)—$NR_bR_c$, —C(S)—$NR_bR_c$, —O—C(O)$R_a$, —O—C(S)$R_a$, —N($R_b$)—C(O)—$R_a$, —N($R_b$)—C(S)—$R_a$, —$S(O)_mR_a$, —$S(O)_mOR_a$, —$S(O)_mNR_bR_c$, —N($R_b$)—$S(O)_m$—$R_a$, —N($R_b$)—$S(O)_m$—$R_bR_c$, —N($R_b$)—C(O)$OR_a$, —N($R_b$)—C(S)$OR_a$, —O—$C_{1-6}$ alkylene-$OR_a$, —C(O)—$C_{1-6}$ alkylene-$NR_bR_c$, —N($R_b$)—C(O)—$NR_bR_c$, —N($R_b$)—C(S)—$NR_bR_c$, —O—C(O)—$NR_bR_c$ or —O—C(S)—$NR_bR_c$;

$R_a$, $R_b$ and $R_c$ are each further optionally substituted by one or more groups consisting of the following:

$C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl.

In another aspect, the present disclosure provides a pharmaceutical composition comprising a compound of the present disclosure, and optionally pharmaceutically acceptable excipient(s).

In another aspect, the present disclosure provides a pharmaceutical composition comprising a compound of the present disclosure and pharmaceutically acceptable excipient(s), which further comprises other therapeutic agent(s).

In another aspect, the present disclosure provides a kit comprising a compound of the present disclosure, other therapeutic agent(s) and pharmaceutically acceptable carrier(s), adjuvant(s) or vehicle(s).

In another aspect, the present disclosure provides use of a compound of the present disclosure in the preparation of a medicament for the treatment and/or prevention of a CDK-mediated disease.

In another aspect, the present disclosure provides a method of treating and/or preventing a CDK-mediated disease in a subject, including administering a compound of the present disclosure or a composition of the present disclosure to the subject.

In another aspect, the present disclosure provides a compound or a composition of the present disclosure, for use in treating and/or preventing a CDK-mediated disease.

In a specific embodiment, the diseases described herein include cell proliferative diseases such as solid tumors such as sarcomas and carcinomas (e.g., fibrosarcoma, myxosarcoma, liposarcoma, chondrosarcoma, osteosarcoma, chordoma, angiosarcoma, endothelial sarcoma, lymphangiosarcoma, lymphangioendothelioma, synovialoma, mesothelioma, ewing's tumor, leiomyosarcoma, rhabdomyosarcoma, colon cancer, pancreatic cancer, breast cancer, ovarian cancer, prostate cancer, squamous cell carcinoma, basal cell carcinoma carcinoma, adenocarcinoma, hidradenoma, sebaceous carcinoma, papillary carcinoma, papillary adenocarcinoma, cystadenocarcinoma, medullary carcinoma, bronchial carcinoma, renal cell carcinoma, liver cancer, cholangiocarcinoma, choriocarcinoma, seminoma, embryonal cancer, embryonal carcinosarcoma, cervical cancer, uterine cancer, testicular cancer, lung cancer, small cell lung cancer, bladder cancer, epithelial cancer, glioma, astrocytoma, medulloblastoma, craniopharyngioma, chamber ependymoma, pineal tumor, hemangioblastoma, acoustic neuroma, oligodendroglioma, schwannoma, meningioma, melanoma, neuroblastoma and retinoblastoma).

Other objects and advantages of the present disclosure will be apparent to those skilled in the art from the subsequent specific embodiments, examples and claims.

Definitions

Chemical Definitions

Definitions of specific functional groups and chemical terms are described in more detail hereafter.

When a range of values is listed, each value and sub-range within the range are intended to be included. For example, "$C_{1-6}$ alkyl" is intended to include $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$ and $C_{5-6}$ alkyl.

It should be understood that when described herein any of the moieties defined forth below may be substituted by a variety of substituents, and that the respective definitions are intended to include such substituted moieties within their scope as set out below. Unless otherwise stated, the term "substituted" is to be defined as set out below.

"$C_{1-6}$ alkyl" refers to a radical of a straight or branched, saturated hydrocarbon group having 1 to 6 carbon atoms. In some embodiments, $C_{1-4}$ alkyl is preferred. Examples of $C_{1-6}$ alkyl include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentyl ($C_5$), pentyl ($C_5$), neopentyl ($C_5$), 3-methyl-2-butyl ($C_5$), tert-pentyl ($C_5$) and n-hexyl ($C_6$). The term "$C_{1-6}$ alkyl" also includes heteroalkyl, wherein one or more (e.g., 1, 2, 3 or 4) carbon atoms are substituted with heteroatoms (e.g., oxygen, sulfur, nitrogen, boron, silicon, phosphorus). Alkyl groups can be optionally substituted with one or more substituents, for example, with 1 to 5 substituents, 1 to 3 substituents or 1 substituent. Conventional abbreviations of alkyl include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$) or i-Bu (—$CH_2CH(CH_3)_2$).

"$C_{2-6}$ alkenyl" refers to a radical of a straight or branched hydrocarbon group having 2 to 6 carbon atoms and at least one carbon-carbon double bond. In some embodiments, $C_{2-4}$ alkenyl is preferred. Examples of $C_{2-6}$ alkenyl include vinyl ($C_2$), 1-propenyl ($C_3$), 2-propenyl ($C_3$), 1-butenyl ($C_4$), 2-butenyl ($C_4$), butadienyl ($C_4$), pentenyl ($C_5$), pentadienyl ($C_5$), hexenyl ($C_6$), etc. The term "$C_{2-6}$ alkenyl" also includes heteroalkenyl, wherein one or more (e.g., 1, 2, 3 or 4) carbon atoms are replaced by heteroatoms (e.g., oxygen, sulfur, nitrogen, boron, silicon, phosphorus). The alkenyl groups can be optionally substituted with one or more substituents, for example, with 1 to 5 substituents, 1 to 3 substituents or 1 substituent.

"$C_{2-6}$ alkynyl" refers to a radical of a straight or branched hydrocarbon group having 2 to 6 carbon atoms, at least one carbon-carbon triple bond and optionally one or more carbon-carbon double bonds. In some embodiments, $C_{2-4}$ alkynyl is preferred. Examples of $C_{2-6}$ alkynyl include, but are not limited to, ethynyl ($C_2$), 1-propynyl ($C_3$), 2-propynyl ($C_3$), 1-butynyl ($C_4$), 2-butynyl ($C_4$), pentynyl ($C_5$), hexynyl ($C_6$), etc. The term "$C_{2-6}$ alkynyl" also includes heteroalkynyl, wherein one or more (e.g., 1, 2, 3 or 4) carbon atoms are replaced by heteroatoms (e.g., oxygen, sulfur, nitrogen, boron, silicon, phosphorus). The alkynyl groups can be substituted with one or more substituents, for example, with 1 to 5 substituents, 1 to 3 substituents or 1 substituent.

"—$C_{1-6}$ alkylene-, —$C_{2-6}$ alkenylene- or —$C_{2-6}$ alkynylene-" refers to a divalent group of the "$C_{1-6}$ alkyl, $C_{2-6}$ alkenyl or $C_{2-6}$ alkynyl" as defined above.

"$C_{1-6}$ alkylene" refers to a divalent group formed by removing another hydrogen of the $C_{1-6}$ alkyl, and can be a substituted or unsubstituted alkylene. In some embodiments, $C_{1-4}$ alkylene is particularly preferred. The unsubstituted alkylene groups include, but are not limited to, methylene ($—CH_2—$), ethylene ($—CH_2CH_2—$), propylene ($—CH_2CH_2CH_2—$), butylene ($—CH_2CH_2CH_2CH_2—$), pentylene ($—CH_2CH_2CH_2CH_2CH_2—$), hexylene ($—CH_2CH_2CH_2CH_2CH_2CH_2—$), etc. Examples of substituted alkylene groups, such as those substituted with one or more alkyl (methyl) groups, include, but are not limited to, substituted methylene ($—CH(CH_3)—$, $—C(CH_3)_2—$), substituted ethylene ($—CH(CH_3)CH_2—$, $—CH_2CH(CH_3)—$, $—C(CH_3)_2CH_2—$, $—CH_2C(CH_3)_2—$), substituted propylene ($—CH(CH_3)CH_2CH_2—$, $—CH_2CH(CH_3)CH_2—$, $—CH_2CH_2CH(CH_3)—$, $—C(CH_3)_2CH_2CH_2—$, $—CH_2C(CH_3)_2CH_2—$, $—CH_2CH_2C(CH_3)_2—$), etc.

"$C_{0-6}$ alkylene" means a chemical bond and "$C_{1-6}$ alkylene" as defined above.

"$C_{2-6}$ alkenylene" refers to a $C_{2-6}$ alkenyl group wherein another hydrogen is removed to provide a divalent radical of alkenylene, and which may be substituted or unsubstituted alkenylene. In some embodiments, $C_{2-4}$ alkenylene is particularly preferred. Exemplary unsubstituted alkenylene groups include, but are not limited to, ethenylene ($—CH{=}CH—$) and propenylene (e.g., $—CH{=}CHCH_2—$, $—CH_2—CH{=}CH—$). Exemplary substituted alkenylene groups, e.g., substituted with one or more alkyl (methyl) groups, include but are not limited to, substituted ethylene ($—C(CH_3){=}CH—$, $—CH{=}C(CH_3)—$), substituted propylene (e.g., $—C(CH_3){=}CHCH_2—$, $—CH{=}C(CH_3)CH_2—$, $—CH{=}CHCH(CH_3)—$, $—CH{=}CHC(CH_3)_2—$, $—CH(CH_3)—CH{=}CH—$, $—C(CH_3)_2—CH{=}CH—$, $—CH_2—C(CH_3){=}CH—$, $—CH_2—CH{=}C(CH_3)—$), and the like.

"$C_{2-6}$ alkynylene" refers to a $C_{2-6}$ alkynyl group wherein another hydrogen is removed to provide a divalent radical of alkynylene, and which may be substituted or unsubstituted alkynylene. In some embodiments, $C_{2-4}$ alkynylene is particularly preferred. Exemplary alkynylene groups include, but are not limited to, ethynylene ($—C{\equiv}C—$), substituted or unsubstituted propynylene ($—C{\equiv}CCH_2—$), and the like.

"Halo" or "halogen" refers to fluorine (F), chlorine ($C_1$), bromine (Br) and iodine (I).

"$C_{1-6}$ haloalkyl" represents the "$C_{1-6}$ alkyl" described above, which is substituted with one or more halogen groups. Examples include the mono-, di-, poly-halogenated, including perhalogenated, alkyl. A monohalogen substituent may have one iodine, bromine, chlorine or fluorine atom in the group; a dihalogen substituent and a polyhalogen substituent may have two or more identical halogen atoms or a combination of different halogens. Examples of preferred haloalkyl groups include monofluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The haloalkyl groups can be substituted at any available point of attachment, for example, with 1 to 5 substituents, 1 to 3 substituents or 1 substituent.

"$C_{3-7}$ cycloalkyl" refers to a radical of non-aromatic cyclic hydrocarbon group having 3 to 7 ring carbon atoms and zero heteroatoms. In some embodiments, $C_{3-6}$ cycloalkyl is particularly preferred, $C_{4-6}$ cycloalkyl is more preferred, and $C_{5-6}$ cycloalkyl is more preferred. The cycloalkyl also includes a ring system in which the cycloalkyl described herein is fused with one or more aryl or heteroaryl groups, wherein the point of attachment is on the cycloalkyl ring, and in such case, the number of carbon atoms continues to represent the number of carbon atoms in the cycloalkyl system. Exemplary cycloalkyl groups include, but are not limited to, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), cycloheptyl ($C_7$), cycloheptenyl ($C_7$), cycloheptadienyl ($C_7$), cycloheptatrienyl ($C_7$), etc.

"3- to 11-membered heterocyclyl" refers to a radical of 3- to 11-membered non-aromatic ring system having ring carbon atoms and 1 to 5 ring heteroatoms, wherein each of the heteroatoms is independently selected from nitrogen, oxygen, sulfur, boron, phosphorus and silicon. In the heterocyclyl containing one or more nitrogen atoms, the point of attachment can be a carbon or nitrogen atom as long as the valence permits. In some embodiments, 3- to 9-membered heterocyclyl is preferred, which is a radical of 3- to 9-membered non-aromatic ring system having ring carbon atoms and 1 to 5 ring heteroatoms. In some embodiments, 3- to 7-membered heterocyclyl is preferred, which is a radical of 3- to 7-membered non-aromatic ring system having ring carbon atoms and 1 to 4 ring heteroatoms. 3- to 6-membered heterocyclyl is preferred, which is a radical of 3- to 6-membered non-aromatic ring system having ring carbon atoms and 1 to 3 ring heteroatoms. 4- to 7-membered heterocyclyl is preferred, which is a radical of 4- to 7-membered non-aromatic ring system having ring carbon atoms and 1 to 3 ring heteroatoms. 4- to 6-membered heterocyclyl is preferred, which is a radical of 4- to 6-membered non-aromatic ring system having ring carbon atoms and 1 to 3 ring heteroatoms. 5- to 6-membered heterocyclyl is more preferred, which is a radical of 5- to 6-membered non-aromatic ring system having ring carbon atoms and 1 to 3 ring heteroatoms. The heterocyclyl also includes a ring system wherein the heterocyclyl described above is fused with one or more cycloalkyl groups, wherein the point of attachment is on the cycloalkyl ring, or the heterocyclyl described above is fused with one or more aryl or heteroaryl groups, wherein the point of attachment is on the heterocyclyl ring; and in such cases, the number of ring members continues to represent the number of ring members in the heterocyclyl ring system. Exemplary 3-membered heterocyclyl groups containing one heteroatom include, but are not limited to, aziridinyl, oxiranyl and thiorenyl. Exemplary 4-membered heterocyclyl groups containing one heteroatom include, but are not limited to, azetidinyl, oxetanyl and thietanyl. Exemplary 5-membered heterocyclyl groups containing one heteroatom include, but are not limited to, tetrahydrofuranyl, dihydrofuranyl, tetrahydrothiophenyl, dihydrothienyl, pyrrolidinyl, dihydropyrrolyl and pyrrolyl-2, 5-dione. Exemplary 5-membered heterocyclyl groups containing two heteroatoms include, but are not limited to, dioxolanyl, oxasulfuranyl, disulfuranyl, and oxazolidin-2-one. Exemplary 5-membered heterocyclyl groups containing three heteroatoms include, but are not limited to, triazolinyl, oxadiazolinyl, and thiadiazolinyl. Exemplary 6-membered heterocyclyl groups containing one heteroatom include, but are not limited to, piperidyl, tetrahydropyranyl, dihydropyridyl and thianyl. Exemplary 6-membered heterocyclyl groups containing two heteroatoms include, but are not limited to, piperazinyl, morpholinyl, dithianyl and dioxanyl. Exemplary 6-membered heterocyclyl groups containing three heteroatoms include, but are not limited to, triazinanyl. Exemplary 7-membered heterocycly groups containing one heteroatom include, but are not limited to, azepanyl, oxepanyl and thiepanyl. Exemplary 5-membered heterocyclyl groups fused with a $C_6$ aryl (also referred as 5,6-bicyclic heterocyclyl herein) include, but are not limited to, indolinyl, isoindolinyl, dihydrobenzofuranyl, dihydrobenzothiophenyl, benzoxazolinonyl, etc. Exemplary 6-membered heterocyclyl groups fused with a $C_6$ aryl (also referred as 6, 6-bicyclic heterocyclyl herein) include, but are not limited to, tetrahydroquinolinyl, tetrahydroisoquinolinyl, etc.

The 3- to 11-membered heterocyclyl also includes spiroheterocyclyl, that is, a group in which two rings (e.g., a heterocycle and a carbocycle) share a carbon atom, wherein at least one of the rings is a heterocyclyl as defined above. More specifically, the spiroheterocyclyl is a spiro ring formed by two 4-membered rings, two 5-membered rings, two 6-membered rings, one 4-membered ring and one 5-membered ring, one 4-membered ring and one 6-membered ring, or one 5-membered ring and one 6-membered ring, wherein at least one of the rings is a 4- to 6-membered heterocyclyl as defined above. The 4- to 6-membered heterocyclyl containing 1, 2 or 3 O, N or S heteroatoms is preferred. The 4- to 6-membered heterocyclyl containing 1 N heteroatom is more preferred. Specific spiroheterocyclyl groups include, but are not limited to:

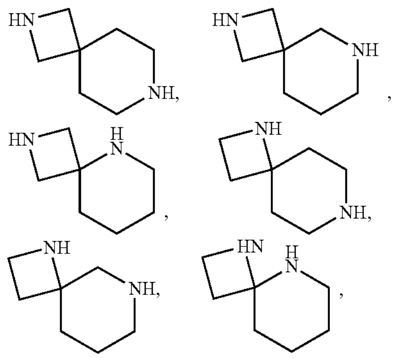

-continued

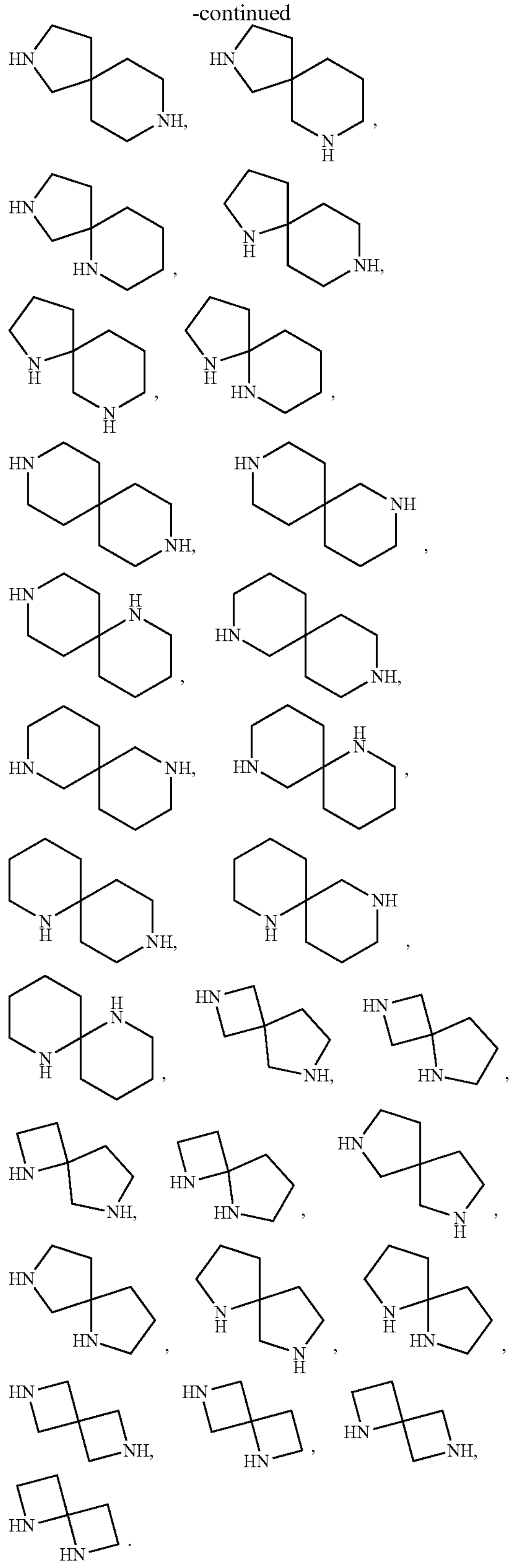

"$C_{6-10}$ aryl" refers to a radical of monocyclic or polycyclic (e.g., bicyclic) 4n+2 aromatic ring system having 6-10 ring carbon atoms and zero heteroatoms (e.g., having 6 or 10 shared π electrons in a cyclic array). In some embodiments, the aryl group has six ring carbon atoms ("$C_6$ aryl"; for example, phenyl). In some embodiments, the aryl group has ten ring carbon atoms ("$C_{10}$ aryl"; for example, naphthyl, e.g., 1-naphthyl and 2-naphthyl). The aryl group also includes a ring system in which the aryl ring described above is fused with one or more cycloalkyl or heterocyclyl groups, and the point of attachment is on the aryl ring, in which case the number of carbon atoms continues to represent the number of carbon atoms in the aryl ring system.

"5- to 10-membered heteroaryl" refers to a radical of 5- to 10-membered monocyclic or bicyclic 4n+2 aromatic ring system (e.g., having 6 or 10 shared π electrons in a cyclic array) having ring carbon atoms and 1-4 ring heteroatoms, wherein each heteroatom is independently selected from nitrogen, oxygen and sulfur. In the heteroaryl group containing one or more nitrogen atoms, the point of attachment can be a carbon or nitrogen atom as long as the valence permits. Heteroaryl bicyclic systems may include one or more heteroatoms in one or two rings. Heteroaryl also includes ring systems wherein the heteroaryl ring described above is fused with one or more cycloalkyl or heterocyclyl groups, and the point of attachment is on the heteroaryl ring. In such case, the number the carbon atoms continues to represent the number of carbon atoms in the heteroaryl ring system. In some embodiments, 5- to 6-membered heteroaryl groups are particularly preferred, which are radicals of 5- to 6-membered monocyclic or bicyclic 4n+2 aromatic ring systems having ring carbon atoms and 1-4 ring heteroatoms. Exemplary 5-membered heteroaryl groups containing one heteroatom include, but are not limited to, pyrrolyl, furyl and thienyl. Exemplary 5-membered heteroaryl groups containing two heteroatoms include, but are not limited to, imidazolyl, pyrazolyl, oxazolyl, isoxazolyl, thiazolyl, and isothiazolyl. Exemplary 5-membered heteroaryl groups containing three heteroatoms include, but are not limited to, triazolyl, oxadiazolyl (such as, 1, 2, 4-oxadiazoly), and thiadiazolyl. Exemplary 5-membered heteroaryl groups containing four heteroatoms include, but are not limited to, tetrazolyl. Exemplary 6-membered heteroaryl groups containing one heteroatom include, but are not limited to, pyridyl. Exemplary 6-membered heteroaryl groups containing two heteroatoms include, but are not limited to, pyridazinyl, pyrimidinyl, and pyrazinyl. Exemplary 6-membered heteroaryl groups containing three or four heteroatoms include, but are not limited to, triazinyl and tetrazinyl, respectively. Exemplary 7-membered heteroaryl groups containing one heteroatom include, but are not limited to, azepinyl, oxepinyl, and thiepinyl. Exemplary 5,6-bicyclic heteroaryl groups include, but are not limited to, indolyl, isoindolyl, indazolyl, benzotriazolyl, benzothiophenyl, isobenzothiophenyl, benzofuranyl, benzoisofuranyl, benzimidazolyl, benzoxazolyl, benzoisoxazolyl, benzoxadiazolyl, benzothiazolyl, benzoisothiazolyl, benzothiadiazolyl, indolizinyl and purinyl. Exemplary 6, 6-bicyclic heteroaryl groups include, but are not limited to, naphthyridinyl, pteridinyl, quinolyl, isoquinolyl, cinnolinyl, quinoxalinyl, phthalazinyl and quinazolinyl.

"carbonyl", whether used alone or in conjunction with other terms (e.g., aminocarbonyl), is represented by —C(O)—.

"Oxo" represents =O.

"Thioxo" represents =S.

Alkyl, alkenyl, alkynyl, carbocyclyl, heterocyclyl, aryl, and heteroaryl groups, as defined herein, are optionally substituted groups. In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary substituents on carbon atoms include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3{}^+X^-$, —$N(OR^{cc})R^{bb}$, —SH, —$SR^{aa}$, —$SSR^{cc}$, —$C(=O)R^{aa}$, —$CO_2H$, —CHO, —$C(OR^{cc})_2$, —$CO_2R^{aa}$, —$OC(=O)R^{aa}$, —$OCO_2R^{aa}$, —$C(=O)N(R^{bb})_2$, —$OC(=O)N(R^{bb})_2$, —$NR^{bb}C(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})OR^{aa}$, —$OC(=NR^{bb})R^{aa}$, —$OC(=NR^{bb})OR^{aa}$, —$C(=NR^{bb})N(R^{bb})_2$—$OC(=NR^{bb})N(R^{bb})_2$—$NR^{bb}C(=NR^{bb})N(R^{bb})_2$, —$C(=O)NR^{bb}SO_2R^{aa}$, —$NR^{bb}SO_2R^{aa}$, —$SO_2N(Reb)_2$, —$SO_2R^{aa}$, —$SO_2OR^{aa}$, —$OSO_2R^{aa}$, —$S(=O)R^{aa}$, —$OS(=O)R^{aa}$, —$Si(R^{aa})_3$, —$OSi(R^{aa})_3$—$C(=S)N(R^{bb})_2$, —$C(=O)SR^{aa}$, —$C(=S)SR^{aa}$, —$SC(=S)SR^{aa}$, —$SC(=O)SR^{aa}$, —$OC(=O)SR^{aa}$, —$SC(=O)OR^{aa}$, —$SC(=O)R^{aa}$, —$P(=O)_2R^{aa}$, —$OP(=O)_2R^{aa}$, —$P(=O)(R^{aa})_2$, —$OP(=O)(R^{aa})_2$, —$OP(=O)(OR^{cc})_2$, —$P(=O)_2N(R^{bb})_2$, —$OP(=O)_2N(R^{bb})_2$, —$P(=O)(NR^{bb})_2$, —$OP(=O)(NR^{bb})_2$, —$NR^{bb}P(=O)(OR^{cc})_2$, —$NR^{bb}P(=O)(NR^{bb})_2$, —$P(R^{cc})_2$, —$P(R^{cc})_3$, —$OP(R^{cc})_2$, —$OP(R^{cc})_3$, —$B(R^{aa})_2$, —$B(OR^{cc})_2$, —$BR^{aa}(OR^{cc})$, alkyl, haloalkyl, alkenyl, alkynyl, carbocyclyl, heterocyclyl, aryl and heteroaryl, wherein each of the alkyl, alkenyl, alkynyl, carbocyclyl, heterocyclyl, aryl and heteroaryl is independently substituted with 0, 1, 2, 3, 4 or 5 $R^{dd}$ groups;

or two geminal hydrogen on a carbon atom are replaced with =O, =S, =$NN(R^{bb})_2$, =$NNR^{bb}C(=O)R^{aa}$=$NNR^{bb}C(=O)OR^{aa}$=$NNR^{bb}S(=O)_2R^{aa}$=$NR^{bb}$ or =$NOR^{cc}$ groups;

each of the $R^a$ is independently selected from alkyl, haloalkyl, alkenyl, alkynyl, carbocyclyl, heterocyclyl, aryl and heteroaryl, or two of the $R^{aa}$ groups are combined to form a heterocyclyl or heteroaryl ring, wherein each of the alkyl, alkenyl, alkynyl, carbocyclyl, heterocyclyl, aryl and heteroaryl is independently substituted with 0, 1, 2, 3, 4 or 5 Rad groups;

each of the $R^{bb}$ is independently selected from hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR_c)OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, —$P(=O)_2R^{aa}$, —$P(=O)(R^{aa})_2$, —$P(=O)_2N(R^{cc})_2$, —$P(=O)(NR^{cc})_2$, alkyl, haloalkyl, alkenyl, alkynyl, carbocyclyl, heterocyclyl, aryl and heteroaryl, or two $R^{bb}$ groups are combined to form a heterocyclyl or a heteroaryl ring, wherein each of the alkyl, alkenyl, alkynyl, carbocyclyl, heterocyclyl, aryl and heteroaryl is independently substituted with 0, 1, 2, 3, 4 or 5 Rad groups;

each of the $R^{cc}$ is independently selected from hydrogen, alkyl, haloalkyl, alkenyl, alkynyl, carbocyclyl, heterocyclyl, aryl and heteroaryl, or two $R^{cc}$ groups are combined to form a heterocyclyl or a heteroaryl ring, wherein each of the alkyl, alkenyl, alkynyl, carbocyclyl, heterocyclyl, aryl and heteroaryl is independently substituted with 0, 1, 2, 3, 4 or 5 Rad groups;

each of the Rad is independently selected from halogen, —CN, —$NO_2$, —$N_3$, —$SO_2H$, —$SO_3H$, —OH, —$OR^{cc}$, —$ON(R^{ff})_2$, —$N(R_{ff})_2$, —$N(R^{ff})_3{}^+X^-$, —$N(OR^{cc})R^{ff}$, —SH, —$SR^{cc}$, —$SSR^{cc}$, —C(═O)$R^{cc}$, —$CO_2H$, —$CO_2R^{cc}$, —OC(═O)$R^{cc}$, —$OCO_2R^{cc}$, —C(═O)$N(R_{ff})_2$, —OC(═O)$N(R_{ff})_2$, —$NR^{ff}$C(═O)$R^{cc}$, —$NR^{ff}CO_2R^{cc}$, —$NR_{ff}$C(═O)$N(R_{ff})_2$, —C(═$NR^{ff}$)$OR^{cc}$, —OC(═$NR^{ff}$)$R^{cc}$, —OC(═$NR^{ff}$)$OR^{cc}$, —C(═$NR_{ff}$)$N(R_{ff})_2$, —OC(═$NR_{ff}$)$N(R_{ff})_2$, —$NR^{ff}$C(═$NR_{ff}$)$N(R_{ff})_2$, —$NR^{ff}SO_2R^{ee}$, —$SO_2N(R^{ff})_2$, —$SO_2R^{ee}$, —$SO_2OR^{ee}$, —$OSO_2R^{ee}$, —S(═O)$R^{ee}$, —$Si(R^{ee})_3$, —$OSi(R^{ee})_3$, —C(═S)$N(R^{ff})_2$, —C(═O)$SR^{ee}$, —C(═S)$SR^{ee}$, —SC(═S)$SR^{ee}$, —P(═$O)_2R^{ee}$, —P(═O)$(R^{ee})_2$, —OP(═O)$(R^{ee})_2$, —OP(═O)$(OR^{ee})_2$, alkyl, haloalkyl, alkenyl, alkynyl, carbocyclyl, heterocyclyl, aryl, heteroaryl, wherein each of the alkyl, alkenyl, alkynyl, carbocyclyl, heterocyclyl, aryl and heteroaryl is independently substituted with 0, 1, 2, 3, 4 or 5 $R^{gg}$ groups, or two geminal $R_d$ substituents can be combined to form ═O or ═S;

each of the $R^{ee}$ is independently selected from alkyl, haloalkyl, alkenyl, alkynyl, carbocyclyl, aryl, heterocyclyl, and heteroaryl, wherein each of the alkyl, alkenyl, alkynyl, carbocyclyl, heterocyclyl, aryl and heteroaryl is independently substituted with 0, 1, 2, 3, 4 or 5 $R^{gg}$ groups;

each of the $R^f$ is independently selected from hydrogen, alkyl, haloalkyl, alkenyl, alkynyl, carbocyclyl, heterocyclyl, aryl and heteroaryl, or two $R^f$ groups are combined to form a heterocyclyl or a heteroaryl ring, wherein each of the alkyl, alkenyl, alkynyl, carbocyclyl, heterocyclyl, aryl and heteroaryl is independently substituted with 0, 1, 2, 3, 4 or 5 $R^{gg}$ groups;

each of the $R^{gg}$ is independently selected from halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3{}^+X^-$, —$NH(C_{1-6}$ alkyl$)_2{}^+X^-$, —$NH_2(C_{1-6}$ alkyl$)^+X^-$, —$NH_3{}^+X^-$, —$N(OC_{1-6}$ alkyl$)(C_{1-6}$ alkyl), —N(OH)($C_{1-6}$ alkyl), —NH(OH), —SH, —$SC_{1-6}$ alkyl, —SS($C_{1-6}$ alkyl), —C(═O)($C_{1-6}$ alkyl), —$CO_2H$, —$CO_2(C_{1-6}$ alkyl), —OC(═O)($C_{1-6}$ alkyl), —$OCO_2(C_{1-6}$ alkyl), —C(═O)$NH_2$, —C(═O)$N(C_{1-6}$ alkyl$)_2$, —OC(═O)NH($C_{1-6}$ alkyl), —NHC(═O)($C_{1-6}$ alkyl), —$N(C_{1-6}$ alkyl)C(═O)($C_{1-6}$ alkyl), —$NHCO_2(C_{1-6}$ alkyl), —NHC(═O)$N(C_{1-6}$ alkyl$)_2$, —NHC(═O)NH($C_{1-6}$ alkyl), —NHC(═O)$NH_2$, —C(═NH)O($C_{1-6}$ alkyl), —OC(═NH)($C_{1-6}$ alkyl), —OC(═NH)$OC_{1-6}$ alkyl, —C(═NH)$N(C_{1-6}$ alkyl$)_2$, —C(═NH)NH($C_{1-6}$ alkyl), —C(═NH)$NH_2$, —OC(═NH)$N(C_{1-6}$ alkyl$)_2$, —OC(NH)NH($C_{1-6}$ alkyl), —OC(NH)$NH_2$, —NHC(NH)$N(C_{1-6}$ alkyl$)_2$, —NHC(═NH)$NH_2$, —$NHSO_2(C_{1-6}$ alkyl), —$SO_2N(C_{1-6}$ alkyl$)_2$, —$SO_2NH(C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —$Si(C_{1-6}$ alkyl$)_3$, —$OSi(C_{1-6}$ alkyl$)_3$, —C(═S)$N(C_{1-6}$ alkyl$)_2$, C(═S)NH($C_{1-6}$ alkyl), C(═S)$NH_2$, —C(═O)S($C_{1-6}$ alkyl), —C(═S)$SC_{1-6}$ alkyl, —SC(═S)$SC_{1-6}$ alkyl, —P(═$O)_2(C_{1-6}$ alkyl), —P(═O)$(C_{1-6}$ alkyl$)_2$, —OP(═O)$(C_{1-6}$ alkyl$)_2$, —OP(═O)$(OC_{1-6}$ alkyl$)_2$, $C_{1-6}$ alkyl, $C_{1-6}$ haloalkyl, $C_2$-$C_6$ alkenyl, $C_2$-$C_6$ alkynyl, $C_3$-$C_7$ carbocyclyl, $C_6$-$C_{10}$ aryl, $C_3$-$C_7$ heterocyclyl, $C_5$-$C_{10}$ heteroaryl; or two geminal $R^{gg}$ substituents may combine to form ═O or ═S; wherein $X^-$ is a counterion.

Exemplary substituents on nitrogen atoms include, but are not limited to, hydrogen, —OH, —$OR^{aa}$, —$N(R^{cc})_2$, —CN, —C(═O)$R^{aa}$, —C(═O)$N(R^{cc})_2$, —$CO_2R^{aa}$, —$SO_2R^{aa}$, —C(═$NR^{bb}$)$R^{aa}$, —C(═$NR^{cc}$)$OR^{aa}$, —C(═$NR^{cc}$)$N(R^{cc})_2$, —$SO_2N(R^{cc})_2$, —$SO_2R^{cc}$, —$SO_2OR^{cc}$, —$SOR^{aa}$, —C(═S)$N(R^{cc})_2$, —C(═O)$SR^{cc}$, —C(═S)$SR^{cc}$, —P(═$O)_2R_a{}^a$, —P(═O)$(R^{aa})_2$, —P(═$O)_2N(R^{cc})_2$, —P(═O)$(NR^{cc})_2$, alkyl, haloalkyl, alkenyl, alkynyl, carbocyclyl, heterocyclyl, aryl and heteroaryl, or two $R^{cc}$ groups attached to a nitrogen atom combine to form a heterocyclyl or a heteroaryl ring, wherein each of the alkyl, alkenyl, alkynyl, carbocyclyl, heterocyclyl, aryl and heteroaryl is independently substituted with 0, 1, 2, 3, 4 or 5 $R^{dd}$ groups, and wherein $R^{aa}$, $R^{bb}$, $R^{cc}$ and $R^{dd}$ are as described herein.

Other Definitions

As used herein, "cancer" refers to any disease induced or caused by inappropriately high levels of cell division, inappropriately low levels of apoptosis, or both. Examples of cancer include, but are not limited to, leukemias (e.g., acute leukemia, acute lymphoblastic leukemia, acute myeloid leukemia, acute myelogenous leukemia, acute promyelocytic leukemia, acute myelomonocytic leukemia, acute monocytic leukemia, acute erythrocytic leukemia, chronic leukemia, chronic myelogenous leukemia, chronic lymphocytic leukemia), polycythemia vera, lymphoma (Hodgkin's disease, non-Hodgkin's disease), Waldenstrom's Macroglobulinemia, heavy chain disease and solid tumors.

The term "treating" as used herein relates to reversing, alleviating or inhibiting the progression or prevention of the disorders or conditions to which the term applies, or of one or more symptoms of such disorders or conditions. The noun "treatment" as used herein relates to the action of treating, which is a verb, and the latter is as just defined.

The term "pharmaceutically acceptable" as used herein refers to the substance, which are suitable for the contact with patients' tissues within a reliable medical judgment, and do not produce inappropriate toxicity, irritation, allergy, etc. They are commensurate with a reasonable benefit/risk ratio, and are effective for their intended use. The term includes, if possible, the zwitterionic form of the compounds of the disclosure.

The term "salt" refers to a relatively non-toxic addition salt of inorganic and organic acids to the compounds of the present disclosure. These salts can be prepared in situ during the final separation and purification of the compounds, or by isolating salts produced by separately reacting the purified compound in the free base form with a suitable organic or inorganic acid.

The pharmaceutically acceptable base addition salts are formed with metals or amines, such as alkali metal and alkaline earth metal hydroxides or organic amines. Examples of the metals used as cations include sodium, potassium, magnesium, calcium, etc. Examples of suitable amines are N, N'-dibenzylethylenediamine, chloroprocaine, choline, diethanolamine, ethylenediamine, N-methylglucamine and procaine.

The salts can be prepared from the inorganic acids, which include sulfates, pyrosulfates, bisulfates, sulfites, bisulfites, nitrates, phosphates, monohydrogen phosphates, dihydrogen phosphates, metaphosphates, pyrophosphates, chlorides, bromides and iodides. Examples of the acids include hydrochloric acid, nitric acid, sulfuric acid, hydrobromic acid, hydroiodic acid, phosphoric acid, etc. The representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthalate, methanesulfonate, glucoheptanate, lactobionate, lauryl sulfonate, isethionate, etc. The salts can also be prepared from the organic acids, which include aliphatic monocarboxylic and dicarboxylic acids, phenyl-substituted alkanoic acids, hydroxyalkanoic acids, alkanedioic acid, aromatic acids, aliphatic and aromatic sulfonic acids, etc. The representative salts include acetate, propionate, octanoate, isobutyrate, oxalate, malonate, succinate, suberate, sebacate, fumarate, maleate, mandelate, benzoate, chlorobenzoate, methyl benzoate, dinitrobenzoate, naphthoate, besylate, tosylate, phenylacetate, citrate, lactate, maleate, tartrate, methanesulfonate, etc. The pharmaceutically acceptable salts can include cations based on alkali metals and alkaline earth metals, such as sodium, lithium, potassium, calcium, magnesium, etc., as well as non-toxic ammonium, quaternary ammonium, and amine cations including, but not limited to, ammonium, tetramethylammonium, tetraethylammonium, methylamine, dimethylamine, trimethylamine, triethylamine, ethylamine, etc. Salts of amino acids are also included, such as arginine salts, gluconates, galacturonates, etc. (for example, see Berge S. M. et al., "Pharmaceutical Salts," J. Pharm. Sci., 1977; 66: 1-19 for reference).

"Subjects" to which administration is contemplated include, but are not limited to, humans (e.g., males or females of any age group, e.g., paediatric subjects (e.g., infants, children, adolescents) or adult subjects (e.g., young adults, middle-aged adults or older adults) and/or non-human animals, such as mammals, e.g., primates (e.g., cynomolgus monkeys, rhesus monkeys), cattle, pigs, horses, sheep, goats, rodents, cats and/or dogs. In some embodiments, the subject is a human. In some embodiments, the subject is a non-human animal. The terms "human", "patient" and "subject" can be used interchangeably herein.

"Disease," "disorder," and "condition" can be used interchangeably herein.

Unless indicated, otherwise the term "treatment" as used herein includes the effect on a subject who is suffering from a particular disease, disorder, or condition, which reduces the severity of the disease, disorder, or condition, which reduces the severity of the disease, disorder or condition, or delays or slows the progression of the disease, disorder or condition ("therapeutic treatment"). The term also includes the effect that occurs before the subject begins to suffer from a specific disease, disorder or condition ("prophylactic treatment").

Generally, the "effective amount" of a compound refers to an amount sufficient to elicit a target biological response. As understood by those skilled in the art, the effective amount of the compound of the disclosure can vary depending on the following factors, such as the desired biological endpoint, the pharmacokinetics of the compound, the diseases being treated, the mode of administration, and the age, health status and symptoms of the subjects. The effective amount includes therapeutically effective amount and prophylactically effective amount.

Unless indicated, otherwise the "therapeutically effective amount" of the compound as used herein is an amount sufficient to provide therapeutic benefits in the course of treating a disease, disorder or condition, or to delay or minimize one or more symptoms associated with the disease, disorder or condition. The therapeutically effective amount of a compound refers to the amount of the therapeutic agent that, when used alone or in combination with other therapies, provides a therapeutic benefit in the treatment of a disease, disorder or condition. The term "therapeutically effective amount" can include an amount that improves the overall treatment, reduces or avoids the symptoms or causes of the disease or condition, or enhances the therapeutic effect of other therapeutic agents.

Unless indicated, otherwise the "prophylactically effective amount" of the compound as used herein is an amount sufficient to prevent a disease, disorder or condition, or an amount sufficient to prevent one or more symptoms associated with a disease, disorder or condition, or an amount sufficient to prevent the recurrence of a disease, disorder or condition. The prophylactically effective amount of a compound refers to the amount of a therapeutic agent that, when used alone or in combination with other agents, provides a prophylactic benefit in the prevention of a disease, disorder or condition. The term "prophylactically effective amount" can include an amount that improves the overall prevention, or an amount that enhances the prophylactic effect of other preventive agents.

"Combination" and related terms refer to the simultaneous or sequential administration of the compounds of the present disclosure and other therapeutic agents. For example, the compounds of the present disclosure can be administered simultaneously or sequentially in separate unit dosage with other therapeutic agents, or simultaneously in a single unit dosage with other therapeutic agents.

DETAILED DESCRIPTION OF THE INVENTION

As used herein, "compounds of the present disclosure" refer to the compounds of formula (I) below, or pharmaceutically acceptable salts, enantiomers, diastereomers, racemates, solvates, hydrates, polymorphs, prodrugs or isotope variants thereof, and mixtures thereof.

Compounds are generally described herein using standard nomenclature. It should be understood, unless otherwise specified, that compounds with asymmetric center(s) include all optical isomers and mixtures thereof. Furthermore, unless otherwise specified, all isomer compounds and carbon-carbon double bonds included in the present disclosure may be in the form of Z and E. Compounds which exist in different tautomeric forms, one of which is not limited to any particular tautomer, but is intended to cover all tautomeric forms.

In one embodiment, the present disclosure refers to a compound of formula (I), or a pharmaceutically acceptable salt, an enantiomer, a diastereomer, a racemate, a solvate, a hydrate, a polymorph, a prodrug, or an isotope variant thereof, and mixtures thereof:

(I)

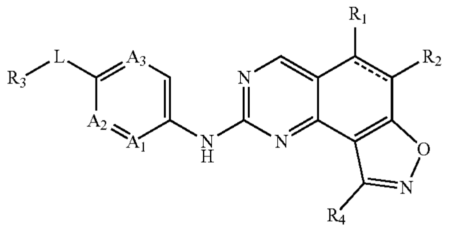

wherein:

$\overline{\text{- - -}}$ indicates a single bond or a double bond;

$A_1$ is selected from $CR_5$ or N;

$A_2$ is selected from $CR_6$ or N;

$A_3$ is selected from $CR_7$ or N;

$R_1$ is selected from H, D, halogen, —CN, —$OR_a$, —$SR_a$, —$NR_bR_c$, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl; wherein the said $C_{3-7}$ cycloalkyl or 3- to 7-membered heterocyclyl is optionally substituted by oxo or thioxo;

$R_2$ is selected from H, D, halogen, —CN, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl; wherein the said $C_{3-7}$ cycloalkyl or 3- to 7-membered heterocyclyl is optionally substituted by oxo or thioxo;

$R_3$ is selected from H, D, halogen, —CN, —$NO_2$, —$OR_a$, —$SR_a$, —$NR_bR_c$, —C(O)$R_a$, —C(O)$OR_a$, —C(O)$NR_bR_c$, —S(O)$_mR_a$, —S(O)$_mOR_a$, —S(O)$_mNR_bR_c$, —O—$C_{1-6}$ alkylene-$R_8$, $C_{1-6}$ alkyl, $C_{1-6}$ haloalkyl, $C_{3-7}$ cycloalkyl, 3- to 11-membered heterocyclyl, $C_{6-10}$ aryl, or 5- to 10-membered heteroaryl, each of which is optionally substituted by 1, 2, 3, 4, or 5 $R_8$ groups;

$R_4$ is selected from H, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl;

L is selected from a chemical bond, —O—, —NH—, —C(O)—, —C(O)NH—, —NHC(O)—, —$C_{1-6}$ alkylene-, —$C_{2-6}$ alkenylene- or —$C_{2-6}$ alkynylene-;

and wherein, $R_5$ is selected from H, D, halogen, —CN, —$OR_a$, —$SR_a$, —$NR_bR_c$, —C(O)$R_a$, —C(O)$OR_a$, —C(O)$NR_bR_c$, —S(O)$_mR_a$, —S(O)$_mOR_a$, —S(O)$_mNR_bR_c$, $C_{1-6}$ alkyl or $C_{1-6}$ haloalkyl;

$R_6$ is selected from H, D, halogen, —CN, —$OR_a$, —$SR_a$, —$NR_bR_c$, —C(O)$R_a$, —C(O)$OR_a$, —C(O)$NR_bR_c$, —S(O)$_mR_a$, —S(O)$_mOR_a$, —S(O)$_mNR_bR_c$, $C_{1-6}$ alkyl or $C_{1-6}$ haloalkyl;

$R_7$ is selected from H, D, halogen, —CN, —$OR_a$, —$SR_a$, —$NR_bR_c$, —C(O)$R_a$, —C(O)$OR_a$, —C(O)$NR_bR_c$, —S(O)$_mR_a$, —S(O)$_mOR_a$, —S(O)$_mNR_bR_c$, $C_{1-6}$ alkyl or $C_{1-6}$ haloalkyl;

$R_8$ is selected from H, D, —$NH_2$, —$NHC_{1-6}$ alkyl, —N($C_{1-6}$ alkyl)$_2$, $C_{1-6}$ alkyl, $C_{1-6}$ haloalkyl, —$C_{0-6}$ alkylene-$OR_a$, $C_{3-7}$ cycloalkyl, 3- to 7-membered heterocyclyl, $C_{6-10}$ aryl, or 5- to 10-membered heteroaryl; or two $R_8$ on the same atom are taken together to form oxo or thioxo;

$R_a$ is independently selected from H, —$C_{0-6}$ alkylene-CN, —$C_{0-6}$ alkylene-$NO_2$, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C(O)OR', —$C_{0-6}$ alkylene-C(O)NR"R'", —$C_{0-6}$ alkylene-S(O)$_m$R', —$C_{0-6}$ alkylene-S(O)$_m$OR', —$C_{0-6}$ alkylene-S(O)$_m$NR"R'", $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl;

$R_b$ and $R_c$ are independently selected from H, —$C_{0-6}$ alkylene-CN, —$C_{0-6}$ alkylene-$NO_2$, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C(O)OR', —$C_{0-6}$ alkylene-C(O)NR"R'", —$C_{0-6}$ alkylene-S(O)$_m$R', —$C_{0-6}$ alkylene-S(O)$_m$OR', —$C_{0-6}$ alkylene-S(O)$_m$NR"R'", $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or, $R_b$, $R_c$ and N atom are taken together to form 3- to 7-membered heterocyclyl;

R' is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl;

R" and R'" are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl; or, R", R'" and N atom are taken together to form 3- to 7-membered heterocyclyl;

m represents 0, 1, or 2;

and, $R_1$-$R_2$ and $R_4$-$R_8$ are optionally substituted with 1, 2 or 3 R groups, wherein the R is independently selected from H, —OH, halogen, —$NO_2$, carbonyl, —CN, —$OR_a$, —$SR_a$, —$NR_bR_c$, —C(O)$R_a$, —C(S)$R_a$, —C(O)$OR_a$, —C(S)$OR_a$, —C(O)—$NR_bR_c$, —C(S)—$NR_bR_c$, —O—C(O)$R_a$, —O—C(S)$R_a$, —N($R_b$)—C(O)—$R_a$, —N($R_b$)—C(S)—$R_a$, —S(O)$_mR_a$, —S(O)$_mOR_a$, —S(O)$_mNR_bR_c$, —N($R_b$)—S(O)$_m$—$R_a$, —N($R_b$)—S(O)$_m$—$NR_bR_c$, —N($R_b$)—C(O)$OR_a$, —N($R_b$)—C(S)$OR_a$, —O—$C_{1-6}$ alkylene-$OR_a$, —C(O)—$C_{1-6}$ alkylene-$NR_bR_c$, —N($R_b$)—C(O)—$NR_bR_c$, —N($R_b$)—C(S)—$NR_bR_c$, —O—C(O)—$NR_bR_c$, —O—C(S)—$NR_bR_c$, $C_{1-6}$ alkyl, $C_{1-6}$ haloalkyl, $C_{2-6}$ alkenyl, $C_{2-6}$ alkynyl, $C_{3-7}$ cycloalkyl, 3- to 7-membered heterocyclyl, $C_{6-10}$ aryl, or 5- to 10-membered heteroaryl; wherein the said $C_{1-6}$ alkyl, $C_{1-6}$ haloalkyl, $C_{2-6}$ alkenyl, $C_{2-6}$ alkynyl, $C_{3-7}$ cycloalkyl, 3- to 7-membered heterocyclyl, $C_{6-10}$ aryl or 5- to 10-membered heteroaryl is each further optionally substituted by one or more groups consisting of the following:

—CN, —$NO_2$, carbonyl, —$OR_a$, —$SR_a$, —$NR_bR_c$, —C(O)$R_a$, —C(S)$R_a$, —C(O)$OR_a$, —C(S)$OR_a$, —C(O)—$NR_bR_c$, —C(S)—$NR_bR_c$, —O—C(O)$R_a$, —O—C(S)$R_a$, —N($R_b$)—C(O)—$R_a$, —N($R_b$)—C(S)—$R_a$, —S(O)$_mR_a$, —S(O)$_mOR_a$, —S(O)$_mNR_bR_c$, —N($R_b$)—S(O)$_m$—$R_a$, —N($R_b$)—S(O)$_m$—$R_bR_c$, —N($R_b$)—C(O)$OR_a$, —N($R_b$)—C(S)$OR_a$, —O—$C_{1-6}$ alkylene-$OR_a$, —C(O)—$C_{1-6}$ alkylene-$NR_bR_c$, —N($R_b$)—C(O)—$NR_bR_c$, —N($R_b$)—C(S)—$NR_bR_c$, —O—C(O)—$NR_bR_c$ or —O—C(S)—$NR_bR_c$;

$R_a$, $R_b$ and $R_c$ are each further optionally substituted by one or more groups consisting of the following:

$C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl.

In a embodiment, the present disclosure relates to a compound of general formula (I), or a pharmaceutically acceptable salt, an enantiomer, a diastereomer, a racemate, a solvate, a hydrate, a polymorph, a prodrug, or an isotope variant thereof, and mixtures thereof:

(I)

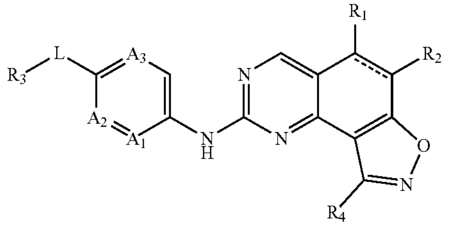

wherein:

⎓ indicates a single bond or a double bond;

$A_1$ is selected from $CR_5$ or N;

$A_2$ is selected from $CR_6$ or N;

$A_3$ is selected from $CR_7$ or N;

$R_1$ is selected from H, halogen, —CN, —$OR_a$, —$SR_a$, —$NR_bR_c$, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl; wherein the said $C_{3-7}$ cycloalkyl or 3- to 7-membered heterocyclyl is optionally substituted by oxo or thioxo;

$R_2$ is selected from H, halogen, —CN, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl; wherein the said $C_{3-7}$ cycloalkyl or 3- to 7-membered heterocyclyl is optionally substituted by oxo or thioxo;

$R_3$ is selected from H, halogen, —CN, —$NO_2$, —$OR_a$, —$SR_a$, —$NR_bR_c$, —C(O)$R_a$, —C(O)$OR_a$, —C(O)$NR_bR_c$, —S(O)$_mR_a$, —S(O)$_mOR_a$, —S(O)$_m$ $NR_bR_c$, —O—$C_{1-6}$ alkylene-$R_8$, $C_{1-6}$ alkyl, $C_{1-6}$ haloalkyl, $C_{3-7}$ cycloalkyl, 3- to 11-membered heterocyclyl, $C_{6-10}$ aryl, or 5- to 10-membered heteroaryl, each of which is optionally substituted by 1, 2, 3, 4, or 5 $R_8$ groups;

$R_4$ is selected from H, —C(O)$R_a$, —C(O)$OR_a$, —C(O) $NR_bR_c$, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl;

L is selected from a chemical bond, —O—, —NH—, —C(O)—, —C(O)NH—, —NHC(O)—, —$C_{1-6}$ alkylene-, —$C_{2-6}$ alkenylene- or —$C_{2-6}$ alkynylene-;

and wherein, $R_5$ is selected from H, halogen, —CN, —$OR_a$, —$SR_a$, —$NR_bR_c$, —C(O)$R_a$, —C(O)$OR_a$, —C(O)$NR_bR_c$, $C_{1-6}$ alkyl or $C_{1-6}$ haloalkyl;

$R_6$ is selected from H, halogen, —CN, —$OR_a$, —$SR_a$, —$NR_bR_c$, —C(O)$R_a$, —C(O)$OR_a$, —C(O)$NR_bR_c$, $C_{1-6}$ alkyl or $C_{1-6}$ haloalkyl;

$R_7$ is selected from H, halogen, —CN, —$OR_a$, —$SR_a$, —$NR_bR_c$, —C(O)$R_a$, —C(O)$OR_a$, —C(O)$NR_bR_c$, $C_{1-6}$ alkyl or $C_{1-6}$ haloalkyl;

$R_8$ is selected from H, —$NH_2$, —$NHC_{1-6}$ alkyl, —N($C_{1-6}$ alkyl)$_2$, $C_{1-6}$ alkyl, $C_{1-6}$ haloalkyl, —$C_{0-6}$ alkylene-$OR_a$, $C_{3-7}$ cycloalkyl, 3- to 7-membered heterocyclyl, $C_{6-10}$ aryl, or 5- to 10-membered heteroaryl; or two $R_8$ on the same atom are taken together to form oxo or thioxo;

$R_a$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl;

$R_b$ and $R_c$ are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl; or, $R_b$, $R_c$ and N atom are taken together to form 3- to 7-membered heterocyclyl;

m represents 0, 1, or 2;

and, $R_1$-$R_2$ and $R_4$-$R_8$ are optionally substituted with 1, 2 or 3 R groups, wherein the R is independently selected from H, —OH, halogen, —$NO_2$, carbonyl, —CN, —$OR_a$, —$SR_a$, —$NR_bR_c$, —C(O)$R_a$, —C(S)$R_a$, —C(O)$OR_a$, —C(S)$OR_a$, —C(O)—$NR_bR_c$, —C(S)—$NR_bR_c$, —O—C(O)$R_a$, —O—C(S)$R_a$, —N($R_b$)—C(O)—$R_a$, —N($R_b$)—C(S)—$R_a$, —S(O)$_mR_a$, —S(O)$_mOR_a$, —S(O)$_mNR_bR_c$, —N($R_b$)—S(O)$_m$—$R_a$, —N($R_b$)—S(O)$_m$—$NR_bR_c$, —N($R_b$)—C(O)$OR_a$, —N($R_b$)—C(S)$OR_a$, —O—$C_{1-6}$ alkylene-$OR_a$, —C(O)—$C_{1-6}$ alkylene-$NR_bR_c$, —N($R_b$)—C(O)—$NR_bR_c$, —N($R_b$)—C(S)—$NR_bR_c$, —O—C(O)—$NR_bR_c$, —O—C(S)—$NR_bR_c$, $C_{1-6}$ alkyl, $C_{1-6}$ haloalkyl, $C_{2-6}$ alkenyl, $C_{2-6}$ alkynyl, $C_{3-7}$ cycloalkyl, 3- to 7-membered heterocyclyl, $C_{6-10}$ aryl, or 5- to 10-membered heteroaryl; wherein the said $C_{1-6}$ alkyl, $C_{1-6}$ haloalkyl, $C_{2-6}$ alkenyl, $C_{2-6}$ alkynyl, $C_{3-7}$ cycloalkyl, 3- to 7-membered heterocyclyl, $C_{6-10}$ aryl or 5- to 10-membered heteroaryl is each further optionally substituted by one or more groups consisting of the following:

—CN, —$NO_2$, carbonyl, —$OR_a$, —$SR_a$, —$NR_bR_c$, —C(O)$R_a$, —C(S)$R_a$, —C(O)$OR_a$, —C(S)$OR_a$, —C(O)—$NR_bR_c$, —C(S)—$NR_bR_c$, —O—C(O)$R_a$, —O—C(S)$R_a$, —N($R_b$)—C(O)—$R_a$, —N($R_b$)—C(S)—$R_a$, —S(O)$_mR_a$, —S(O)$_mOR_a$, —S(O)$_mNR_bR_c$, —N($R_b$)—S(O)$_m$—$R_a$, —N($R_b$)—S(O)$_m$—$R_bR_c$, —N($R_b$)—C(O)$OR_a$, —N($R_b$)—C(S)$OR_a$, —O—$C_{1-6}$ alkylene-$OR_a$, —C(O)—$C_{1-6}$ alkylene-$NR_bR_c$, —N($R_b$)—C(O)—$NR_bR_c$, —N($R_b$)—C(S)—$NR_bR_c$, —O—C(O)—$NR_bR_c$ or —O—C(S)—$NR_bR_c$;

$R_a$, $R_b$ and $R_c$ are each further optionally substituted by one or more groups consisting of the following:

$C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl.

⎓

In a specific embodiment, ⎓ indicates a single bond; in another specific embodiment, ⎓ indicates a double bond.

$A_1$, $A_2$ and $A_3$

In a specific embodiment, $A_1$ is $CR_5$; in another specific embodiment, $A_1$ is CH; in another specific embodiment, $A_1$ is C(OMe); in another specific embodiment, $A_1$ is CF; in another specific embodiment, $A_1$ is N.

In a specific embodiment, $A_2$ is $CR_6$; in another specific embodiment, $A_2$ is CH; in another specific embodiment, $A_2$ is CF; in another specific embodiment, $A_2$ is CMe; in another specific embodiment, $A_2$ is N.

In a specific embodiment, $A_3$ is $CR_7$; in another specific embodiment, $A_3$ is CH; in another specific embodiment, $A_3$ is CMe; in another specific embodiment, $A_3$ is CF; in another specific embodiment, $A_3$ is N.

$R_1$

In a specific embodiment, $R_1$ is H; in another specific embodiment, $R_1$ is D; in another specific embodiment, $R_1$ is halogen; in another specific embodiment, $R_1$ is —CN; in another specific embodiment, $R_1$ is —$OR_a$; in another specific embodiment, $R_1$ is —$SR_a$; in another specific embodiment, $R_1$ is —$NR_bR_c$; in another specific embodiment, $R_1$ is —C(O)$R_a$; in another specific embodiment, $R_1$ is —C(O) $OR_a$; in another specific embodiment, $R_1$ is —C(O)$NR_bR_c$; in another specific embodiment, $R_1$ is $C_{1-6}$ alkyl; in another specific embodiment, $R_1$ is Me; in another specific embodiment, $R_1$ is $C_{1-6}$ haloalkyl; in another specific embodiment, $R_1$ is $C_{3-7}$ cycloalkyl; in another specific embodiment, $R_1$ is 3- to 7-membered heterocyclyl; in another specific embodiment, $R_1$ is $C_{6-10}$ aryl; in another specific embodiment, $R_1$ is 5- to 10-membered heteroaryl.

In the above-mentioned specific embodiments of $R_1$, the $C_{3-7}$ cycloalkyl or 3- to 7-membered heterocyclyl is optionally substituted with oxo; in the above-mentioned specific embodiments of $R_1$, the $C_{3-7}$ cycloalkyl or 3- to 7-membered heterocyclyl is optionally substituted with thioxo.

$R_2$

In a specific embodiment, $R_2$ is H; in another specific embodiment, $R_2$ is D; in another specific embodiment, $R_2$ is halogen; in another specific embodiment, $R_2$ is —CN; in another specific embodiment, $R_2$ is $C_{1-6}$ alkyl; in another specific embodiment, $R_2$ is $C_{1-6}$ haloalkyl; in another specific embodiment, $R_2$ is $C_{3-7}$ cycloalkyl; in another specific embodiment, $R_2$ is 3- to 7-membered heterocyclyl; in another specific embodiment, $R_2$ is $C_{6-10}$ aryl; in another specific embodiment, $R_2$ is 5- to 10-membered heteroaryl.

In the above-mentioned specific embodiments of $R_2$, the $C_{3-7}$ cycloalkyl or 3- to 7-membered heterocyclyl is optionally substituted with oxo; in the above-mentioned specific embodiments of $R_2$, the $C_{3-7}$ cycloalkyl or 3- to 7-membered heterocyclyl is optionally substituted with thioxo.

$R_3$

In a specific embodiment, $R_3$ is H; in another specific embodiment, $R_3$ is D; in another specific embodiment, $R_3$ is halogen; in another specific embodiment, $R_3$ is —CN; in another specific embodiment, $R_3$ is —$NO_2$; in another specific embodiment, $R_3$ is —$OR_a$; in another specific embodiment, $R_3$ is —$SR_a$; in another specific embodiment, $R_3$ is —$NR_bR_c$; in another specific embodiment, $R_3$ is —C(O)$R_a$; in another specific embodiment, $R_3$ is —C(O)$OR_a$; in another specific embodiment, $R_3$ is —C(O)$NR_bR_c$; in another specific embodiment, $R_3$ is —$S(O)_mR_a$; in another specific embodiment, $R_3$ is —$S(O)_mOR_a$; in another specific embodiment, $R_3$ is —$S(O)_mNR_bR_c$; in another specific embodiment, $R_3$ is —O—$C_{1-6}$ alkylene-$R_8$; in another specific embodiment, $R_3$ is $C_{1-6}$ alkyl; in another specific embodiment, $R_3$ is $C_{1-6}$ haloalkyl; in another specific embodiment, $R_3$ is $C_{3-7}$ cycloalkyl; in another specific embodiment, $R_3$ is 3- to 11-membered heterocyclyl; in another specific embodiment, $R_3$ is 3- to 9-membered heterocyclyl; in another specific embodiment, $R_3$ is 4- to 7-membered heterocyclyl; in another specific embodiment, $R_3$ is 5- to 6-membered heterocyclyl; in another specific embodiment, $R_3$ is piperazinyl or morpholinyl; in another specific embodiment, $R_3$ is piperazinyl; in another specific embodiment, $R_3$ is $C_{6-10}$ aryl; in another specific embodiment, $R_3$ is 5- to 10-membered heteroaryl.

In the above-mentioned specific embodiments of $R_3$, the group is optionally substituted with 1, 2, 3, 4 or 5 $R_8$ groups. In a specific embodiment, the group is optionally substituted with 1 $R_8$ group; in another specific embodiment, the group is optionally substituted with 2 $R_8$ groups; in another specific embodiment, the group is optionally substituted with 3 $R_8$ groups; in another specific embodiment, the group is optionally substituted with 4 $R_8$ groups; in another specific embodiment, the group is optionally substituted with 5 $R_8$ groups.

In a more specific embodiment, $R_3$ is selected from the following groups optionally substituted with 1, 2, 3, 4 or 5 $R_8$ groups:

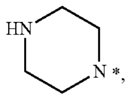, 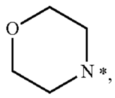, 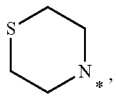, 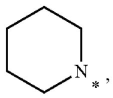, 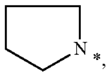, 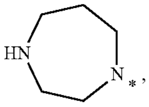, 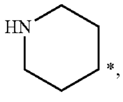, 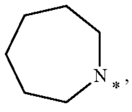, 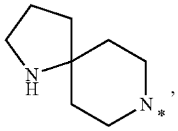, 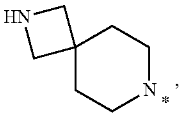, 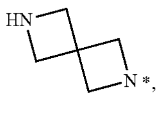, 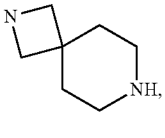, 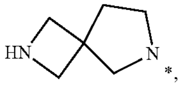, -continued

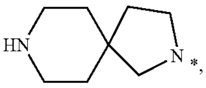, 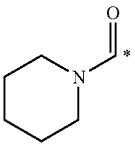, 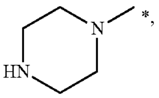, 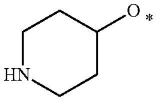 or 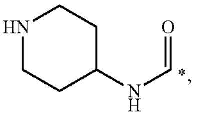, where * denotes the position to be connected.

In a more specific embodiment, $R_3$ is selected from the following groups:

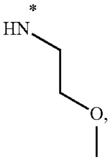, 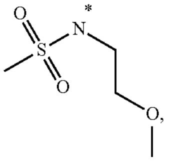, 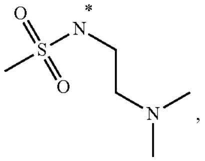, 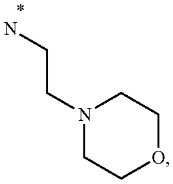, 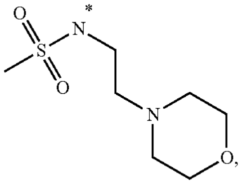, 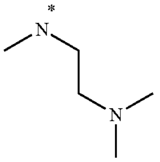, 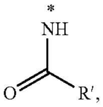, 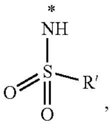, 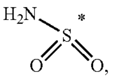, 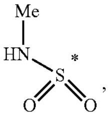, 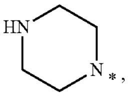, 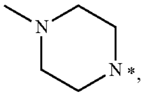, 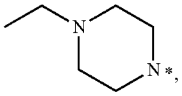, 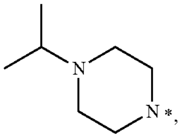, 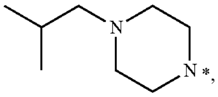, 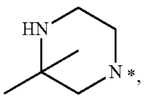, 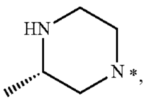, 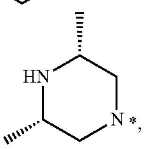, 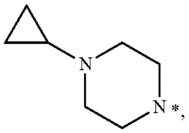, 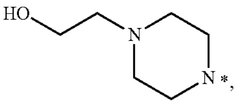, -continued
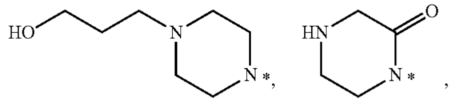
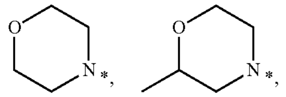
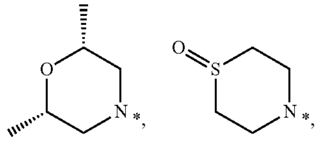
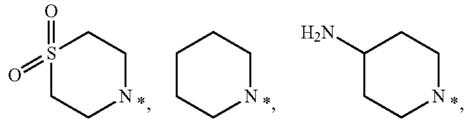
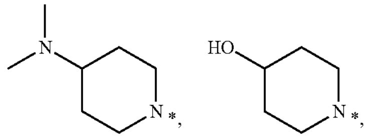
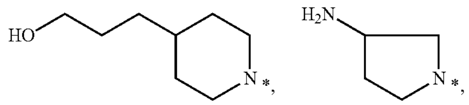
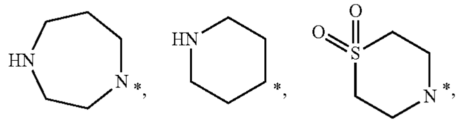
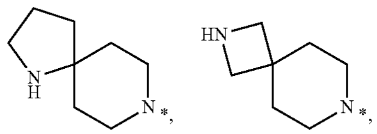
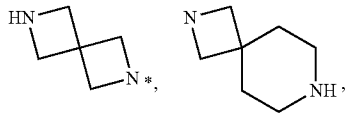
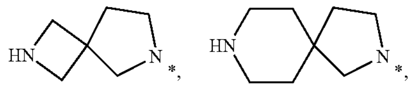
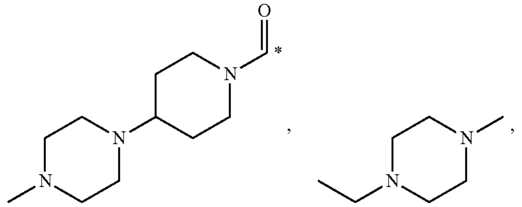
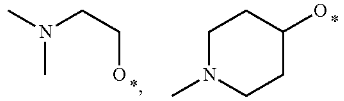
or
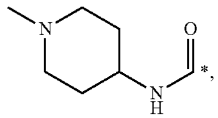
where * denotes the position to be connected;
In a more specific embodiment, $R_3$ is selected from the Mowing groups:
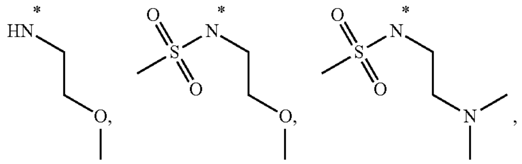
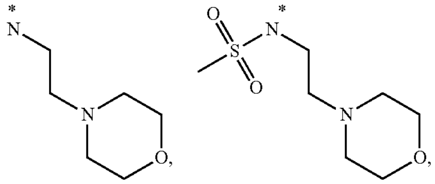
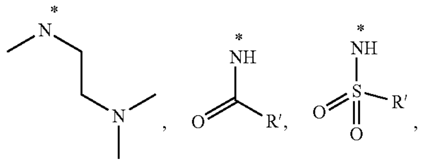
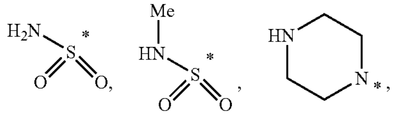
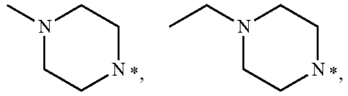
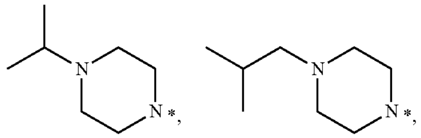
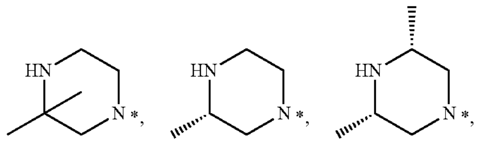
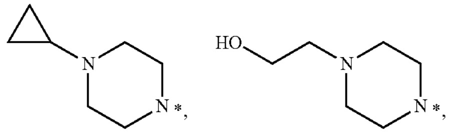
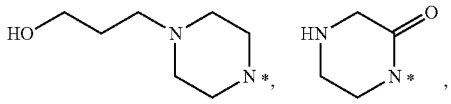
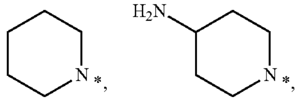
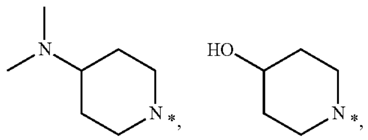
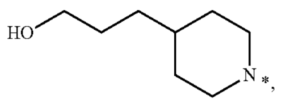
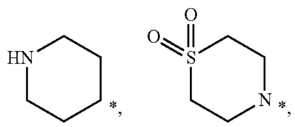

-continued

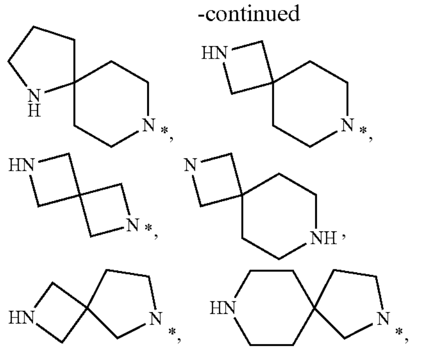

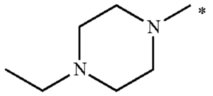

or

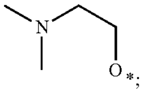

where * denotes the position to be connected.

$R_4$

In a specific embodiment, $R_4$ is H; in another specific embodiment, $R_4$ is —C(O)$R_a$; in another specific embodiment, $R_4$ is —C(O)O$R_a$; in another specific embodiment, $R_4$ is —C(O)N$R_bR_c$; in another specific embodiment, $R_4$ is $C_{1-6}$ alkyl; in another specific embodiment, $R_4$ is $C_{1-6}$ haloalkyl; in another specific embodiment, $R_4$ is $C_{3-7}$ cycloalkyl; in another specific embodiment, $R_4$ is 3- to 7-membered heterocyclyl; in another specific embodiment, $R_4$ is $C_{6-10}$ aryl; in another specific embodiment, $R_4$ is 5- to 10-membered heteroaryl; in another specific embodiment, $R_4$ is isopropyl, isobutyl or cyclopentyl.

L

In a specific embodiment, L is a chemical bond; in another specific embodiment, L is —O—; in another specific embodiment, L is —NH—; in another specific embodiment, L is —C(O)—; in another specific embodiment, L is —C(O)NH—; in another specific embodiment, L is —NHC(O)—; in another specific embodiment, L is —$C_{1-6}$ alkylene-; in another specific embodiment, L is —$C_{2-6}$ alkenylene-; in another specific embodiment, L is —$C_{2-6}$ alkynylene-.

$R_5$

In a specific embodiment, $R_5$ is H; in a specific embodiment, $R_5$ is D; in a specific embodiment, $R_5$ is halogen; in a specific embodiment, $R_5$ is —CN; in a specific embodiment, $R_5$ is —O$R_a$; in a specific embodiment, $R_5$ is —S$R_a$; in a specific embodiment, $R_5$ is —N$R_bR_c$; in a specific embodiment, $R_5$ is —C(O)$R_a$; in a specific embodiment, $R_5$ is —C(O)O$R_a$; in a specific embodiment, $R_5$ is —C(O)N$R_bR_c$; in a specific embodiment, $R_5$ is —S$(O)_m R_a$; in a specific embodiment, $R_5$ is —S$(O)_m$O$R_a$; in a specific embodiment, $R_5$ is —S$(O)_m$N$R_bR_c$; in another specific embodiment, $R_5$ is $C_{1-6}$ alkyl; in another specific embodiment, $R_5$ is $C_{1-6}$ haloalkyl.

$R_6$

In a specific embodiment, $R_6$ is H; in a specific embodiment, $R_6$ is D; in a specific embodiment, $R_6$ is halogen; in a specific embodiment, $R_6$ is —CN; in a specific embodiment, $R_6$ is —O$R_a$; in a specific embodiment, $R_6$ is —S$R_a$; in a specific embodiment, $R_6$ is —N$R_bR_c$; in a specific embodiment, $R_6$ is —C(O)$R_a$; in a specific embodiment, $R_6$ is —C(O)O$R_a$; in a specific embodiment, $R_6$ is —C(O)N$R_bR_c$; in a specific embodiment, $R_6$ is —S$(O)_m R_a$; in a specific embodiment, $R_6$ is —S$(O)_m$O$R_a$; in a specific embodiment, $R_6$ is —S$(O)_m$N$R_bR_c$; in another specific embodiment, $R_6$ is $C_{1-6}$ alkyl; in another specific embodiment, $R_6$ is $C_{1-6}$ haloalkyl.

$R_7$

In a specific embodiment, $R_7$ is H; in a specific embodiment, $R_7$ is D; in a specific embodiment, $R_7$ is halogen; in a specific embodiment, $R_7$ is F; in a specific embodiment, $R_7$ is —CN; in a specific embodiment, $R_7$ is —O$R_a$; in a specific embodiment, $R_7$ is —S$R_a$; in a specific embodiment, $R_7$ is —N$R_bR_c$; in a specific embodiment, $R_7$ is —C(O)$R_a$; in a specific embodiment, $R_7$ is —C(O)O$R_a$; in a specific embodiment, $R_7$ is —C(O)N$R_bR_c$; in a specific embodiment, $R_7$ is —S$(O)_m R_a$; in a specific embodiment, $R_7$ is —S$(O)_m$O$R_a$; in a specific embodiment, $R_7$ is —S$(O)_m$ N$R_bR_c$; in another specific embodiment, $R_7$ is $C_{1-6}$ alkyl; in another specific embodiment, $R_7$ is $C_{1-6}$ haloalkyl.

$R_8$

In a specific embodiment, $R_8$ is H; in a specific embodiment, $R_8$ is D; in another specific embodiment, $R_8$ is —$NH_2$; in another specific embodiment, $R_8$ is —NH$C_{1-6}$ alkyl; in another specific embodiment, $R_8$ is —N$(C_{1-6}$ alkyl$)_2$; in another specific embodiment, $R_8$ is $C_{1-6}$ alkyl; in another specific embodiment, $R_8$ is $C_{1-6}$ haloalkyl; in another specific embodiment, $R_8$ is —$C_{0-6}$ alkylene-O$R_a$; in another specific embodiment, $R_8$ is $C_{3-7}$ cycloalkyl; in another specific embodiment, $R_8$ is 3- to 7-membered heterocyclyl; in another specific embodiment, $R_8$ is $C_{6-10}$ aryl; in another specific embodiment, $R_8$ is 5- to 10-membered heteroaryl; in another specific embodiment, two $R_8$ on the same carbon atom are taken together to form oxo. In another specific embodiment, two $R_8$ on the same carbon atom are taken together to form thioxo.

m

In a specific embodiment, m is 0; in another specific embodiment, m is 1; in another specific embodiment, m is 2.

Any technical solution in any one of the above embodiments, or any combination thereof, may be combined with any technical solution in any one of the above embodiments, or any combination thereof. For example, any technical solution of $A_1$, or any combination thereof, may be combined with any technical solution of $A_2$, $A_3$, $R_1$-$R_8$, R', $R_a$, $R_b$, $R_c$, L, and n, etc or any combination thereof. The present disclosure is intended to include all combination of such technical solutions, which are not exhaustively listed here to save space.

In a specific embodiment, the present disclosure provides compounds of the following general formulae:

(I-1)

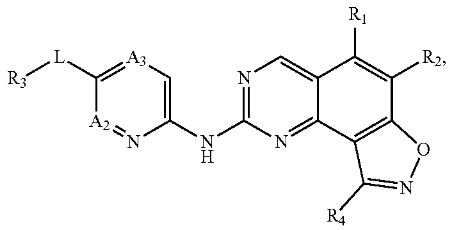

(I-1-1)

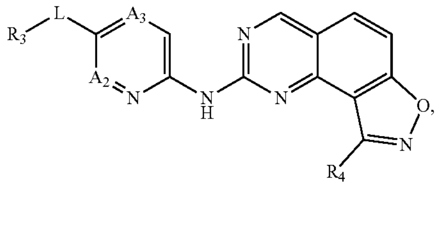

-continued (I-1-2)

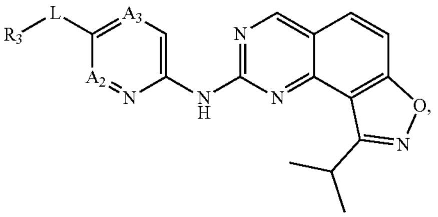

(I-2)

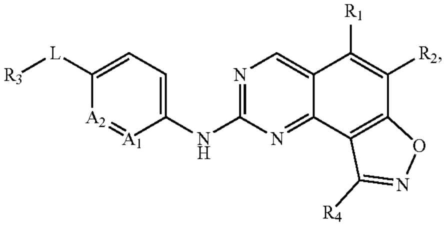

(I-2-1)

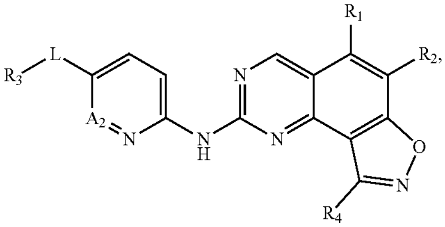

(I-2-2)

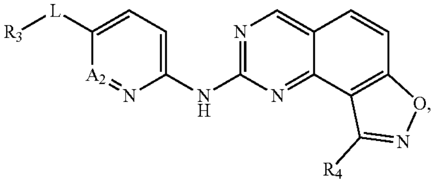

(I-2-3)

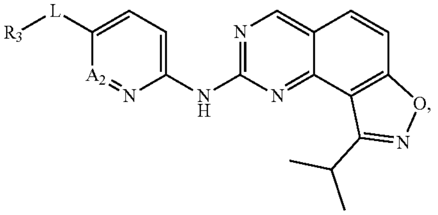

(I-3)

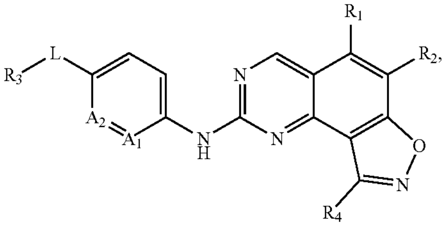

(I-3-1)

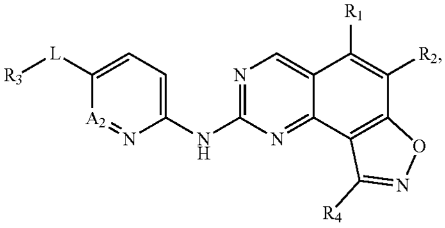

-continued (I-3-2)

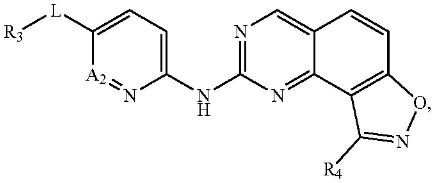

(I-3-3)

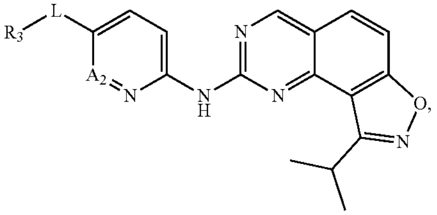

(I-4)

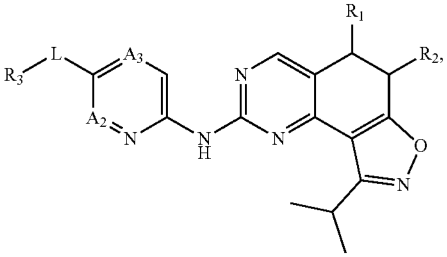

(I-4-1)

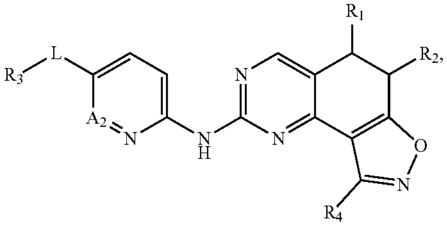

(I-4-2)

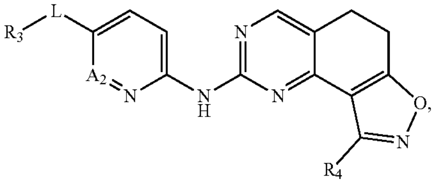

and (I-4-3)

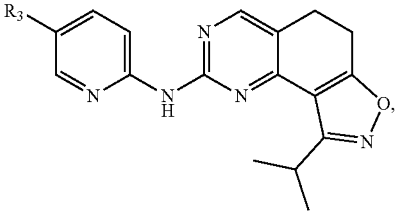

wherein each group is as defined above.

In a more specific embodiment, the present disclosure provides a compound of formula (I), or a pharmaceutically acceptable salt, an enantiomer, a diastereomer, a racemate, a solvate, a hydrate, a polymorph, a prodrug, or an isotope variant thereof, and mixtures thereof, wherein, ═ represents a double bond.

In a more specific embodiment, the present disclosure provides a compound of formula (I), or a pharmaceutically acceptable salt, an enantiomer, a diastereomer, a racemate, a solvate, a hydrate, a polymorph, a prodrug, or an isotope variant thereof, and mixtures thereof, wherein, $A_1$ is N.

In a more specific embodiment, the present disclosure provides a compound of formula (I), or a pharmaceutically acceptable salt, an enantiomer, a diastereomer, a racemate, a solvate, a hydrate, a polymorph, a prodrug, or an isotope variant thereof, and mixtures thereof, wherein, $A_1$ is $CR_5$.

In a more specific embodiment, the present disclosure provides a compound of formula (I), or a pharmaceutically acceptable salt, an enantiomer, a diastereomer, a racemate, a solvate, a hydrate, a polymorph, a prodrug, or an isotope variant thereof, and mixtures thereof, wherein, $A_2$ is $CR_6$.

In a more specific embodiment, the present disclosure provides a compound of formula (I), or a pharmaceutically acceptable salt, an enantiomer, a diastereomer, a racemate, a solvate, a hydrate, a polymorph, a prodrug, or an isotope variant thereof, and mixtures thereof, wherein, $A_3$ is CH.

In a more specific embodiment, the present disclosure provides a compound of formula (I), or a pharmaceutically acceptable salt, an enantiomer, a diastereomer, a racemate, a solvate, a hydrate, a polymorph, a prodrug, or an isotope variant thereof, and mixtures thereof, wherein, $R_1$ is selected from H, D, halogen, —CN, $C_{1-6}$ alkyl or $C_{1-6}$ haloalkyl; alternatively, $R_1$ is H or D.

In a more specific embodiment, the present disclosure provides a compound of formula (I), or a pharmaceutically acceptable salt, an enantiomer, a diastereomer, a racemate, a solvate, a hydrate, a polymorph, a prodrug, or an isotope variant thereof, and mixtures thereof, wherein, $R_2$ is selected from H, D, halogen, —CN, $C_{1-6}$ alkyl or $C_{1-6}$ haloalkyl; alternatively, $R_2$ is H or D.

In a more specific embodiment, the present disclosure provides a compound of formula (I), or a pharmaceutically acceptable salt, an enantiomer, a diastereomer, a racemate, a solvate, a hydrate, a polymorph, a prodrug, or an isotope variant thereof, and mixtures thereof, wherein, $R_3$ is selected from H, D, halogen, —CN, —$NO_2$, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, —O—$C_{1-6}$ alkylene-$R_8$, $C_{1-6}$ alkyl, $C_{1-6}$ haloalkyl, $C_{3-7}$ cycloalkyl, 3- to 11-membered heterocyclyl, $C_{6-10}$ aryl, or 5- to 10-membered heteroaryl, each of which is optionally substituted by 1, 2, 3, 4, or 5 $R_8$ groups;

alternatively, $R_3$ is selected from H, D, halogen, —CN, —$NO_2$, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, —O—$C_{1-6}$ alkylene-$R_8$, $C_{1-6}$ alkyl, $C_{1-6}$ haloalkyl, $C_{3-7}$ cycloalkyl or 4- to 7-membered heterocyclyl, the said group is optionally substituted with 1, 2 or 3 $R_8$ groups;

alternatively, $R_3$ is selected from H, D, halogen, —CN, —$NO_2$, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, —O—$C_{1-6}$ alkylene-$R_8$, $C_{1-6}$ alkyl, $C_{1-6}$ haloalkyl, $C_{3-7}$ cycloalkyl or 5- to 6-membered heterocyclyl, the said group is optionally substituted with 1 or 2 $R_8$ groups;

alternatively, $R_3$ is selected from H, D, —$OR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, —O—$C_{1-6}$ alkylene-$R_8$, $C_{4-6}$ cycloalkyl or 5- to 6-membered heterocyclyl, the said group is optionally substituted with 1 $R_8$ group;

alternatively, $R_3$ is selected from H, D, —$OR_a$, —$NR_bR_c$, —$C(O)R_a$, —$C(O)OR_a$, —$C(O)NR_bR_c$, —$S(O)_mR_a$, —$S(O)_mOR_a$ or —$S(O)_mNR_bR_c$, or the following groups optionally substituted with 1, 2, 3, 4 or 5 $R_8$ groups:

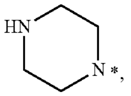
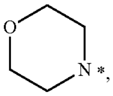
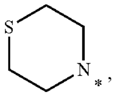
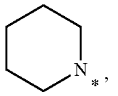
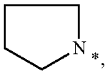
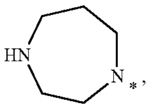
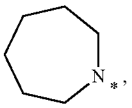
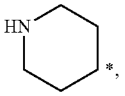
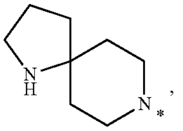
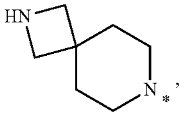
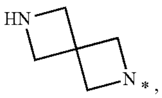
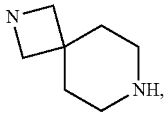
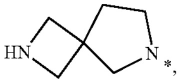
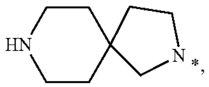
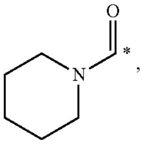
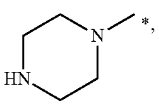
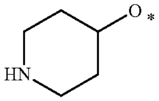
or
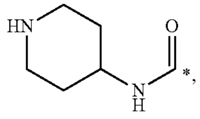

where * denotes the position to be connected;

alternatively, $R_3$ is selected from the following groups:

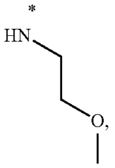
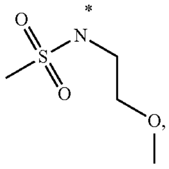
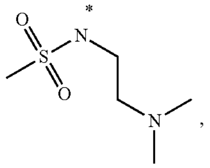
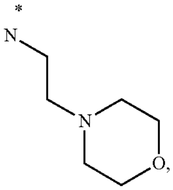
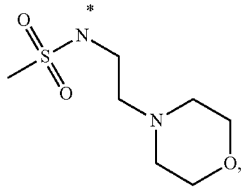
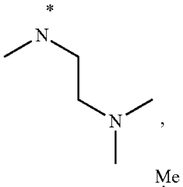
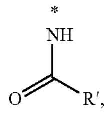
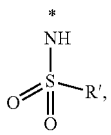
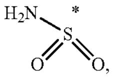
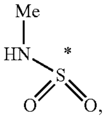
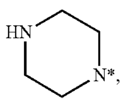
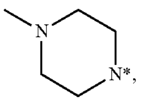
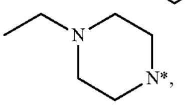

-continued
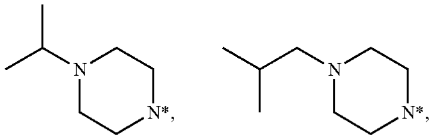
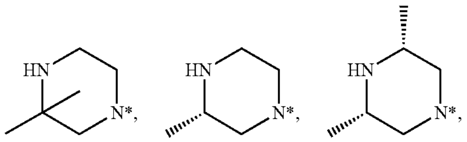
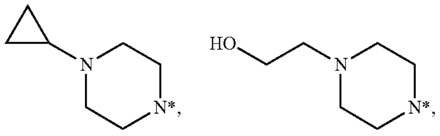
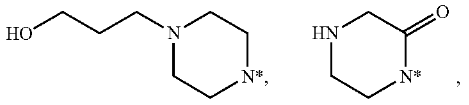
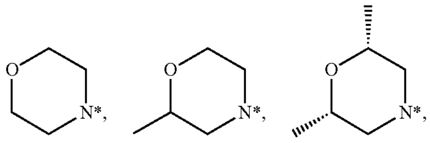
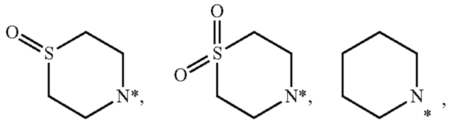
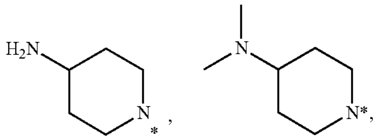
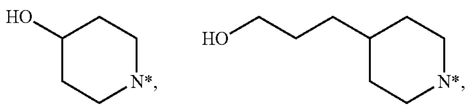
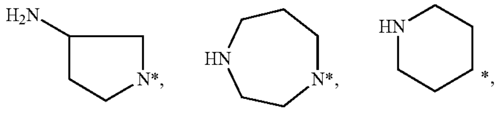
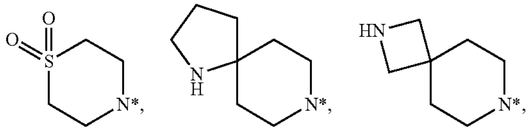
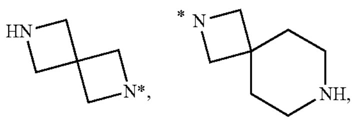
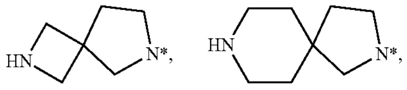
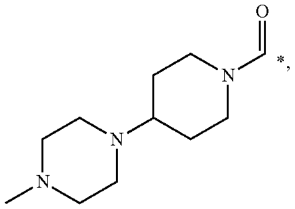
-continued
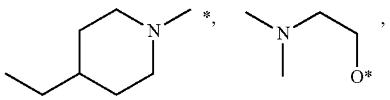
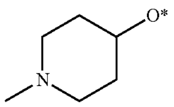
or
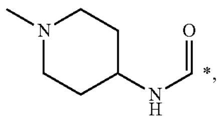
where * denotes the position to be connected; alternatively, $R_3$ is selected from the following groups:
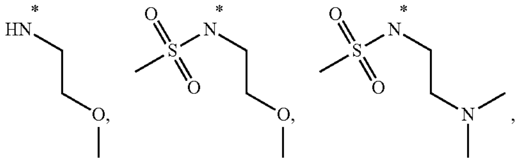
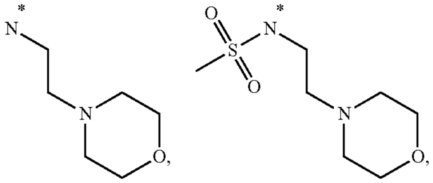
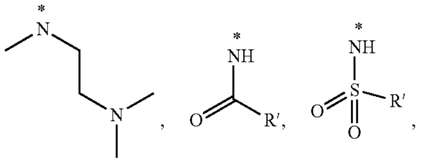
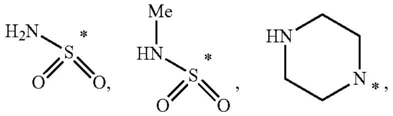
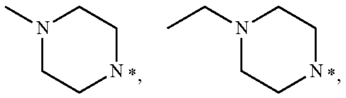
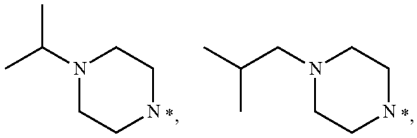
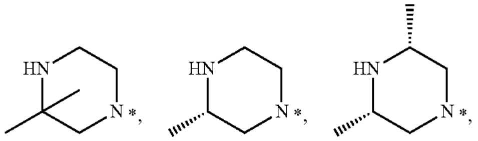
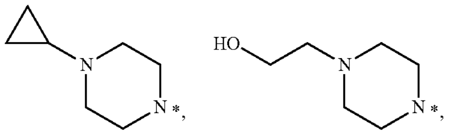
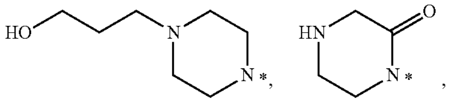
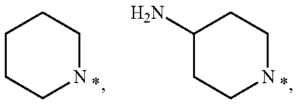

-continued

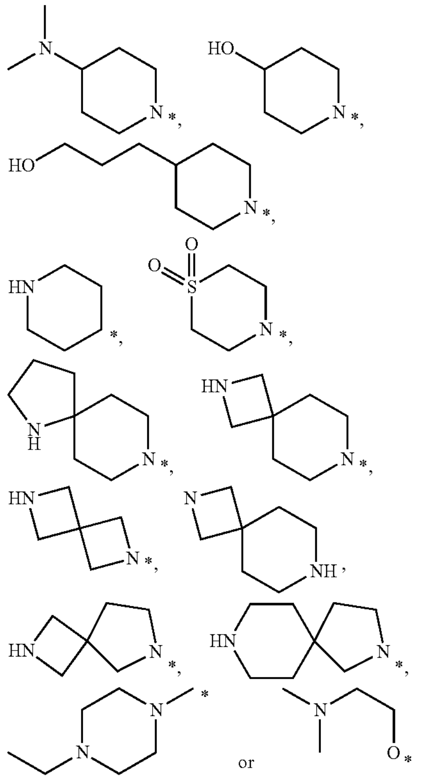

where * denotes the position to be connected.

In a more specific embodiment, the present disclosure provides a compound of formula (I), or a pharmaceutically acceptable salt, an enantiomer, a diastereomer, a racemate, a solvate, a hydrate, a polymorph, a prodrug, or an isotope variant thereof, and mixtures thereof, wherein, $R_4$ is selected from H, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl;

alternatively, $R_4$ is selected from He $C_{1-6}$ alkyl, $C_{1-6}$ haloalkyl, $C_{3-7}$ cycloalkyl or 3- to 7-membered heterocyclyl;

alternatively, $R_4$ is selected from $C_{1-6}$ alkyl, $C_{1-6}$ haloalkyl, $C_{3-7}$ cycloalkyl or 3- to 7-membered heterocyclyl.

In a more specific embodiment, the present disclosure provides a compound of formula (I), or a pharmaceutically acceptable salt, an enantiomer, a diastereomer, a racemate, a solvate, a hydrate, a polymorph, a prodrug, or an isotope variant thereof, and mixtures thereof, wherein, L is a chemical bond.

In a more specific embodiment, the present disclosure provides a compound of formula (I), or a pharmaceutically acceptable salt, an enantiomer, a diastereomer, a racemate, a solvate, a hydrate, a polymorph, a prodrug, or an isotope variant thereof, and mixtures thereof, wherein, $R_5$, $R_6$ and $R_7$ are independently selected from H, D, halogen, —CN, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, $C_{1-6}$ alkyl or $C_{1-6}$ haloalkyl; alternatively, wherein $R_5$ is selected from H, D, halogen, —CN, -$or_a$, -$sr_a$, -$nr_br_c$, $C_{1-6}$ alkyl or $C_{1-6}$ haloalkyl;

alternatively, $R_5$, $R_6$ and $R_7$ are independently selected from H, D, halogen, —$C(O)R_a$, —$C(O)or_a$, —$C(O)_nr_br_c$, —$S(O)_mr_a$, —$S(O)_m$ $or_a$ or —$S(O)_mnr_br_c$; alternatively, wherein $R_5$ is selected from H or D;

alternatively, $R_5$, $R_6$ and $R_7$ are independently selected from H, halogen, —CN, -$or_a$, -$sr_a$, -$nr_br_c$, $C_{1-6}$ alkyl or $C_{1-6}$ haloalkyl; alternatively, wherein $R_5$ is selected from H or D;

alternatively, $R_5$, $R_6$ and $R_7$ are independently selected from H, halogen, —CN, —$OR_a$, $C_{1-6}$ alkyl or $C_{1-6}$ haloalkyl; alternatively, $R_5$, $R_6$ and $R_7$ are independently selected from H or D;

alternatively, $R_7$ is H.

In a more specific embodiment, the present disclosure provides a compound of formula (I), or a pharmaceutically acceptable salt, an enantiomer, a diastereomer, a racemate, a solvate, a hydrate, a polymorph, a prodrug, or an isotope variant thereof, and mixtures thereof, wherein, $R_8$ is selected from H, D, —$NH_2$, —$NHC_{1-6}$ alkyl, —$N(C_{1-6}$ alkyl$)_2$, $C_{1-6}$ alkyl, $C_{1-6}$ haloalkyl, —$C_{0-6}$ alkylene-$OR_a$, $C_{3-7}$ cycloalkyl or 3- to 7-membered heterocyclyl; or two $R_8$ on the same atom are taken together to form oxo or thioxo;

alternatively, $R_8$ is selected from H, —$NH_2$, —$NHC_{1-6}$ alkyl, —$N(C_{1-6}$ alkyl$)_2$, $C_{1-6}$ alkyl, $C_{1-6}$ haloalkyl or —$C_{0-6}$ alkylene-$or_a$; or two $R_8$ on the same atom are taken together to form oxo or thioxo;

alternatively, $R_8$ is selected from H, D, —$NH_2$, —$NHC_{1-6}$ alkyl, —$N(C_{1-6}$ alkyl$)_2$, $C_{1-6}$ alkyl or $C_{1-6}$ haloalkyl; or two $R_8$ on the same atom are taken together to form oxo or thioxo;

alternatively, $R_8$ is selected from H, D, $C_{1-6}$ alkyl or $C_{1-6}$ haloalkyl.

In a more specific embodiment, the present disclosure provides a compound of formula (I-1), or a pharmaceutically acceptable salt, an enantiomer, a diastereomer, a racemate, a solvate, a hydrate, a polymorph, a prodrug, or an isotope variant thereof, and mixtures thereof:

(I-1)

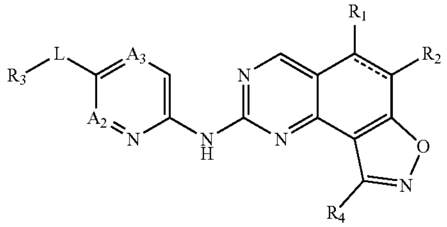

wherein each group is as defined above;

alternatively, which is a compound of general formula (I-1-1):

(I-1-1)

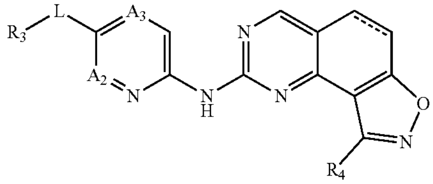

wherein,

⎓ indicates a single bond or a double bond;

$A_2$ is selected from $CR_6$ or N;

$A_3$ is $CR_7$;

L is selected from a chemical bond, —O—, —NH—, —C(O)— or —$C_{1-6}$ alkylene-;

$R_3$ is selected from H, halogen, —CN, $C_{1-6}$ alkyl, $C_{1-6}$ haloalkyl, $C_{3-7}$ cycloalkyl or 3- to 11-membered heterocyclyl, the said group is optionally substituted with 1, 2 or 3 $R_8$ groups; alternatively, $R_3$ is 5- to 6-membered heterocyclyl containing at least one N atom, which is optionally substituted with 1 or 2 $R_8$ groups; alternatively, $R_3$ is piperazinyl, morpholinyl, thiomorpholinyl or piperidinyl, which is optionally substituted with 1 or 2 $R_8$ groups;

$R_4$ is selected from H, $C_{1-6}$ alkyl, $C_{1-6}$ haloalkyl, $C_{3-7}$ cycloalkyl or 3- to 7-membered heterocyclyl;

$R_6$ is selected from H, halogen, —CN, $C_{1-6}$ alkyl or $C_{1-6}$ haloalkyl;

$R_7$ is selected from H, halogen, —CN, $C_{1-6}$ alkyl or $C_{1-6}$ haloalkyl;

$R_8$ is selected from H, —$NH_2$, —$NHC_{1-6}$ alkyl, —$N(C_{1-6}$ alkyl$)_2$, $C_{1-6}$ alkyl, $C_{1-6}$ haloalkyl, —$C_{0-6}$ alkylene-$OR_a$, $C_{3-7}$ cycloalkyl or 3- to 7-membered heterocyclyl; or two $R_8$ on the same atom are taken together to form oxo or thioxo;

alternatively, which is a compound of general formula (I-1-1):

(I-1-1)

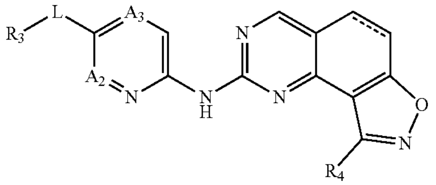

wherein, $\overline{\cdots}$ indicates a single bond or a double bond;

$A_2$ is selected from $CR_6$ or N;

$A_3$ is $CR_7$;

L is selected from a chemical bond or $CH_2$;

$R_3$ is 5- to 6-membered heterocyclyl, which is optionally substituted with 1 or 2 $R_8$ groups; alternatively, the 5- to 6-membered heterocyclyl is piperazinyl, morpholinyl, thiomorpholinyl or piperidinyl;

$R_4$ is selected from iPr, iBu or cyclopentyl;

$R_6$ is H or Me;

$R_7$ is H or Me;

$R_8$ is selected from H, Me, Et, iPr, iBu, $NEt_2$, oxo or cyclopropyl.

In a more specific embodiment, the present disclosure provides a compound of formula (I-2), or a pharmaceutically acceptable salt, an enantiomer, a diastereomer, a racemate, a solvate, a hydrate, a polymorph, a prodrug, or an isotope variant thereof, and mixtures thereof:

(I-2)

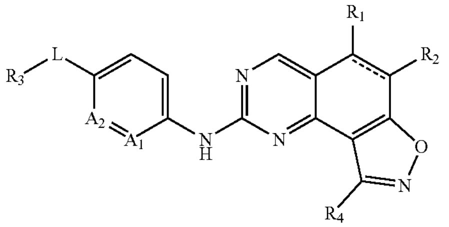

wherein each group is as defined above;

alternatively, which is a compound of general formula (I-2-1):

(I-2-1)

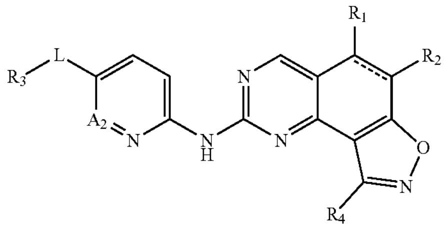

wherein each group is as defined above;

alternatively, which is a compound of general formula (I-2-2):

(I-2-2)

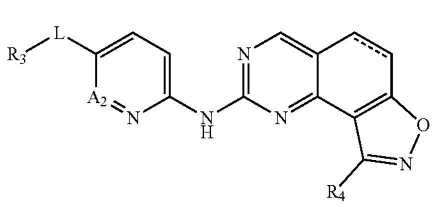

wherein, $\overline{\cdots}$ indicates a single bond or a double bond;

$A_2$ is selected from $CR_6$ or N;

L is selected from a chemical bond, —O—, —NH—, —C(O)— or —$C_{1-6}$ alkylene-;

$R_3$ is selected from H, halogen, —CN, $C_{1-6}$ alkyl, $C_{1-6}$ haloalkyl, $C_{3-7}$ cycloalkyl or 3- to 11-membered heterocyclyl, the said group is optionally substituted with 1, 2 or 3 $R_8$ groups; alternatively, $R_3$ is 5- to 6-membered heterocyclyl containing at least one N atom, which is optionally substituted with 1 or 2 $R_8$ groups; alternatively, $R_3$ is piperazinyl, morpholinyl, thiomorpholinyl or piperidinyl, which is optionally substituted with 1 or 2 $R_8$ groups;

$R_4$ is selected from H, $C_{1-6}$ alkyl, $C_{1-6}$ haloalkyl, $C_{3-7}$ cycloalkyl or 3- to 7-membered heterocyclyl;

$R_6$ is selected from H, halogen, —CN, $C_{1-6}$ alkyl or $C_{1-6}$ haloalkyl;

$R_8$ is selected from H, —$NH_2$, —$NHC_{1-6}$ alkyl, —$N(C_{1-6}$ alkyl$)_2$, $C_{1-6}$ alkyl, $C_{1-6}$ haloalkyl, —$C_{0-6}$ alkylene-$OR_a$, $C_{3-7}$ cycloalkyl or 3- to 7-membered heterocyclyl; or two $R_8$ on the same atom are taken together to form oxo or thioxo;

alternatively, which is a compound of general formula (I-2-2):

(I-2-2)

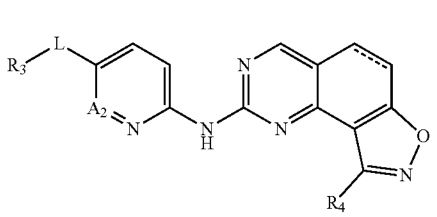

wherein,

⎓ indicates a single bond or a double bond;

$A_2$ is selected from $CR_6$ or N;

L is selected from a chemical bond or $CH_2$;

$R_3$ is 5- to 6-membered heterocyclyl, which is optionally substituted with 1 or 2 $R_8$ groups; alternatively, the 5- to 6-membered heterocyclyl is piperazinyl, morpholinyl, thiomorpholinyl or piperidinyl;

$R_4$ is selected from iPr, iBu or cyclopentyl;

$R_6$ is H or Me;

$R_8$ is selected from H, Me, Et, iPr, iBu, $NEt_2$, oxo or cyclopropyl.

In a more specific embodiment, the present disclosure provides a compound of formula (I-3), or a pharmaceutically acceptable salt, an enantiomer, a diastereomer, a racemate, a solvate, a hydrate, a polymorph, a prodrug, or an isotope variant thereof, and mixtures thereof:

(I-3)

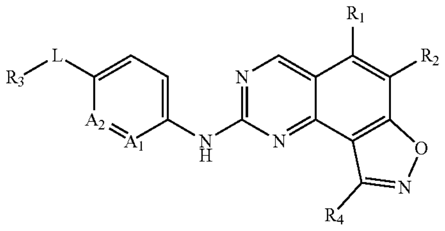

wherein each group is as defined above;

alternatively, which is a compound of general formula (I-3-1):

(I-3-1)

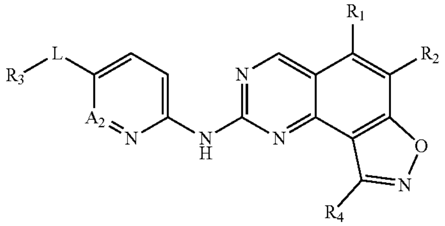

wherein each group is as defined above;

alternatively, which is a compound of general formula (I-3-2):

(I-3-2)

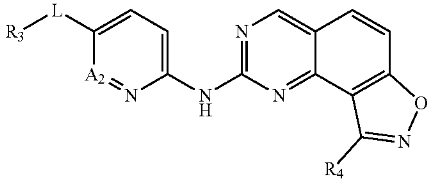

wherein, $A_2$ is selected from $CR_6$ or N;

L is selected from a chemical bond, —O—, —NH—, —C(O)— or —$C_{1-6}$ alkylene-;

$R_3$ is selected from H, halogen, —CN, $C_{1-6}$ alkyl, $C_{1-6}$ haloalkyl, $C_{3-7}$ cycloalkyl or 3- to 11-membered heterocyclyl, the said group is optionally substituted with 1, 2 or 3 $R_8$ groups; alternatively, $R_3$ is 5- to 6-membered heterocyclyl containing at least one N atom, which is optionally substituted with 1 or 2 $R_8$ groups; alternatively, $R_3$ is piperazinyl or piperidinyl, which is optionally substituted with 1 or 2 $R_8$ groups;

$R_4$ is selected from H, $C_{1-6}$ alkyl, $C_{1-6}$ haloalkyl, $C_{3-7}$ cycloalkyl or 3- to 7-membered heterocyclyl;

$R_6$ is selected from H, halogen or —CN;

$R_8$ is selected from H, —$NH_2$, —$NHC_{1-6}$ alkyl, —$N(C_{1-6}$ alkyl$)_2$, $C_{1-6}$ alkyl, $C_{1-6}$ haloalkyl or —$C_{0-6}$ alkylene-$OR_a$; or two $R_8$ on the same atom are taken together to form oxo or thioxo;

alternatively, which is a compound of general formula (I-3-2):

(I-3-2)

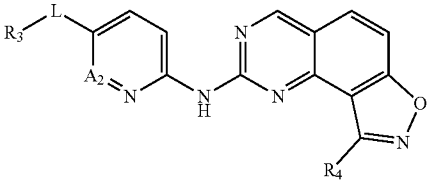

wherein, $A_2$ is selected from $CR_6$ or N;

L is selected from a chemical bond or $CH_2$;

$R_3$ is 5- to 6-membered heterocyclyl, the said group is optionally substituted with 1 or 2 $R_8$ groups; alternatively, the 5- to 6-membered heterocyclyl is piperazinyl or piperidinyl;

$R_4$ is selected from iPr, iBu or cyclopentyl;

$R_6$ is H;

$R_8$ is selected from H, Me, Et, iPr, iBu, $NEt_2$ or oxo.

In a more specific embodiment, the present disclosure provides a compound of formula (I-4), or a pharmaceutically acceptable salt, an enantiomer, a diastereomer, a racemate, a solvate, a hydrate, a polymorph, a prodrug, or an isotope variant thereof, and mixtures thereof:

(I-4)

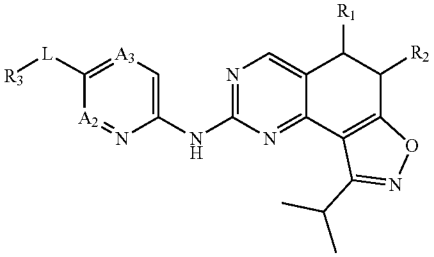

wherein each group is as defined above;

alternatively, which is a compound of general formula (I-4-1):

(I-4-1)

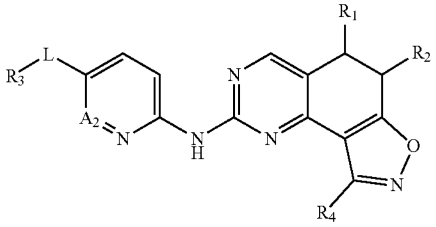

wherein each group is as defined above;

alternatively, which is a compound of general formula (I-4-2):

(I-42-)

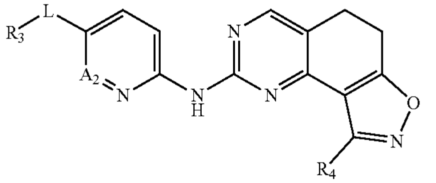

wherein, $A_2$ is selected from $CR_6$ or N;

L is selected from a chemical bond, —O—, —NH—, —C(O)— or —$C_{1-6}$ alkylene-;

$R_3$ is selected from H, halogen, —CN, $C_{1-6}$ alkyl, $C_{1-6}$ haloalkyl, $C_{3-7}$ cycloalkyl or 3- to 11-membered heterocyclyl, the said group is optionally substituted with 1, 2 or 3 $R_8$ groups; alternatively, $R_3$ is 5- to 6-membered heterocyclyl containing at least one N atom, which is optionally substituted with 1 or 2 $R_8$ groups; alternatively, $R_3$ is piperazinyl, morpholinyl, thiomorpholinyl or piperidinyl, which is optionally substituted with 1 or 2 $R_8$ groups;

$R_4$ is selected from H, $C_{1-6}$ alkyl, $C_{1-6}$ haloalkyl, $C_{3-7}$ cycloalkyl or 3- to 7-membered heterocyclyl;

$R_6$ is selected from H, halogen, —CN, $C_{1-6}$ alkyl or $C_{1-6}$ haloalkyl;

$R_8$ is selected from H, —$NH_2$, —$NHC_{1-6}$ alkyl, —N($C_{1-6}$ alkyl)$_2$, $C_{1-6}$ alkyl, $C_{1-6}$ haloalkyl, —$C_{0-6}$ alkylene-$OR_a$, $C_{3-7}$ cycloalkyl or 3- to 7-membered heterocyclyl; or two $R_8$ on the same atom are taken together to form oxo or thioxo;

alternatively, which is a compound of general formula (I-4-3):

(I-4-3)

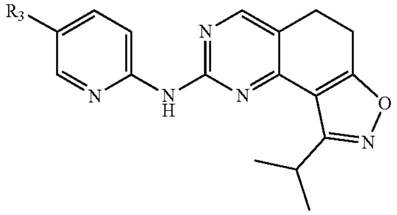

wherein, $R_3$ is 5- to 6-membered heterocyclyl, the said group is optionally substituted with 1 or 2 $R_8$ groups; alternatively, the 5- to 6-membered heterocyclyl is piperazinyl or morpholinyl;

$R_8$ is selected from H or Et.

In a more specific embodiment, the present disclosure provides a compound of formula (I-5) or (I-5-1), or a pharmaceutically acceptable salt, an enantiomer, a diastereomer, a racemate, a solvate, a hydrate, a polymorph, a prodrug, or an isotope variant thereof, and mixtures thereof:

(I-5)

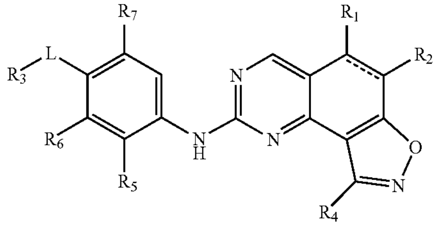

or (I-5-1)

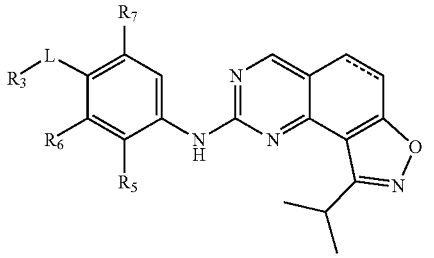

wherein, $\overline{\overline{\phantom{x}}}$ indicates a single bond or a double bond;

$R_1$ is selected from H, D, halogen, —CN, —$OR_a$, $C_{1-6}$ alkyl or $C_{1-6}$ haloalkyl;

$R_2$ is selected from H, D, halogen, —CN, —$OR_a$, $C_{1-6}$ alkyl or $C_{1-6}$ haloalkyl;

$R_3$ is —$NR_bR_c$, —O—$C_{1-6}$ alkylene-$R_8$ or 4- to 7-membered heterocyclyl optionally substituted by 1, 2 or 3 $R_8$ groups;

L is selected from a chemical bond, —C(O)—, —C(O)NH— or —NHC(O)—;

$R_4$ is selected from $C_{1-6}$ alkyl, $C_{1-6}$ haloalkyl, $C_{3-7}$ cycloalkyl or 3- to 7-membered heterocyclyl;

$R_5$ is selected from H, D, halogen, $OR_a$, —$NR_bR_c$, —$S(O)_mR_a$, —$S(O)_mOR_a$ or —$S(O)_mNR_bR_c$;

$R_6$ is selected from H, D, halogen, —$S(O)_mR_a$, —$S(O)_mOR_a$ or —$S(O)_mNR_bR_c$;

$R_7$ is selected from H, D, halogen, —$S(O)_mR_a$, —$S(O)_mOR_a$ or —$S(O)_mNR_bR_c$;

$R_8$ is independently selected from H, D, —$NH_2$, —$NHC_{1-6}$ alkyl, —N($C_{1-6}$ alkyl)$_2$, $C_{1-6}$ alkyl or $C_{1-6}$ haloalkyl;

$R_8$ is optionally substituted with 1, 2 or 3 R groups, wherein the R is independently selected from H, —OH, halogen, —$NO_2$, carbonyl, —CN, —$OR_a$, —$SR_a$ or —$NR_bR_c$;

$R_a$ is independently selected from H, —$NH_2$, —$NHC_{1-6}$ alkyl, —N($C_{1-6}$ alkyl)$_2$, $C_{1-6}$ alkyl or $C_{1-6}$ haloalkyl;

$R_b$ and $R_c$ are independently selected from H, —$C_{0-6}$ alkylene-S(O)$_m$R', $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl or —$C_{0-6}$ alkylene-3- to 7-membered heterocyclyl; or, $R_b$, $R_c$ and N atom are taken together to form 3- to 7-membered heterocyclyl;

R' is independently selected from H, $C_{1-6}$ alkyl, $C_{2-6}$ alkenyl, $C_{2-6}$ alkynyl or $C_{1-6}$ haloalkyl;

m represents 0, 1, or 2.

In a more specific embodiment, the present disclosure provides a compound of formula (I-5) or (I-5-1), or a pharmaceutically acceptable salt, an enantiomer, a diastereomer, a racemate, a solvate, a hydrate, a polymorph, a prodrug, or an isotope variant thereof, and mixtures thereof, wherein, ⎓ indicates a single bond or a double bond;

$R_1$ is selected from H, D, halogen, —CN or —$OR_a$;

$R_2$ is selected from H, D, halogen, —CN or —$OR_a$;

$R_3$ is —$NR_bR_c$, —O—$C_{1-6}$ alkylene-$R_8$ or 5- to 6-membered heterocyclyl optionally substituted by 1 or 2 $R_8$ groups;

L is selected from a chemical bond, —C(O)—, —C(O)NH— or —NHC(O)—;

$R_4$ is selected from $C_{1-6}$ alkyl, $C_{1-6}$ haloalkyl, $C_{3-7}$ cycloalkyl or 3- to 7-membered heterocyclyl;

$R_5$ is selected from H, D, halogen or $OR_a$;

$R_6$ is selected from H, D or halogen;

$R_7$ is selected from H, D or halogen;

$R_8$ is independently selected from H, D, —$NH_2$, —$NHC_{1-6}$ alkyl, —$N(C_{1-6}$ alkyl$)_2$, $C_{1-6}$ alkyl or $C_{1-6}$ haloalkyl;

$R_8$ is optionally substituted with 1, 2 or 3 R groups, wherein the R is independently selected from H, —OH, halogen, —$NO_2$, carbonyl, —CN, —$OR_a$, —$SR_a$ or —$NR_bR_c$;

$R_a$ is independently selected from H, —$NH_2$, —$NHC_{1-6}$ alkyl, —$N(C_{1-6}$ alkyl$)_2$, $C_{1-6}$ alkyl or $C_{1-6}$ haloalkyl;

$R_b$ and $R_c$ are independently selected from H, —$C_{0-6}$ alkylene-$S(O)_mR'$, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl or —$C_{0-6}$ alkylene-3- to 7-membered heterocyclyl; or, $R_b$, $R_c$ and N atom are taken together to form 3- to 7-membered heterocyclyl;

R' is independently selected from H, $C_{1-6}$ alkyl, $C_{2-6}$ alkenyl, $C_{2-6}$ alkynyl or $C_{1-6}$ haloalkyl;

m represents 0, 1, or 2.

In a more specific embodiment, the present disclosure provides a compound of formula (I-5) or (I-5-1), or a pharmaceutically acceptable salt, an enantiomer, a diastereomer, a racemate, a solvate, a hydrate, a polymorph, a prodrug, or an isotope variant thereof, and mixtures thereof, wherein, ⎓ indicates a single bond or a double bond;

$R_1$ is selected from H or D;

$R_2$ is selected from H or D;

$R_3$ is selected from —$NR_bR_c$, —O—$C_{1-6}$ alkylene-$R_8$, piperazinyl or morpholinyl, the said group is optionally substituted with 1 $R_8$ group;

L is selected from a chemical bond or —C(O)—;

$R_4$ is selected from $C_{1-6}$ alkyl or $C_{1-6}$ haloalkyl;

$R_5$ is selected from H, D, F or OMe;

$R_6$ is selected from H, D or F;

$R_7$ is selected from H, D or F;

$R_8$ is independently selected from H, D, —$NH_2$, —$NHC_{1-6}$ alkyl, —$N(C_{1-6}$ alkyl$)_2$, $C_{1-6}$ alkyl or $C_{1-6}$ haloalkyl;

$R_8$ is optionally substituted with 1, 2 or 3 R groups, wherein the R is independently selected from H, —OH, halogen, —$NO_2$, carbonyl, —CN, —$OR_a$, —$SR_a$ or —$NR_bR_c$;

$R_a$ is independently selected from H, $C_{1-6}$ alkyl or $C_{1-6}$ haloalkyl;

$R_b$ and $R_c$ are independently selected from H, —$C_{0-6}$ alkylene-$S(O)_mR'$, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl or —$C_{0-6}$ alkylene-3- to 7-membered heterocyclyl; or, $R_b$, $R_c$ and N atom are taken together to form 3- to 7-membered heterocyclyl;

R' is independently selected from H, $C_{1-6}$ alkyl, $C_{2-6}$ alkenyl, $C_{2-6}$ alkynyl or $C_{1-6}$ haloalkyl;

m represents 0, 1, or 2.

In a more specific embodiment, the present disclosure provides a compound of formula (I-6) or (I-6-1), or a pharmaceutically acceptable salt, an enantiomer, a diastereomer, a racemate, a solvate, a hydrate, a polymorph, a prodrug, or an isotope variant thereof, and mixtures thereof:

(I-6)

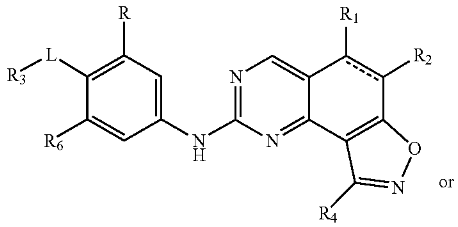

or (I-6-1)

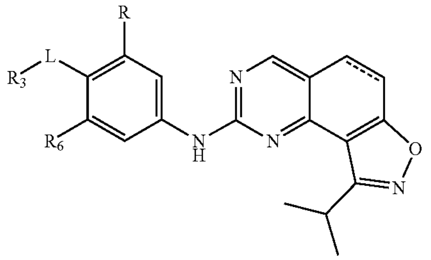

wherein,

⎓ indicates a single bond or a double bond;

$R_1$ is selected from H, D, halogen, —CN, —$OR_a$, $C_{1-6}$ alkyl or $C_{1-6}$ haloalkyl;

$R_2$ is selected from H, D, halogen, —CN, —$OR_a$, $C_{1-6}$ alkyl or $C_{1-6}$ haloalkyl;

$R_3$ is —$NR_bR_c$, —O—$C_{1-6}$ alkylene-$R_8$ or 4- to 7-membered heterocyclyl optionally substituted by 1, 2 or 3 $R_8$ groups;

L is selected from a chemical bond, —C(O)—, —C(O)NH— or —NHC(O)—;

$R_4$ is selected from $C_{1-6}$ alkyl, $C_{1-6}$ haloalkyl, $C_{3-7}$ cycloalkyl or 3- to 7-membered heterocyclyl;

$R_6$ is selected from H, D, halogen, —$S(O)_mR_a$, —$S(O)_mOR_a$ or —$S(O)_mNR_bR_c$;

$R_7$ is selected from H, D, halogen, —$S(O)_mR_a$, —$S(O)_mOR_a$ or —$S(O)_mNR_bR_c$;

$R_8$ is independently selected from H, D, —$NH_2$, —$NHC_{1-6}$ alkyl, —$N(C_{1-6}$ alkyl$)_2$, $C_{1-6}$ alkyl or $C_{1-6}$ haloalkyl;

$R_a$ is independently selected from H, —$NH_2$, —$NHC_{1-6}$ alkyl, —$N(C_{1-6}$ alkyl$)_2$, $C_{1-6}$ alkyl or $C_{1-6}$ haloalkyl;

$R_b$ and $R_c$ are independently selected from H, —$C_{0-6}$ alkylene-$S(O)_mR'$, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl or —$C_{0-6}$ alkylene-3- to 7-membered heterocyclyl; or, $R_b$, $R_c$ and N atom are taken together to form 3- to 7-membered heterocyclyl;

R' is independently selected from H, $C_{1-6}$ alkyl, $C_{2-6}$ alkenyl, $C_{2-6}$ alkynyl or $C_{1-6}$ haloalkyl;

m represents 0, 1, or 2.

In a more specific embodiment, the present disclosure provides a compound of formula (I-6) or (I-6-1), or a pharmaceutically acceptable salt, an enantiomer, a diastereomer, a racemate, a solvate, a hydrate, a polymorph, a prodrug, or an isotope variant thereof, and mixtures thereof, wherein, ⎓ indicates a single bond or a double bond;

$R_1$ is selected from H, D, halogen, —CN or —$OR_a$;

$R_2$ is selected from H, D, halogen, —CN or —$OR_a$;

$R_3$ is —O—$C_{1-6}$ alkylene-$R_8$ or 5- to 6-membered heterocyclyl optionally substituted by 1 or 2 $R_8$ groups;

L is selected from a chemical bond, —C(O)—, —C(O)NH— or —NHC(O)—;

$R_4$ is selected from $C_{1-6}$ alkyl, $C_{1-6}$ haloalkyl, $C_{3-7}$ cycloalkyl or 3- to 7-membered heterocyclyl;

$R_6$ is selected from H, D or halogen;

$R_7$ is selected from H, D or halogen;

$R_8$ is independently selected from H, D, —$NH_2$, —$NHC_{1-6}$ alkyl, —$N(C_{1-6}$ alkyl$)_2$, $C_{1-6}$ alkyl or $C_{1-6}$ haloalkyl;

$R_a$ is independently selected from H, $C_{1-6}$ alkyl or $C_{1-6}$ haloalkyl.

In a more specific embodiment, the present disclosure provides a compound of formula (I-6) or (I-6-1), or a pharmaceutically acceptable salt, an enantiomer, a diastereomer, a racemate, a solvate, a hydrate, a polymorph, a prodrug, or an isotope variant thereof, and mixtures thereof, wherein, ⎓ indicates a single bond or a double bond;

$R_1$ is selected from H or D;

$R_2$ is selected from H or D;

$R_3$ is selected from —O—$C_{1-6}$ alkylene-$R_8$, piperazinyl or morpholinyl, the said group is optionally substituted with 1 $R_8$ group;

L is selected from a chemical bond or —C(O)—;

$R_4$ is selected from $C_{1-6}$ alkyl or $C_{1-6}$ haloalkyl;

$R_6$ is selected from H, D or F;

$R_7$ is selected from H, D or F;

$R_8$ is independently selected from H, D, —$NH_2$, —$NHC_{1-6}$ alkyl, —$N(C_{1-6}$ alkyl$)_2$, $C_{1-6}$ alkyl or $C_{1-6}$ haloalkyl.

In a more specific embodiment, the present disclosure provides a compound of formula (I-7) or (I-7-1), or a pharmaceutically acceptable salt, an enantiomer, a diastereomer, a racemate, a solvate, a hydrate, a polymorph, a prodrug, or an isotope variant thereof, and mixtures thereof:

(I-7)

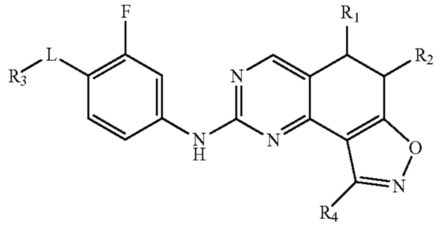

or

-continued (I-7-1)

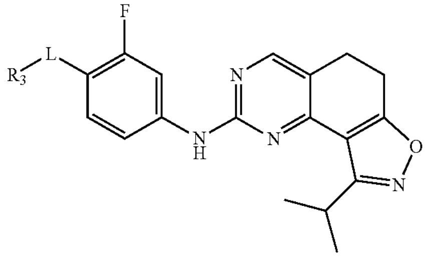

wherein, $R_1$ is selected from H, D, halogen, —CN, —$OR_a$, $C_{1-6}$ alkyl or $C_{1-6}$ haloalkyl;

$R_2$ is selected from H, D, halogen, —CN, —$OR_a$, $C_{1-6}$ alkyl or $C_{1-6}$ haloalkyl;

$R_3$ is 5- to 6-membered heterocyclyl optionally substituted with 1, 2 or 3 $R_8$ groups;

L is selected from a chemical bond, —C(O)—, —C(O)NH— or —NHC(O)—;

$R_4$ is selected from $C_{1-6}$ alkyl, $C_{1-6}$ haloalkyl, $C_{3-7}$ cycloalkyl or 3- to 7-membered heterocyclyl;

$R_8$ is independently selected from H, D, —$NH_2$, —$NHC_{1-6}$ alkyl, —$N(C_{1-6}$ alkyl$)_2$, $C_{1-6}$ alkyl or $C_{1-6}$ haloalkyl;

$R_a$ is independently selected from H, $C_{1-6}$ alkyl or $C_{1-6}$ haloalkyl.

In a more specific embodiment, the present disclosure provides a compound of formula (I-7) or (I-7-1), or a pharmaceutically acceptable salt, an enantiomer, a diastereomer, a racemate, a solvate, a hydrate, a polymorph, a prodrug, or an isotope variant thereof, and mixtures thereof, wherein, $R_1$ is selected from H, D, halogen, —CN or —$OR_a$;

$R_2$ is selected from H, D, halogen, —CN or —$OR_a$;

$R_3$ is 5- to 6-membered heterocyclyl optionally substituted with 1 or 2 $R_8$ groups;

L is selected from a chemical bond, —C(O)—, —C(O)NH— or —NHC(O)—;

$R_4$ is selected from $C_{1-6}$ alkyl, $C_{1-6}$ haloalkyl, $C_{3-7}$ cycloalkyl or 3- to 7-membered heterocyclyl;

$R_8$ is independently selected from H, D, $C_{1-6}$ alkyl or $C_{1-6}$ haloalkyl;

$R_a$ is independently selected from H, $C_{1-6}$ alkyl or $C_{1-6}$ haloalkyl.

In a more specific embodiment, the present disclosure provides a compound of formula (I-7) or (I-7-1), or a pharmaceutically acceptable salt, an enantiomer, a diastereomer, a racemate, a solvate, a hydrate, a polymorph, a prodrug, or an isotope variant thereof, and mixtures thereof, wherein, $R_1$ is selected from H or D;

$R_2$ is selected from H or D;

$R_3$ is piperazinyl or morpholinyl optionally substituted with one $R_8$ group;

L is selected from a chemical bond or —C(O)—;

$R_4$ is selected from $C_{1-6}$ alkyl or $C_{1-6}$ haloalkyl;

$R_8$ is selected from H, D, $C_{1-6}$ alkyl or $C_{1-6}$ haloalkyl.

In a more specific embodiment, the present disclosure provides a compound of formula (I-8) or (I-8-1), or a pharmaceutically acceptable salt, an enantiomer, a diastereomer, a racemate, a solvate, a hydrate, a polymorph, a prodrug, or an isotope variant thereof, and mixtures thereof:

(I-8)

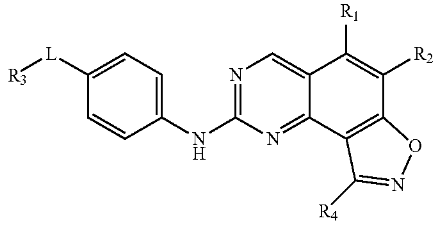

or (I-8-1)

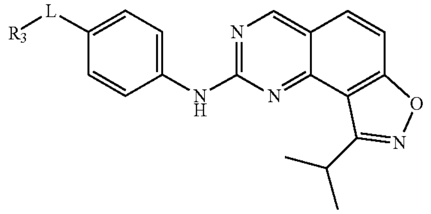

wherein, $R_1$ is selected from H, D, halogen, —CN, —$OR_a$, $C_{1-6}$ alkyl or $C_{1-6}$ haloalkyl;

$R_2$ is selected from H, D, halogen, —CN, —$OR_a$, $C_{1-6}$ alkyl or $C_{1-6}$ haloalkyl;

$R_3$ is 5- to 6-membered heterocyclyl optionally substituted with 1, 2 or 3 $R_8$ groups;

L is selected from a chemical bond, —C(O)—, —C(O)NH— or —NHC(O)—;

$R_4$ is selected from $C_{1-6}$ alkyl, $C_{1-6}$ haloalkyl, $C_{3-7}$ cycloalkyl or 3- to 7-membered heterocyclyl;

$R_8$ is independently selected from H, D, —$NH_2$, —$NHC_{1-6}$ alkyl, —$N(C_{1-6}$ alkyl$)_2$, $C_{1-6}$ alkyl or $C_{1-6}$ haloalkyl;

$R_a$ is independently selected from H, $C_{1-6}$ alkyl or $C_{1-6}$ haloalkyl.

In a more specific embodiment, the present disclosure provides a compound of formula (I-8) or (I-8-1), or a pharmaceutically acceptable salt, an enantiomer, a diastereomer, a racemate, a solvate, a hydrate, a polymorph, a prodrug, or an isotope variant thereof, and mixtures thereof, wherein, $R_1$ is selected from H, D, halogen, —CN or —$OR_a$;

$R_2$ is selected from H, D, halogen, —CN or —$OR_a$;

$R_3$ is 5- to 6-membered heterocyclyl optionally substituted with 1 or 2 $R_8$ groups;

L is selected from a chemical bond, —C(O)—, —C(O)NH— or —NHC(O)—;

$R_4$ is selected from $C_{1-6}$ alkyl, $C_{1-6}$ haloalkyl, $C_{3-7}$ cycloalkyl or 3- to 7-membered heterocyclyl;

$R_8$ is independently selected from H, D, $C_{1-6}$ alkyl or $C_{1-6}$ haloalkyl;

$R_a$ is independently selected from H, $C_{1-6}$ alkyl or $C_{1-6}$ haloalkyl.

In a more specific embodiment, the present disclosure provides a compound of formula (I-8) or (I-8-1), or a pharmaceutically acceptable salt, an enantiomer, a diastereomer, a racemate, a solvate, a hydrate, a polymorph, a prodrug, or an isotope variant thereof, and mixtures thereof, wherein, $R_1$ is selected from H or D;

$R_2$ is selected from H or D;

$R_3$ is piperazinyl or morpholinyl optionally substituted with one $R_8$ group;

L is selected from a chemical bond or —C(O)—;

$R_4$ is selected from $C_{1-6}$ alkyl or $C_{1-6}$ haloalkyl;

$R_8$ is selected from H, D, $C_{1-6}$ alkyl or $C_{1-6}$ haloalkyl.

In a more specific embodiment, the present disclosure provides a compound of formula (I-9) or (I-9-1), or a pharmaceutically acceptable salt, an enantiomer, a diastereomer, a racemate, a solvate, a hydrate, a polymorph, a prodrug, or an isotope variant thereof, and mixtures thereof:

(I-9)

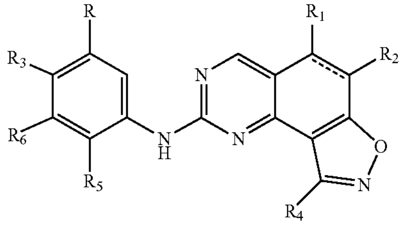

or (I-9-1)

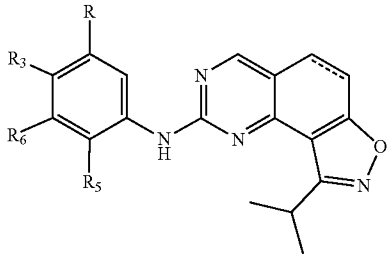

wherein,

⎓ indicates a single bond or a double bond;

$R_1$ is selected from H, D, halogen, —CN, —$OR_a$, —$SR_a$, —$NR_bR_c$, —$C(O)R_a$, —$C(O)OR_a$, —$C(O)NR_bR_c$, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl; wherein the said $C_{3-7}$ cycloalkyl or 3- to 7-membered heterocyclyl is optionally substituted by oxo or thioxo;

$R_2$ is selected from H, D, halogen, —CN, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl; wherein the said $C_{3-7}$ cycloalkyl or 3- to 7-membered heterocyclyl is optionally substituted by oxo or thioxo;

$R_3$ is selected from H, D, halogen, —CN, —$NO_2$, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, —O—$C_{1-6}$ alkylene-$R_8$, $C_{1-6}$ alkyl, $C_{1-6}$ haloalkyl, $C_{3-7}$ cycloalkyl, 3- to 11-membered heterocyclyl, $C_{6-10}$ aryl, or 5- to 10-membered heteroaryl, each of which is optionally substituted by 1, 2, 3, 4, or 5 $R_8$ groups;

$R_4$ is selected from H, D, —$C(O)R_a$, —$C(O)OR_a$, —$C(O)NR_bR_c$, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl;

$R_5$ is selected from H, D, halogen, —CN, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, $C_{1-6}$ alkyl or $C_{1-6}$ haloalkyl;

$R_6$ is selected from H, D, halogen, —CN, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, $C_{1-6}$ alkyl or $C_{1-6}$ haloalkyl;

$R_7$ is selected from H, D, halogen, —CN, —$OR_a$, —$SR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, $C_{1-6}$ alkyl or $C_{1-6}$ haloalkyl;

$R_8$ is selected from H, D, —$NH_2$, —$NHC_{1-6}$ alkyl, —N($C_{1-6}$ alkyl)$_2$, $C_{1-6}$ alkyl, $C_{1-6}$ haloalkyl, —$C_{0-6}$ alkylene-$OR_a$, $C_{3-7}$ cycloalkyl, 3- to 7-membered heterocyclyl, $C_{6-10}$ aryl, or 5- to 10-membered heteroaryl; or two $R_8$ on the same atom are taken together to form oxo or thioxo;

$R_a$ is independently selected from H, —$C_{0-6}$ alkylene-CN, —$C_{0-6}$ alkylene-$NO_2$, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C(O)OR', —$C_{0-6}$ alkylene-C(O)NR"R'", —$C_{0-6}$ alkylene-S(O)$_m$R', —$C_{0-6}$ alkylene-S(O)$_m$OR', —$C_{0-6}$ alkylene-S(O)$_m$NR"R'", $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl;

$R_b$ and $R_c$ are independently selected from H, —$C_{0-6}$ alkylene-CN, —$C_{0-6}$ alkylene-$NO_2$, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C(O)OR', —$C_{0-6}$ alkylene-C(O)NR"R'", —$C_{0-6}$ alkylene-S(O)$_m$R', —$C_{0-6}$ alkylene-S(O)$_m$OR', —$C_{0-6}$ alkylene-S(O)$_m$NR"R'", $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or, $R_b$, $R_c$ and N atom are taken together to form 3- to 7-membered heterocyclyl;

R' is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl;

R" and R'" are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl; or, R", R'" and N atom are taken together to form 3- to 7-membered heterocyclyl;

m represents 0, 1, or 2.

In a more specific embodiment, the present disclosure provides a compound of formula (I-9) or (I-9-1), or a pharmaceutically acceptable salt, an enantiomer, a diastereomer, a racemate, a solvate, a hydrate, a polymorph, a prodrug, or an isotope variant thereof, and mixtures thereof, wherein, ⎓ indicates a single bond or a double bond;

$R_1$ is selected from H, D, halogen, —CN, —$OR_a$, —$SR_a$, —$NR_bR_c$, $C_{1-6}$ alkyl or $C_{1-6}$ haloalkyl;

$R_2$ is selected from H, D, halogen, —CN, —$OR_a$, —$SR_a$, —$NR_bR_c$, $C_{1-6}$ alkyl or $C_{1-6}$ haloalkyl;

$R_3$ is selected from H, D, halogen, —CN, —$NO_2$, —$OR_a$, —$SR_a$, —$NR_bR_c$, —C(O)$R_a$, —C(O)$OR_a$, —C(O)$NR_bR_c$, —S(O)$_m$$R_a$, —S(O)$_m$$OR_a$, —S(O)$_m$$NR_bR_c$, $C_{1-6}$ alkyl, $C_{1-6}$ haloalkyl, $C_{3-7}$ cycloalkyl or 4- to 7-membered heterocyclyl, the said group is optionally substituted with 1, 2 or 3 $R_8$ groups;

$R_4$ is selected from H, D, $C_{1-6}$ alkyl, $C_{1-6}$ haloalkyl, $C_{3-7}$ cycloalkyl or 3- to 7-membered heterocyclyl;

$R_5$ is selected from H, D, halogen, —CN, —$OR_a$, —$SR_a$, —$NR_bR_c$, $C_{1-6}$ alkyl or $C_{1-6}$ haloalkyl;

$R_6$ is selected from H, D, halogen, —CN, —$OR_a$, —$SR_a$, —$NR_bR_c$, —C(O)$R_a$, —C(O)$OR_a$, —C(O)$NR_bR_c$, —S(O)$_m$$R_a$, —S(O)$_m$$OR_a$, —S(O)$_m$$NR_bR_c$, $C_{1-6}$ alkyl or $C_{1-6}$ haloalkyl;

$R_7$ is selected from H, D, halogen, —CN, —$OR_a$, —$SR_a$, —$NR_bR_c$, —C(O)$R_a$, —C(O)$OR_a$, —C(O)$NR_bR_c$, —S(O)$_m$$R_a$, —S(O)$_m$$OR_a$, —S(O)$_m$$NR_bR_c$, $C_{1-6}$ alkyl or $C_{1-6}$ haloalkyl;

$R_8$ is selected from H, D, —$NH_2$, —$NHC_{1-6}$ alkyl, —N($C_{1-6}$ alkyl)$_2$, $C_{1-6}$ alkyl or $C_{1-6}$ haloalkyl; or two $R_8$ on the same atom are taken together to form oxo or thioxo;

$R_a$ is independently selected from H, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C(O)OR', —$C_{0-6}$ alkylene-C(O)NR"R'", —$C_{0-6}$ alkylene-S(O)$_m$R', —$C_{0-6}$ alkylene-S(O)$_m$OR', —$C_{0-6}$ alkylene-S(O)$_m$NR"R'", $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl or —$C_{0-6}$ alkylene-3- to 7-membered heterocyclyl;

$R_b$ and $R_c$ are independently selected from H, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C(O)OR', —$C_{0-6}$ alkylene-C(O)NR"R'", —$C_{0-6}$ alkylene-S(O)$_m$R', —$C_{0-6}$ alkylene-S(O)$_m$OR', —$C_{0-6}$ alkylene-S(O)$_m$NR"R'", $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl or —$C_{0-6}$ alkylene-3- to 7-membered heterocyclyl; or, $R_b$, $R_c$ and N atom are taken together to form 3- to 7-membered heterocyclyl;

R' is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl;

R" and R'" are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl; or, R", R'" and N atom are taken together to form 3- to 7-membered heterocyclyl;

m represents 0, 1, or 2.

In a more specific embodiment, the present disclosure provides a compound of formula (I-9) or (I-9-1), or a pharmaceutically acceptable salt, an enantiomer, a diastereomer, a racemate, a solvate, a hydrate, a polymorph, a prodrug, or an isotope variant thereof, and mixtures thereof, wherein, ⎓ indicates a single bond or a double bond;

$R_1$ is selected from H, D, halogen, —CN, —$OR_a$, $C_{1-6}$ alkyl or $C_{1-6}$ haloalkyl;

$R_2$ is selected from H, D, halogen, —CN, —$OR_a$, $C_{1-6}$ alkyl or $C_{1-6}$ haloalkyl;

$R_3$ is selected from H, D, halogen, —CN, —$NO_2$, —$OR_a$, —$SR_a$, —$NR_bR_c$, —C(O)$R_a$, —C(O)$OR_a$, —C(O)$NR_bR_c$, —S(O)$_m$$R_a$, —S(O)$_m$$OR_a$, —S(O)$_m$$NR_bR_c$, $C_{3-7}$ cycloalkyl or 4- to 7-membered heterocyclyl, the said group is optionally substituted with 1 or 2 $R_8$ groups;

$R_4$ is selected from $C_{1-6}$ alkyl, $C_{1-6}$ haloalkyl, $C_{3-7}$ cycloalkyl or 3- to 7-membered heterocyclyl;

$R_5$ is selected from H, D, halogen, —CN, —$OR_a$, —$SR_a$, —$NR_bR_c$, $C_{1-6}$ alkyl or $C_{1-6}$ haloalkyl;

$R_6$ is selected from H, D, halogen, —CN, —$OR_a$, —$SR_a$, —$NR_bR_c$, —C(O)$R_a$, —C(O)$OR_a$, —C(O)$NR_bR_c$, —S(O)$_m$$R_a$, —S(O)$_m$$OR_a$, —S(O)$_m$$NR_bR_c$, $C_{1-6}$ alkyl or $C_{1-6}$ haloalkyl;

$R_7$ is selected from H, D, halogen, —CN, —$OR_a$, —$SR_a$, —$NR_bR_c$, —C(O)$R_a$, —C(O)$OR_a$, —C(O)$NR_bR_c$, —S(O)$_m$$R_a$, —S(O)$_m$$OR_a$, —S(O)$_m$$NR_bR_c$, $C_{1-6}$ alkyl or $C_{1-6}$ haloalkyl;

$R_8$ is selected from H, D, $C_{1-6}$ alkyl or $C_{1-6}$ haloalkyl;

$R_a$ is independently selected from H, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C(O)OR', —$C_{0-6}$ alkylene-C(O)NR"R'", —$C_{0-6}$ alkylene-$S(O)_m$R', —$C_{0-6}$ alkylene-$S(O)_m$OR', —$C_{0-6}$ alkylene-$S(O)_m$NR"R'", $C_{1-6}$ alkyl, $C_{1-6}$ haloalkyl, —$C_{0-6}$ alkylene-$C_{3-7}$ cycloalkyl or —$C_{0-6}$ alkylene-3- to 7-membered heterocyclyl;

$R_b$ and $R_c$ are independently selected from H, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C (O)OR', —$C_{0-6}$ alkylene-C(O)NR"R'", —$C_{0-6}$ alkylene-$S(O)_m$R', —$C_{0-6}$ alkylene-$S(O)_m$OR', —$C_{0-6}$ alkylene-$S(O)_m$NR"R'", $C_{1-6}$ alkyl, $C_{1-6}$ haloalkyl, —$C_{0-6}$ alkylene-$C_{3-7}$ cycloalkyl or —$C_{0-6}$ alkylene-3- to 7-membered heterocyclyl; or, $R_b$, $R_c$ and N atom are taken together to form 3- to 7-membered heterocyclyl;

R' is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl;

R" and R'" are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl; or, R", R'" and N atom are taken together to form 3- to 7-membered heterocyclyl;

m represents 0, 1, or 2.

In a more specific embodiment, the present disclosure provides a compound of formula (I-9) or (I-9-1), or a pharmaceutically acceptable salt, an enantiomer, a diastereomer, a racemate, a solvate, a hydrate, a polymorph, a prodrug, or an isotope variant thereof, and mixtures thereof, wherein, ⎓ indicates a single bond or a double bond;

$R_1$ is selected from H or D;

$R_2$ is selected from H or D;

$R_3$ is selected from H, D, —$OR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, $C_{4-6}$ cycloalkyl or 5- to 6-membered heterocyclyl, the said group is optionally substituted with 1 $R_8$ group;

$R_4$ is selected from $C_{1-6}$ alkyl, $C_{1-6}$ haloalkyl, $C_{3-7}$ cycloalkyl or 3- to 7-membered heterocyclyl;

$R_5$ is selected from H, D, halogen, —$OR_a$, —$SR_a$ or —$NR_bR_c$;

$R_6$ is selected from H, D, halogen, —$C(O)R_a$, —C(O) $OR_a$, —$C(O)NR_bR_c$, —$S(O)_mR_a$, —$S(O)_mOR_a$ or —$S(O)_mNR_bR_c$;

$R_7$ is selected from H, D, halogen, —$C(O)R_a$, —C(O) $OR_a$, —$C(O)NR_bR_c$, —$S(O)_mR_a$, —$S(O)_mOR_a$ or —$S(O)_mNR_bR_c$;

$R_8$ is selected from H, D, $C_{1-6}$ alkyl or $C_{1-6}$ haloalkyl;

$R_a$ is independently selected from H, —$C_{0-6}$ alkylene-OR', —$C_{0-6}$ alkylene-NR"R'", —$C_{0-6}$ alkylene-C(O)R', —$C_{0-6}$ alkylene-$S(O)_m$R', $C_{1-6}$ alkyl, $C_{1-6}$ haloalkyl, —$C_{0-6}$ alkylene-$C_{37}$ cycloalkyl or —$C_{0-6}$ alkylene-3- to 7-membered heterocyclyl;

$R_b$ and $R_c$ are independently selected from H, —$C_{0-6}$ alkylene-OR', —$C_{0-6}$ alkylene-NR"R'", —$C_{0-6}$ alkylene-C(O)R', —$C_{0-6}$ alkylene-$S(O)_m$R', $C_{1-6}$ alkyl, $C_{1-6}$ haloalkyl, —$C_{0-6}$ alkylene-$C_{37}$ cycloalkyl or —$C_{0-6}$ alkylene-3- to 7-membered heterocyclyl; or, $R_b$, $R_c$ and N atom are taken together to form 5- to 6-membered heterocyclyl;

R' is independently selected from H, $C_{1-6}$ alkyl or $C_{1-6}$ haloalkyl;

R" and R'" are independently selected from H, $C_{1-6}$ alkyl or $C_{1-6}$ haloalkyl; or, R", R'" and N atom are taken together to form 5- to 6-membered heterocyclyl;

m represents 0, 1, or 2.

The compounds of the present disclosure may include one or more asymmetric centers, and thus may exist in a variety of stereoisomeric forms, for example, enantiomers and/or diastereomers. For example, the compounds of the present disclosure may be in the form of an individual enantiomer, diastereomer or geometric isomer (e.g., cis- and trans-isomers), or may be in the form of a mixture of stereoisomers, including racemic mixture and a mixture enriched in one or more stereoisomers. The isomers can be separated from the mixture by the methods known to those skilled in the art, including chiral high pressure liquid chromatography (HPLC) and the formation and crystallization of chiral salts; or preferred isomers can be prepared by asymmetric synthesis.

It will be understood by those skilled in the art that the organic compounds can form complexes with solvents in which they are reacted or from which they are precipitated or crystallized. These complexes are known as "solvates." Where the solvent is water, the complex is known as "hydrate." The present disclosure encompasses all solvates of the compounds of the present disclosure.

The term "solvate" refers to forms of a compound or a salt thereof, which are associated with a solvent, usually by a solvolysis reaction. This physical association may include hydrogen bonding. Conventional solvents include water, methanol, ethanol, acetic acid, DMSO, THF, diethyl ether, etc. The compounds described herein can be prepared, for example, in crystalline form, and can be solvated. Suitable solvates include pharmaceutically acceptable solvates and further include both stoichiometric solvates and non-stoichiometric solvates. In some cases, the solvates will be capable of isolation, for example, when one or more solvent molecules are incorporated into the crystal lattice of a crystalline solid. "Solvate" includes both solution-phase and isolatable solvates. Representative solvates include hydrates, ethanolates and methanolates.

The term "hydrate" refers to a compound that is associated with water. Generally, the number of water molecules contained in a hydrate of a compound is in a definite ratio to the number of the compound molecules in the hydrate. Therefore, hydrates of a compound can be represented, for example, by a general formula R·x $H_2O$, wherein R is the compound, and x is a number greater than 0. Given compounds can form more than one type of hydrates, including, for example, monohydrates (x is 1), lower hydrates (x is a number greater than 0 and smaller than 1, for example, hemihydrates (R·0.5$H_2O$)) and polyhydrates (x is a number greater than 1, for example, dihydrates (R·2$H_2O$) and hexahydrates (R·6$H_2O$)).

Compounds of the present disclosure may be in an amorphous or a crystalline form (polymorph). Furthermore, the compounds of the present disclosure may exist in one or more crystalline forms. Therefore, the present disclosure includes all amorphous or crystalline forms of the compounds of the present disclosure within its scope. The term "polymorph" refers to a crystalline form of a compound (or a salt, hydrate or solvate thereof) in a particular crystal packing arrangement. All polymorphs have the same elemental composition. Different crystalline forms generally have different X-ray diffraction patterns, infrared spectra, melting points, density, hardness, crystal shapes, optical and electrical properties, stability, and solubility. Recrystallization solvents, rate of crystallization, storage temperatures, and other factors may cause one crystalline form to dominate. Various polymorphs of a compound can be prepared by crystallization under different conditions.

The present disclosure also comprises compounds that are labeled with isotopes (isotopic variants), which are equivalent to those described in formula (I), but one or more atoms are replaced by atoms having an atom mass or mass number that are different from that of atoms that are common in nature. Examples of isotopes which may be introduced into the compounds of the disclosure include isotopes of hydrogen, carbon, nitrogen, oxygen, phosphorus, sulfur, fluorine and chlorine, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$ and $^{36}Cl$, respectively. Compounds of the present disclosure that comprise the above isotopes and/or other isotopes of other atoms, prodrugs thereof and pharmaceutically acceptable salts of said compounds or prodrugs all are within the scope of the present disclosure. Certain isotope-labeled compounds of the present disclosure, such as those incorporating radioactive isotopes (e.g., $^{3}H$ and $^{14}C$), can be used for the measurement of the distribution of drug and/or substrate in tissue. Tritium, which is $^{3}H$ and carbon-14, which is $^{14}C$ isotope, are particularly preferred, because they are easy to prepare and detect. Furthermore, replaced by heavier isotopes, such as deuterium, which is $^{2}H$, may provide therapeutic benefits due to the higher metabolic stability, such as prolonging the half-life in vivo or decreasing the dosage requirements, and thus may be preferred in some cases. Isotope-labeled compounds of formula (I) of the present disclosure and prodrugs thereof can be prepared generally by using readily available isotope-labeled reagents to replace non-isotope-labeled reagents in the following schemes and/or the procedures disclosed in the examples and preparation examples.

In addition, prodrugs are also included within the context of the present disclosure. The term "prodrug" as used herein refers to a compound that is converted into an active form that has medical effects in vivo by, for example, hydrolysis in blood. Pharmaceutically acceptable prodrugs are described in T. Higuchi and V. Stella, Prodrugs as Novel Delivery Systems, A.C.S. Symposium Series, Vol. 14, Edward B. Roche, ed., Bioreversible Carriers in Drug Design, American Pharmaceutical Association and Pergamon Press, 1987, and D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

The present disclosure also provides a pharmaceutical formulation comprising a therapeutically effective amount of a compound of formula (I), or therapeutically acceptable salts thereof, and pharmaceutically acceptable carriers, diluents or excipients thereof. All of these forms belong to the present disclosure.

The preferred compounds disclosed herein include but are not limited to the following compounds, or a pharmaceutically acceptable salt, an enantiomer, a diastereomer, a racemate, a solvate, a hydrate, a polymorph, a prodrug, or an isotope variant thereof, and mixtures thereof:

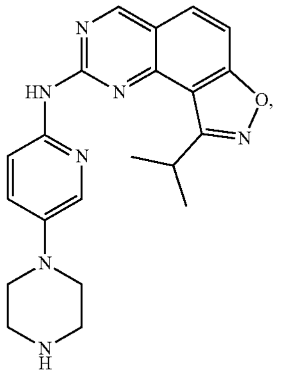

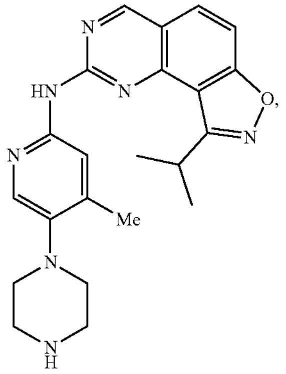

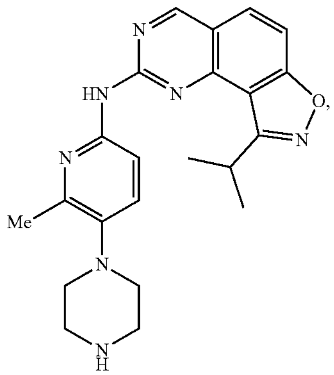

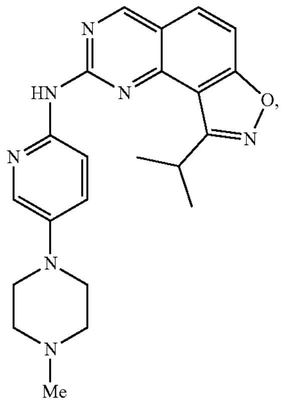

-continued
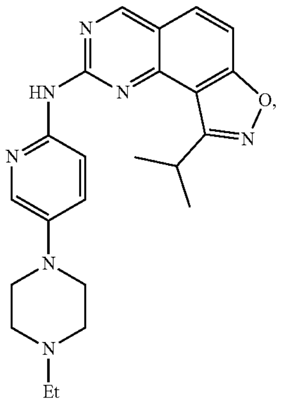
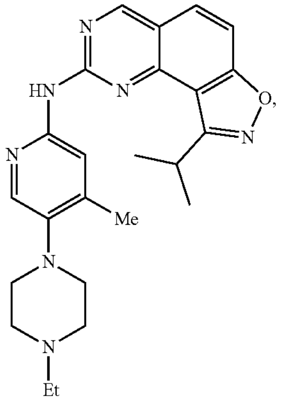
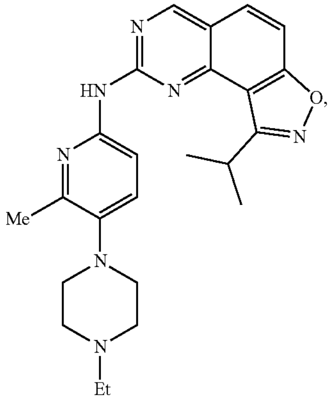
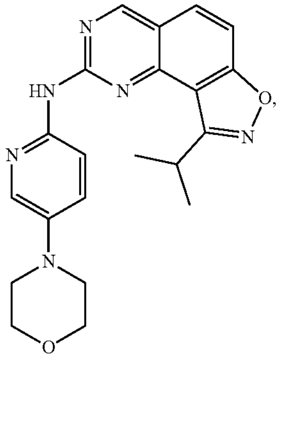
-continued
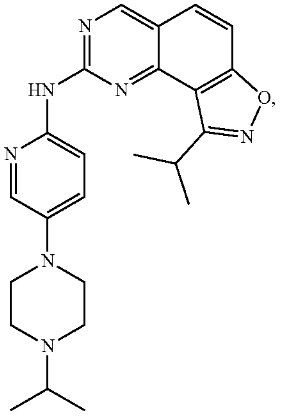
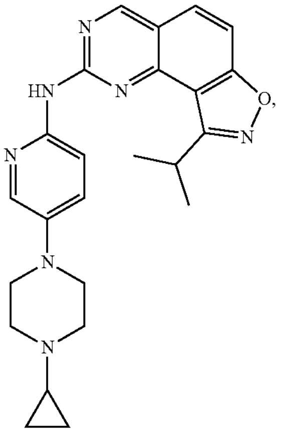
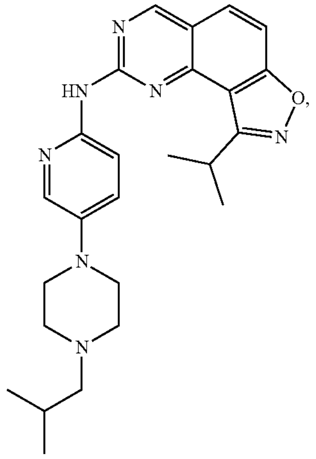
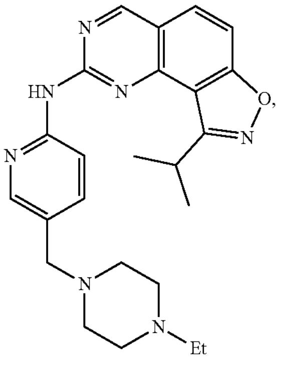

-continued
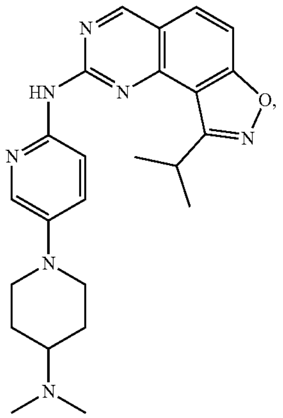
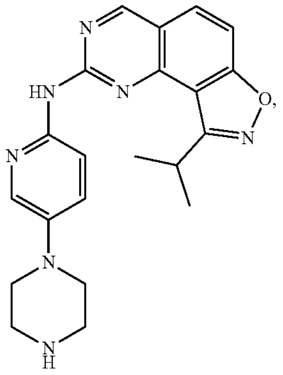
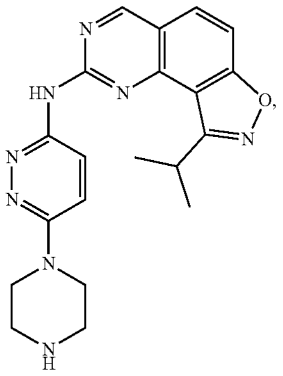
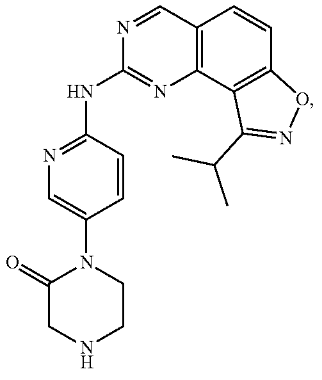
-continued
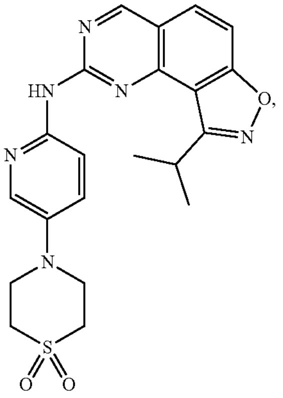
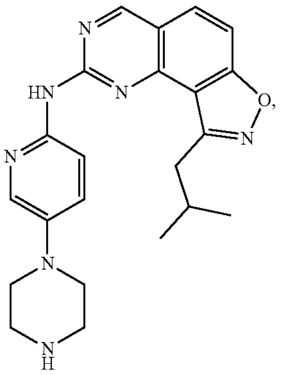
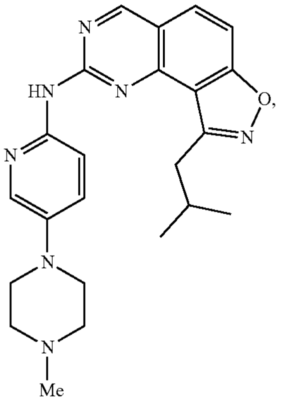
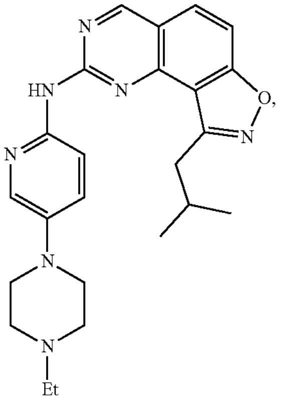

-continued
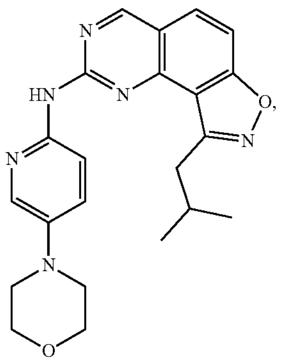
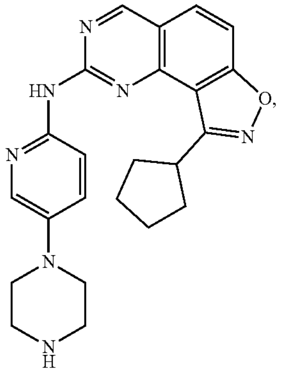
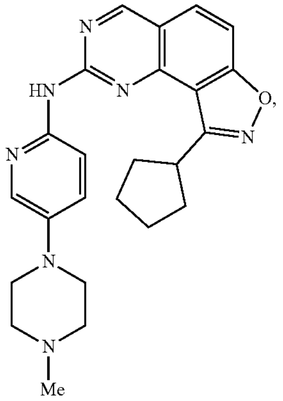
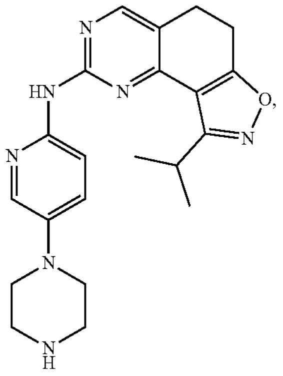
-continued
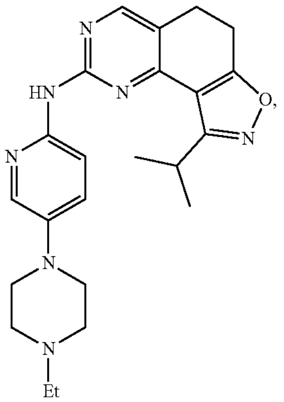
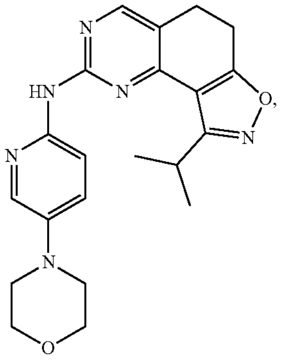
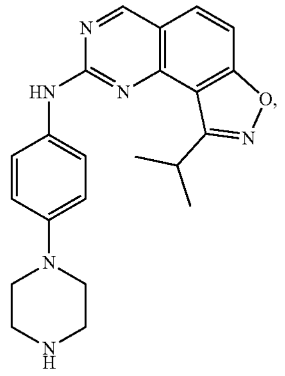
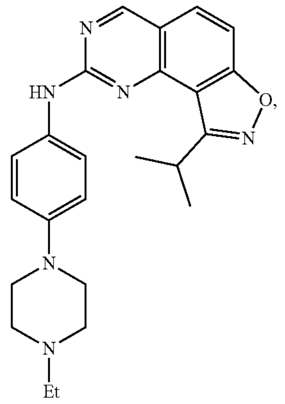

-continued
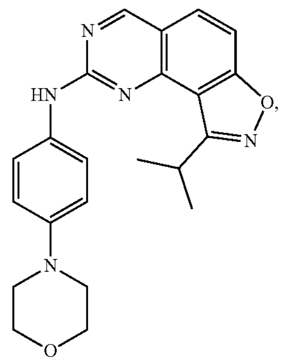
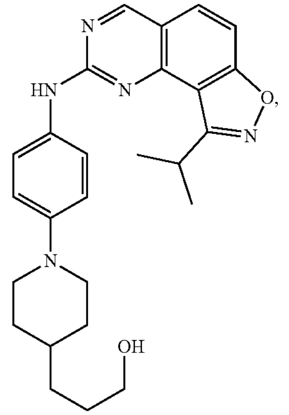
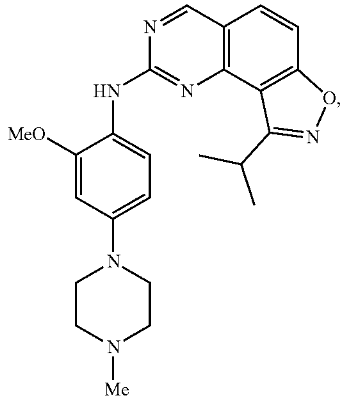
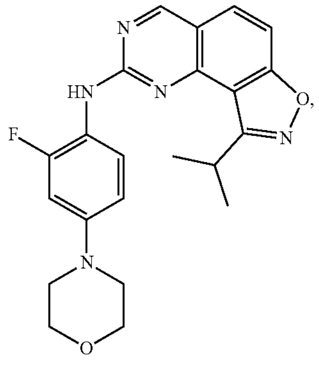
-continued
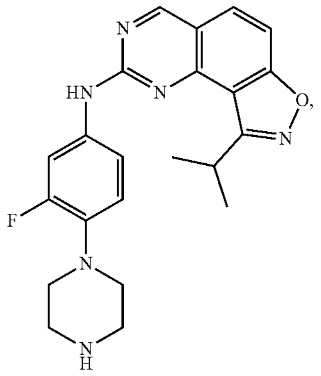
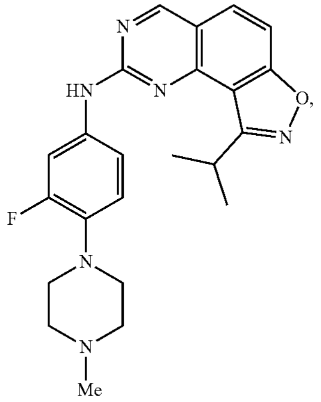
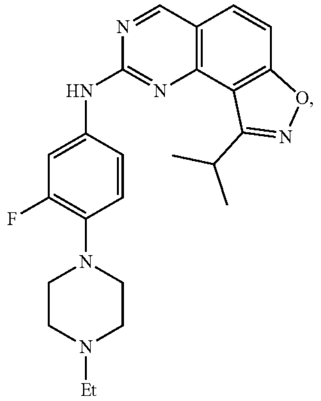
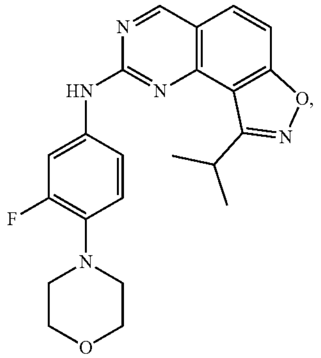

-continued

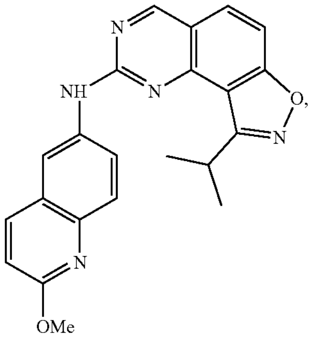

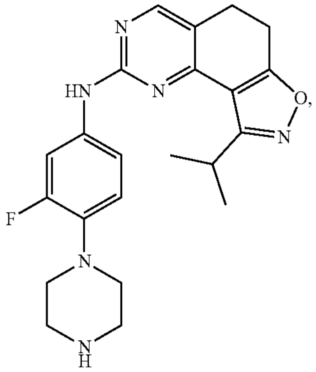

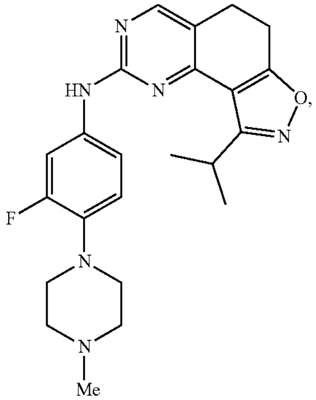

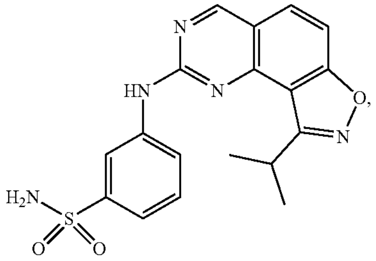

-continued

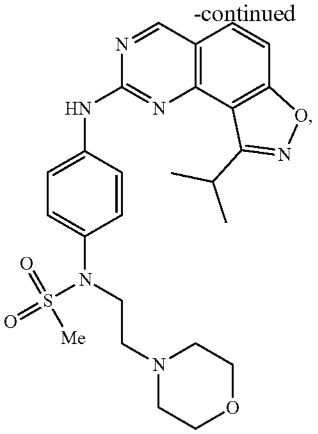

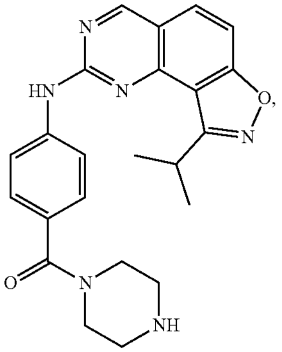

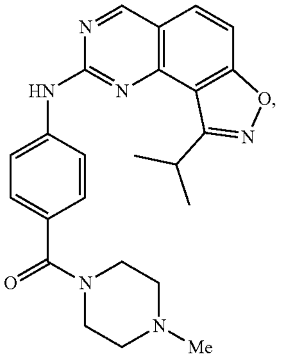

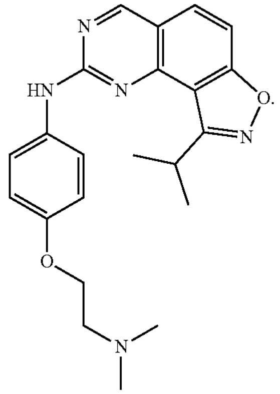

Pharmaceutical Compositions, Kits and Administration

In another aspect, the present disclosure provides a pharmaceutical composition comprising a compound of the present disclosure (also referred to as the "active ingredient") and pharmaceutically acceptable excipients. In some embodiments, the pharmaceutical composition comprises an effective amount of the compound of the present disclosure. In some embodiments, the pharmaceutical composition comprises a therapeutically effective amount of the compound of the present disclosure. In some embodiments, the pharmaceutical composition comprises a prophylactically effective amount of the compound of the present disclosure.

Pharmaceutically acceptable excipients for use in the present disclosure refer to the non-toxic carriers, adjuvants or vehicles, which do not destroy the pharmacological activity of the compounds formulated together. Pharmaceutically acceptable carriers, adjuvants, or vehicles that can be used in the compositions of the present disclosure include (but are not limited to) ion exchangers, alumina, aluminum stearate, lecithin, serum proteins (such as human serum proteins), buffer substances (such as phosphate), glycine, sorbic acid, potassium sorbate, mixture of partial glycerides of saturated plant fatty acids, water, salts or electrolytes (such as protamine sulfate), disodium hydrogen phosphate, potassium hydrogen phosphate, sodium chloride, zinc salts, silica gel, magnesium trisilicate, polyvinyl pyrrolidone, cellulose-based substance, polyethylene glycol, sodium carboxymethyl cellulose, polyacrylate, wax, polyethylene-polyoxypropylene block polymers, polyethylene glycol and lanolin.

The present disclosure also includes kits (e.g., pharmaceutical packs). The kits provided may include a compound of the present disclosure, other therapeutic agent(s), and a first and a second containers (e.g., vials, ampoules, bottles, syringes, and/or dispersible packages or other suitable containers) containing the compound of the present disclosure and other therapeutic agent(s). In some embodiments, the provided kits can also optionally include a third container containing a pharmaceutically acceptable excipient for diluting or suspending the compound of the present disclosure and/or other therapeutic agent(s). In some embodiments, the compound of the present disclosure provided in the first container and other therapeutic agent(s) provided in the second container are combined to form a unit dosage form.

The pharmaceutical composition provided by the present disclosure can be administered by a variety of routes including, but not limited to, oral administration, parenteral administration, inhalation administration, topical administration, rectal administration, nasal administration, buccal administration, vaginal administration, administration by implant or other means of administration. For example, parenteral administration as used herein includes subcutaneous administration, intradermal administration, intravenous administration, intramuscular administration, intra-articular administration, intra-arterial administration, intrasynovial administration, intrasternal administration, intracerebroventricular administration, intralesional administration, and intracranial injection or infusion techniques.

Generally, the compounds provided herein are administered in an effective amount. The amount of the compound actually administered will typically be determined by a physician, in the light of the relevant circumstances, including the condition to be treated, the route of administration selected, the actual compound administered, the age, weight and response of the individual patient, the severity of the patient's symptoms, etc.

EXAMPLES

The following examples are provided to provide those skilled in the art with a complete disclosure and description of how to implement, prepare and evaluate the methods and compounds claimed herein, and are intended to be illustrative only without limiting the scope of the invention.

The preparation protocol of the compound disclosed herein is shown, for example, in Scheme 1.

Scheme 1

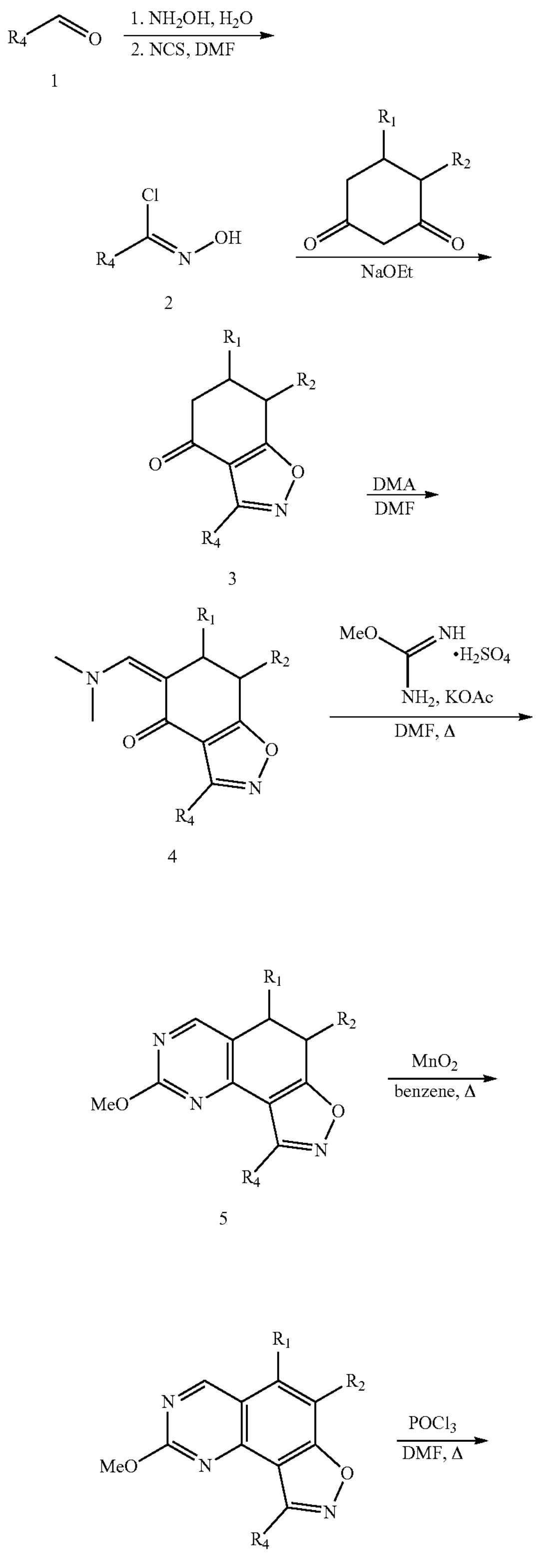

1
2
3
4
5
6

-continued

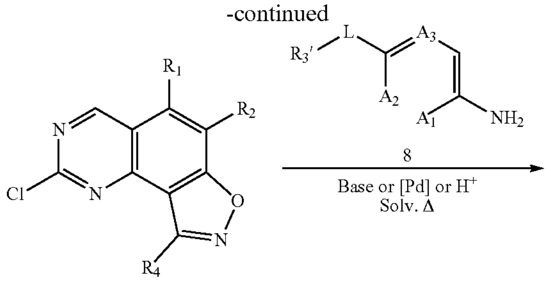

7

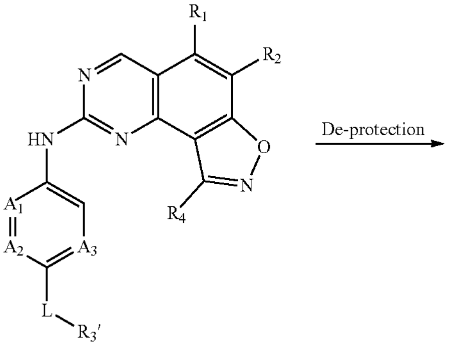

Ia

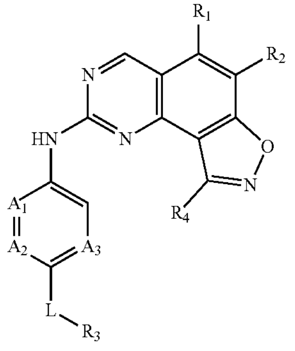

I

The compound of formula I could be prepared according to the above general scheme. Firstly, the aldoxime obtained from the reaction of aldehyde (1) with hydroxylamine was reacted with NCS to afford intermediate (2). (2) is reacted with 1,3-cyclohexanedione via isoxazole ring formation to give 6,7-dihydrobenzo[d]isoxazol-4-(5H)-one (3). Then, (3) is reacted with N,N-dimethylformamide dimethylacetal to afford intermediate (4). Intermediate (4) is reacted with O-methylisourea sulfate via pyrimidine ring formation to give 2-methoxy-5,6-dihydroisoxazolo[5,4-H]quinazoline (5). Afterwards, (5) is subjected to oxidative aromatization by manganese dioxide and subsequent chlorination to give a chloride (7). Compound (7) is coupled with an amine (8) to afford compound of formula (Ia), wherein $R_3$' represents $R_3$ protected by a protecting group (such as Boc), which is deprotected to give the compound of formula (I); or when there is no need of a protecting group on $R_3$, $R_3$' is $R_3$, and the compound of formula (Ia) is the compound of formula (I).

Scheme 2

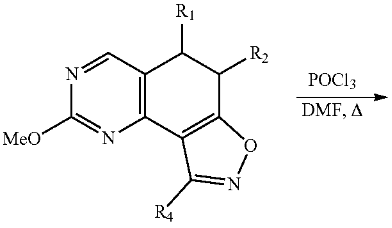

5

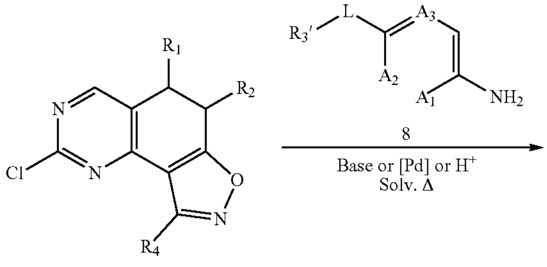

9

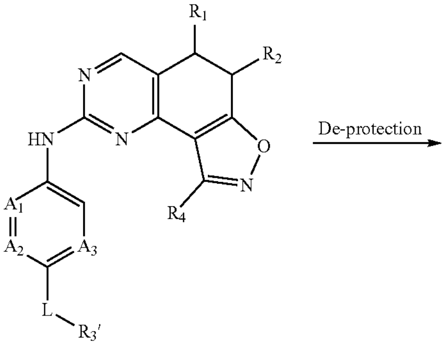

Ia'

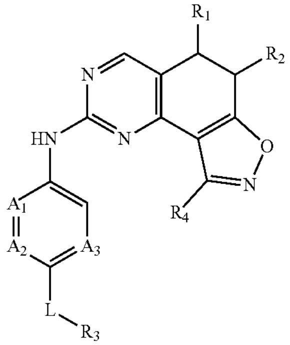

I'

The intermediate (5) is chlorinated to afford the chlorinated compound (9). The compound (9) is coupled with an amine (8) to give compound of formula (Ia'), wherein $R_3$' represents $R_3$ protected by a protecting group (such as Boc), which is deprotected to give the compound of formula (I'); or when there is no need of a protecting group on $R_3$, $R_3$' is $R_3$, and the compound of formula (Ia') is the compound of formula (I').

Example I-1

9-isopropyl-N-(5-(piperazin-1-yl)pyridin-2-yl)isoxazolo[5,4-H]quinazolin-2-amine hydrochloride (I-1)

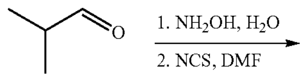

1a

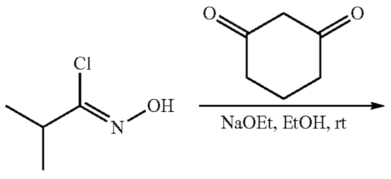

2a

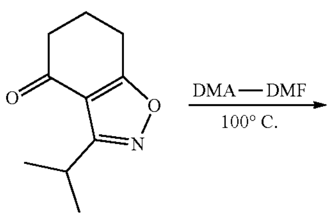

3a

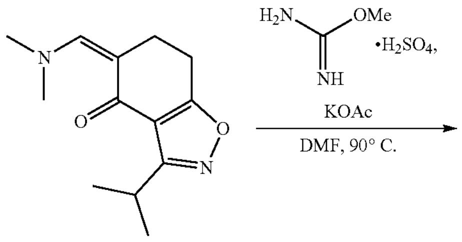

4a

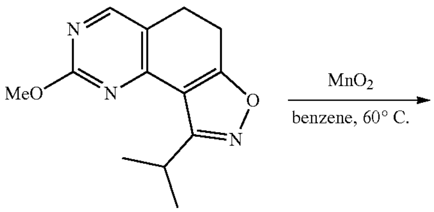

5a

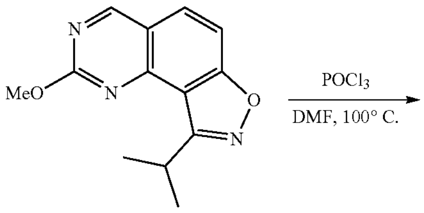

6a

-continued

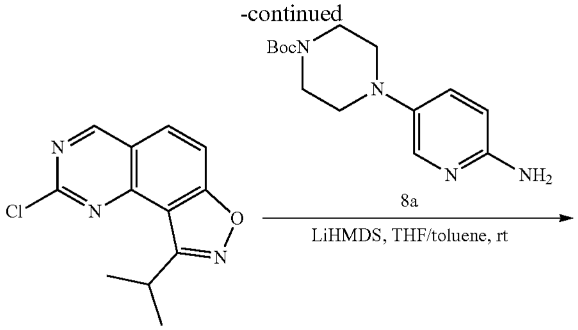

7a

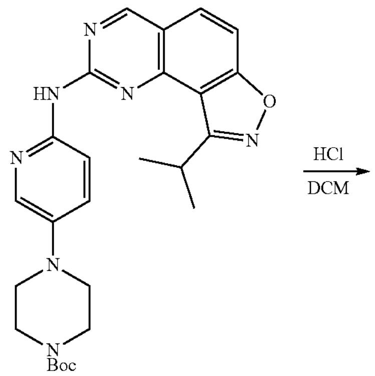

I-1a

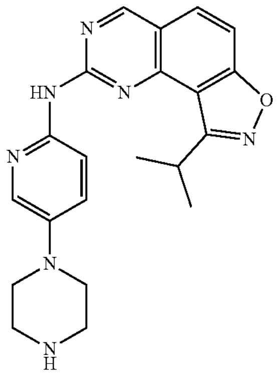

I-1

1): (Z)—N-hydroxyisobutyrylimide chloride (2a)

To a solution of isobutyraldehyde 1a (20 g, 0.278 mol) in water (300 mL) was added dropwise an aqueous hydroxylamine solution (25.4 mL, 50%) in an ice-water bath. After the dripping was completed, the mixture was allowed to warm to room temperature and reacted for 12 hours. The reaction solution was extracted three times with dichloromethane (200 mL), and the organic layers were combined, dried (anhydrous sodium sulfate), filtered by suction, and concentrated. The obtained crude product (20.4 g) was dissolved in N,N-dimethylformamide (200 mL), and N-chlorosuccinimide (34.4 g, 0.258 mmol) was added in four portions in an ice-water bath. The mixture was warmed to room temperature, and the reaction was continued for 24 hours. Diethyl ether (600 mL) was added to dilute the reaction solution, and then the reaction solution was washed with water (80 mL) for three times, saturated brine (80 mL) once, separately. The resulting solution was dried (anhydrous sodium sulfate), filtered by suction, and concentrated to give the crude title compound 2a (26 g) as a pale yellow oil. LC-MS (ESI), $C_4H_9ClNO$ $[M+H]^+$: m/z=122.0, 124.1. The crude product was directly used in the next reaction without further purification.

2): 3-isopropyl-6,7-dihydrobenzo[d]isoxazol-4-(5H)-one (3a)

To a solution of the above crude 2a (26 g) and 1,3-cyclohexanedione (36 g, 0.322 mol) in anhydrous ethanol (300 mL) was added dropwise sodium ethoxide (109.6 g, 20% in ethanol) in an ice bath. After dripping was completed, the mixture was warmed to room temperature, and the reaction was continued until TLC monitoring showed that the raw materials was completely reacted. Hydrogen chloride (1M in water) was slowly added dropwise to adjust the pH of the reaction solution to about 8. The solution was concentrated under reduced pressure, and the resulting crude product was purified by flash silica gel column chromatography (petroleum ether/ethyl acetate=20:1 to 10:1) to give the title compound 3a (15.9 g, 89.0 mmol, 32% yield for three steps) as a pale yellow solid. $^1$H NMR (600 MHz, Chloroform-d, ppm) S 3.35 (hept, J=6.9 Hz, 1H), 2.96 (t, J=6.3 Hz, 2H), 2.51 (dd, J=7.2, 5.7 Hz, 2H), 2.20 (p, J=6.4 Hz, 2H), 1.33 (d, J=6.9 Hz, 6H).

3): (Z)-5-((dimethylamino)methylene)-3-isopropyl-6,7-dihydrobenzo[d]isoxazol-4-(5H)-one (4a)

A solution of 3a (14.0 g, 78.2 mmol) and N,N-dimethylformamide dimethylacetal (51.9 mL, 0.391 mol) in N,N-dimethylformamide (104 mL) was stirred to react at 100° C. for 12 hours. After cooling to room temperature, the reaction solution was concentrated under reduced pressure to give the title compound 4a (17.3 g) as a brown oil. This crude product was directly used in the next reaction without further purification. LC-MS (ESI), $C_{13}H_{19}N_2O_2$ $[M+H]^+$: m/z=235.2.

4): 9-isopropyl-2-methoxy-5,6-dihydroisoxazolo[5,4-H]quinazoline (5a)

The crude product from the previous step was dissolved in N,N-dimethylformamide (200 mL), and O-methylisourea sulfate (38.5 g, 156.4 mmol) and anhydrous potassium acetate (15.3 g, 156.4 mmol) were added, The mixture was then heated to 90° C. and stirred for 12 hours. After cooling to room temperature, the reaction solution was diluted with about 200 mL of water, extracted three times with ethyl acetate (400 mL). The combined organic phases were washed in turn with water (80 mL) three times, saturated brine (80 mL) once, dried over anhydrous sodium sulfate and filtered. The filtrate was concentrated and purified by flash silica gel column chromatography (petroleum ether/ethyl acetate=3:1) to give the title compound 5a (8.2 g, 33.6 mmol, 43% yield in two steps) as a pale yellow solid. $^1$H NMR (400 MHz, Chloroform-d, ppm) S 8.26 (s, 1H), 4.01 (s, 3H), 3.65 (p, J=6.7 Hz, 1H), 3.06 (d, J 1.2 Hz, 4H), 1.44 (d, J=6.9 Hz, 6H).

5): 9-isopropyl-2-methoxyisoxazolo[5,4-H]quinazoline (6a)

Manganese dioxide (26.6 g, 306 mmol) was added to a solution of 5a (7.5 g, 30.6 mmol) in benzene (400 mL), and the mixture was heated to 60° C. and stirred for 24 hours. The reaction solution was filtered by suction through a Celite pad, and the filtrate was washed with ethyl acetate (300 mL) and concentrated under reduced pressure. The obtained residue was purified by flash silica gel column chromatography (petroleum ether/ethyl acetate=4:1) to give the title compound 6a (5.3 g, 21.7 mmol, 71%) as a pale yellow solid. $^1$H NMR (400 MHz, Chloroform-d, ppm) S 9.25 (s, 1H), 7.93 (d, J=8.9 Hz, 1H), 7.64 (d, J=8.9 Hz, 1H), 4.19 (s, 3H), 3.96 (dq, J=14.6, 7.2 Hz, 1H), 1.62 (d, J=6.9 Hz, 6H).

6): 2-chloro-9-isopropylisoxazolo[5,4-H]quinazoline (7a)

To a solution of 6a (5.0 g, 20.6 mmol) in DMF (120 mL) was slowly added dropwise phosphorus oxychloride (11.5 mL, 123.6 mmol) in an ice-water bath. After the dripping was completed, the reaction was heated to 100° C. and reacted for 1 hour. The reaction was put into ice-water bath again, diluted with ethyl acetate (600 mL), and aqueous sodium hydroxide solution (1 M) was slowly added dropwise with vigorous stirring to adjust the pH to about 8. The organic phase was separated, washed successively with water (80 mL) for three times, saturated brine (80 mL) once, dried (anhydrous sodium sulfate), filtered by suction, and concentrated. The resulting residue was purified by flash silica gel column chromatography (petroleum ether/ethyl acetate=8:1) to give the title compound 7a (2.7 g, 10.9 mmol, 53%) as a pale yellow solid. $^1$H NMR (400 MHz, Chloroform-d, ppm) δ 9.33 (s, 1H), 8.03 (d, J=9.9 Hz, 1H), 7.86 (d, J=9.9 Hz, 1H), 4.00 (p, J=7.7, 7.3 Hz, 1H), 1.61 (d, J=7.8 Hz, 6H).

7): Tert-butyl 4-(6-((9-isopropylisoxazolo[5,4-H]quinazolin-2-yl)amino)pyridin-3-yl)piperazin-1-carboxylate (I-1a)

To a solution of tert-butyl 4-(6-aminopyridin-3-yl)piperazin-1-carboxylate 8a (168.6 mg, 0.606 mmol) in toluene (0.8 mL) was slowly added dropwise lithium bis(trimethylsilyl)amide (0.606 mL, 1M in THF, LiHMDS). After the reaction was stirred at room temperature for 30 minutes, 7a (50 mg, 0.202 mmol) was added, and the reaction was stirred for another 4 hours. The reaction was quenched by adding aqueous saturated sodium bicarbonate solution (5 mL), and the resulting solution was extracted three times with dichloromethane (8 mL). The organic phases were combined, dried (anhydrous sodium sulfate), filtered by suction, and concentrated. The obtained residue was purified by flash silica gel column chromatography (dichloromethane/methanol=50:1) to give the title compound I-1a (71.0 mg, 0.145 mmol, 72%) as a pale yellow solid. $^1$H NMR (400 MHz, Chloroform-d, ppm) δ 9.13 (s, 1H), 8.50 (d, J=9.0 Hz, 1H), 8.16-7.93 (m, 1H), 7.83 (d, J=8.8 Hz, 1H), 7.53 (d, J=8.8 Hz, 1H), 7.37 (dd, J=9.1, 2.9 Hz, 1H), 4.07 (p, J=6.9 Hz, 1H), 3.64 (t, J=5.1 Hz, 2H), 3.14 (t, J=5.0 Hz, 2H), 1.63 (d, J=6.9 Hz, 6H), 1.56 (s, 9H).

8): 9-isopropyl-N-(5-(piperazin-1-yl)pyridin-2-yl)isoxazolo[5,4-H]quinazolin-2-amine (I-1)

I-1a (14.7 mg, 0.03 mmol) was dissolved in dichloromethane (2 mL), and a solution of hydrogen chloride in 1,4-dioxane (4 N, 0.16 mL) was added. The mixture was stirred at room temperature for 2 hours, and then filtered by suction. The obtained residue was dried in vacuum by oil pump to constant weight to give the title compound I-1 (hydrochloride, 11.9 mg, 93%) as a yellow powder. $^1$H NMR (400 MHz, methanol-d, ppm) δ 9.17 (s, 1H), 8.48 (d, J=8.9 Hz, 1H), 7.97 (nm, 1H), 7.72 (d, J=8.7 Hz, 1H), 7.49 (d, J=8.7 Hz, 11H), 7.41 (dd, J=9.0, 2.7 Hz, 11H), 3.97 (p, J=6.9 Hz, 11H), 3.61 (t, J=5.0 Hz, 2H), 3.11 (t, J=5.0 Hz, 2H), 1.59 (d, J=7.0 Hz, 6H); LC-MS (ESI), $C_{21}H_{24}N_7O$ $[M+H]^+$: m/z=390.1.

TABLE 1

Examples I-2 to I-17

| No. | Chemical structure | Chemical Name | Hydrogen spectrum ($^1H$ NMR) | LC-MS (ESI) $[M + H]^+$ |
|---|---|---|---|---|
| I-2 | 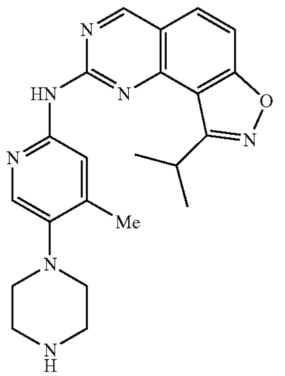 [SMILES: Cc1cc(Nc2ncc3ccc4onc(C(C)C)c4c3n2)ncc1N1CCNCC1] | 9-isopropyl-N-(4-methyl-5-(piperazin-1-yl)pyridin-2-yl)isoxazolo[5,4-H] quinazolin-2-amine | $^1H$ NMR (hydrochloride, 400 MHz, methanol-d, ppm) δ 9.20 (s, 1H), 8.51 (s, 1H), 8.32 (s, 1H), 7.99 (s, 1H), 7.57 (d, J = 8.9 Hz, 1H), 7.51 (d, J = 8.8 Hz, 1 H), 4.02 (p, J = 7.0 Hz, 1H), 3.56 (t, J = 4.9 Hz, 4H), 2.91 (t, J = 5.0 Hz, 4H), 2.53 (s, 3 H), 1.60 (d, J = 6.9 Hz, 6H) | 404.1 |
| I-3 | 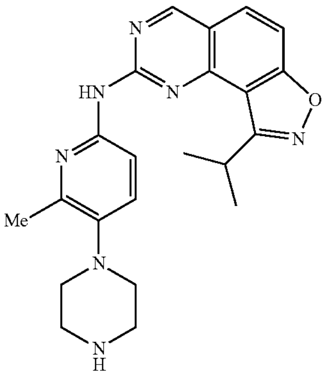 [SMILES: Cc1nc(Nc2ncc3ccc4onc(C(C)C)c4c3n2)ccc1N1CCNCC1] | 9-isopropyl-N-(6-methyl-5-(piperazin-1-yl)pyridin-2-yl)isoxazolo[5,4-H] quinazolin-2-amine | $^1$NMR (hydrochloride, 400 MHz, methanol-d, ppm) δ 9.21 (s, 1H), 8.27 (s, 1H), 8.11 (s, 1H), 7.79 (d, J = 8.9 Hz, 1H), 7.51 (d, J = 8.8 Hz, 1H), 7.38 (d, J = 8.7 Hz, 1H), 4.01 (p, J = 6.9 Hz, 1H), 3.63 (t, J = 5.0 Hz, 4H), 2.81 (t, J = 5.0 Hz, 4H), 2.54 (s, 3H), 1.61 (d, J = 6.9 Hz, 6H) | 404.2 |
| I-4 | 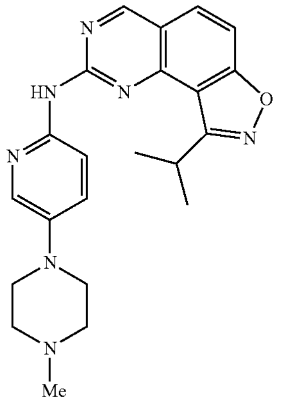 [SMILES: CCN1CCN(c2ccc(Nc3ncc4ccc5onc(C(C)C)c5c4n3)nc2)CC1] | 9-isopropyl-N-(5-(4-methylpiperazin-1-yl)pyridin-2-yl)isoxazolo [5,4-H]quinazolin-2-amine | $^1H$ NMR (400 MHz, Chloroform-d, ppm) δ 9.13 (s, 1H), 8.47 (d, J = 9.1 Hz, 1H), 8.18 (s, 1H), 8.07 (d, J = 2.9 Hz, 1H), 7.81 (d, J = 8.8 Hz, 1H), 7.51 (d, J = 8.8 Hz, 1H), 7.37 (dd, J = 9.1, 3.0 Hz, 1H), 4.07 (hept, J = 7.0 Hz, 1H), 3.28-3.20 (m, 4H), 2.68-2.60 (m, 4H), 2.39 (s, 3H), 1.62 (d, J = 6.9 Hz, 6H) | 404.2 |

TABLE 1-continued

Examples I-2 to I-17

| No. | Chemical structure | Chemical Name | Hydrogen spectrum ($^1$H NMR) | LC-MS (ESI) [M + H]$^+$ |
|---|---|---|---|---|
| I-5 | 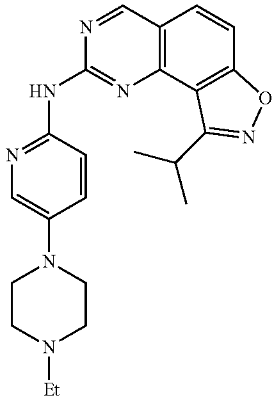 | N-(5-(4-ethylpiperazin-1-yl) pyridin-2-yl)-9-isopropylisoxazolo [5,4-H]quinazolin-2-amine | $^1$H NMR (400 MHz, Chloroform-d, ppm) δ 9.12 (s, 1H), 8.47 (d, J = 9.0 Hz, 1H), 8.12 (s, 1H), 8.06 (d, J = 2.6 Hz, 1H), 7.81 (d, J = 8.8 Hz, 1H), 7.51 (d, J = 8.8 Hz, 1H), 7.40-7.32 (m, 1H), 4.06 (p, J = 6.9 Hz, 1H), 3.24 (t, J = 4.9 Hz, 4H), 2.67 (d, J = 5.1 Hz, 4H), 2.50 (q, J = 7.2 Hz, 2H), 1.61 (d, J =6.9 Hz, 6 H), 1.15 (t, J = 7.2 Hz, 3H) | 418.3 |
| I-6 | 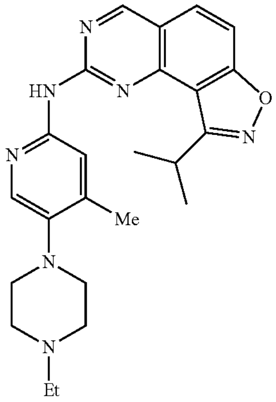 [SMILES: CCN1CCN(c2cnc(Nc3ncc4ccc5onc(C(C)C)c5c4n3)cc2C)CC1] | N-(5-(4-ethylpiperazin-1-yl)-4-methylpyridin-2-yl)-9-isopropylisoxazolo[5,4-H] quinazolin-2-amine | $^1$H NMR (400 MHz, Chloroform-d, ppm) δ 9.15 (s, 1H), 8.44 (s, 1 H), 8.34 (s, 1H), 8.09 (s, 1H), 7.83 (d, J = 8.8 Hz, 1H), 7.53 (d, J = 8.8 Hz, 1H), 4.17 (p, J = 6.9 Hz, 1H), 3.06 (d, J = 4.9 Hz, 4H), 2.67 (s, 4H), 2.54 (d, J = 7.4 Hz, 2H), 2.44 (s, 3H), 1.62 (d, J = 6.9 Hz, 6H), 1.17 (t, J = 7.2 Hz, 3H) | 432.2 |
| I-7 | 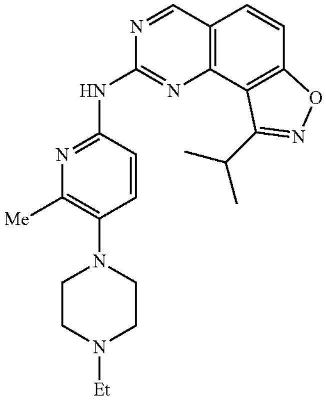 [SMILES: CCN1CCN(c2ccc(Nc3ncc4ccc5onc(C(C)C)c5c4n3)nc2C)CC1] | N-(5-(4-ethylpiperazin-1-yl)-6-methylpyridin-2-yl)-9-isopropylisoxazolo [5,4-H]quinazolin-2-amine | $^1$H NMR (400 MHz, Chloroform-d, ppm) δ 9.15 (s, 1H), 8.34 (d, J = 8.7 Hz, 1H), 8.14 (s, 1H), 7.82 (d, J = 8.8 Hz, 1H), 7.52 (d, J = 8.8 Hz, 1H), 7.45 (d, J = 8.7 Hz, 1H), 4.06 (p, J = 6.9 Hz, 1H), 2.99 (d, J = 4.9 Hz, 4H), 2.65 (s, 4H), 2.54 (m, 2 H), 2.51 (s, 3H), 1.61 (d, J = 7.0 Hz, 6H), 1.17 (d, J = 7.1 Hz, 3H) | 432.1 |

TABLE 1-continued

| Examples I-2 to I-17 | | | | |
|---|---|---|---|---|
| No. | Chemical structure | Chemical Name | Hydrogen spectrum ($^1$H NMR) | LC-MS (ESI) [M + H]$^+$ |
| I-8 | 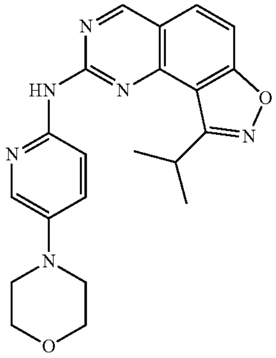 | 9-isopropyl-N-(5-morpholinopyridin-2-yl)isoxazolo[5,4-H] quinazolin-2-amine | $^1$H NMR (400 MHz, Chloroform-d, ppm) δ 9.13 (s, 1H), 8.51 (d, J = 9.1 Hz, 1H), 8.04 (d, J = 2.9 Hz, 1H), 7.83 (d, J = 8.8 Hz, 1H), 7.53 (d, J = 8.8 Hz, 1H), 7.36 (dd, J = 9.1, 2.9 Hz, 1H), 4.07 (dq, J = 14.3, 7.0 Hz, 1H), 3.99-3.83 (m, 4H), 3.27-3.11 (m, 4H), 1.62 (d, J = 6.9 Hz, 6H) | 391.1 |
| I-9 | 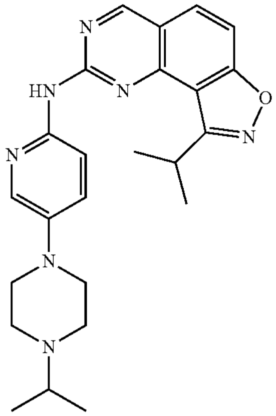 [SMILES: CC(C)c1noc2ccc3cnc(Nc4ccc(N5CCN(C(C)C)CC5)cn4)nc3c12] | 9-isopropyl-N-(5-(4-isopropylpiperazin-1-yl)pyridin-2-yl)isoxazolo [5,4-H]quinazolin-2-amine | $^1$H NMR (400 MHz, Chloroform-d, ppm) δ 9.12 (s, 1H), 8.47 (d, J = 9.0 Hz, 1H), 8.13-8.02 (m, 2H), 7.81 (d, J = 8.8 Hz, 1H), 7.51 (d, J = 8.8 Hz, 1H), 7.37 (dd, J = 9.1, 3.0 Hz, 1H), 4.07 (p, J = 6.9 Hz, 1H), 3.24 (s, 4H), 2.74 (s, 5H), 1.62 (d, J = 6.9 Hz, 6H), 1.12 (d, J = 6.5 Hz, 6H) | 432.2 |
| I-10 | 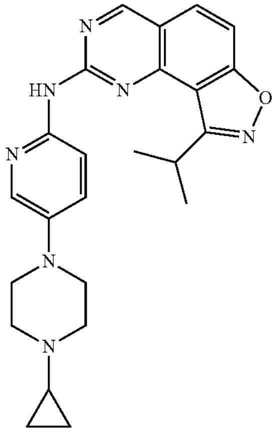 [SMILES: CC(C)c1noc2ccc3cnc(Nc4ccc(N5CCN(C6CC6)CC5)cn4)nc3c12] | N-(5-(4-eyelopropylpiperazin-1-yl)pyridin-2-yl)-9-isopropylisoxazolo[5,4-H] quinazolin-2-amine | $^1$H NMR (400 MHz, Chloroform-d, ppm) δ 9.13 (s, 1H), 8.46 (d, J = 9.1 Hz, 1H), 8.16 (s, 1H), 8.06 (d, J = 3.0 Hz, 1H), 7.81 (d, J = 8.8 Hz, 1H), 7.51 (d, J = 8.9 Hz, 1H), 7.37 (dd, J = 9.1, 3.0 Hz, 1H), 4.07 (p, J = 7.0 Hz, 1H), 3.19 (t, J = 5.0 Hz, 4H), 2.83 (t, J = 5.0 Hz, 4H), 1.71 (t, J = 3.7 Hz, 1H), 1.62 (d, J = 6.9 Hz, 6H), 0.54-0.45 (m, 4H) | 430.2 |

TABLE 1-continued

| Examples I-2 to I-17 | | | | |
|---|---|---|---|---|
| No. | Chemical structure | Chemical Name | Hydrogen spectrum ($^1$H NMR) | LC-MS (ESI) $[M + H]^+$ |
| I-11 | 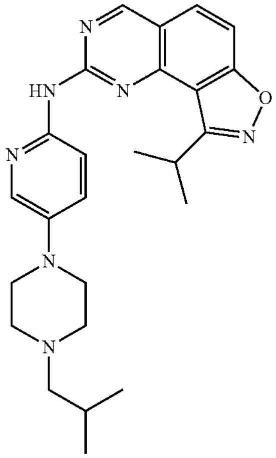 [SMILES: CC(C)CN1CCN(c2ccc(Nc3ncc4ccc5onc(C(C)C)c5c4n3)nc2)CC1] | N-(5-(4-isobutylpiperazin-1-yl) pyridin-2-yl)-9-isopropylisoxazolo[5,4-H] quinazolin-2-amine | $^1$H NMR (400 MHz, Chloroform-d, ppm) δ 9.13 (s, 1H), 8.47 (d, J = 9.0 Hz, 1H), 8.15 (s, 1H), 8.07 (d, J = 2.9 Hz, 1H), 7.81 (d, J = 8.8 Hz, 1H), 7.51 (d, J = 8.8 Hz, 1H), 7.36 (dd, J = 9.1, 3.0 Hz, 1H), 4.07 (p, J = 6.9 Hz, 1 H), 3.22 (t, J = 5.0 Hz, 4H), 2.66-2.53 (m, 4H), 2.17 (d, J = 7.3 Hz, 2H), 1.84 (dt, J = 13.6, 6.8 Hz, 1H), 1.62 (d, J = 6.9 Hz, 6H), 0.94 (d, J = 6.6 Hz, 6H) | 446.1 |
| I-12 | 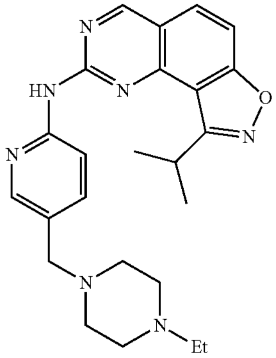 [SMILES: CCN1CCN(Cc2ccc(Nc3ncc4ccc5onc(C(C)C)c5c4n3)nc2)CC1] | N-(5-((4-ethylpiperazin-1-yl) methyl)pyridin-2-yl)-9-isopropylisoxazolo[5,4-H] quinazolin-2-amine | $^1$H NMR (400 MHz, Chloroform-d, ppm) δ 9.18 (s, 1H), 8.59 (d, J = 8.5 Hz, 1H), 8.37 (s, 1H), 8.29 (d, J = 2.3 Hz, 1H), 7.85 (d, J = 8.8 Hz, 1H), 7.75 (dd, J = 8.5, 2.3 Hz, 1H), 7.56 (d, J = 8.8 Hz, 1H), 4.15-4.04 (m, 1H), 3.54 (s, 2H), 2.54 (brs, 6H), 2.44 (q, J = 7.2 Hz, 2H), 1.64 (d, J = 6.9 Hz, 6H), 1.59 (m, 2H), 1.09 (t, J = 7.2 Hz, 3H) | 432.0 |
| I-13 | 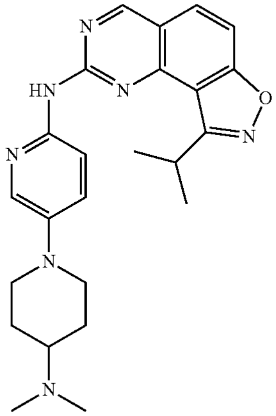 [SMILES: CC(C)c1noc2ccc3cnc(Nc4ccc(N5CCC(N(C)C)CC5)cn4)nc3c12] | N-(5-(4-(dimethylamino) piperidin-1-yl)pyridin-2-yl)-9-isopropylisoxazolo [5,4-H]quinazolin-2-amine | $^1$H NMR (400 MHz, Chloroform-d, ppm) δ 9.12 (s, 1H), 8.46 (d, J = 9.0 Hz, 1H), 8.13-8.04 (m, 2H), 7.81 (d, J = 8.9 Hz, 1H), 7.51 (d, J = 8.9 Hz, 1H), 7.38 (dd, J = 9.1, 3.0 Hz, 1H), 4.07 (p, J = 6.9 Hz, 1H), 3.69 (d, J = 12.1 Hz, 2H), 2.79 (td, J = 12.0, 2.4 Hz, 2H), 2.36 (s, 6H), 2.30 (m, 1H), 2.00 (d, J = 12.6 Hz, 2H), 1.73 (td, J = 12.0, 4.0 Hz, 2H), 1.62 (d, J = 6.9 Hz, 6H) | 432.3 |

TABLE 1-continued

Examples I-2 to I-17

| No. | Chemical structure | Chemical Name | Hydrogen spectrum ($^1$H NMR) | LC-MS (ESI) $[M + H]^+$ |
|---|---|---|---|---|
| I-14 | 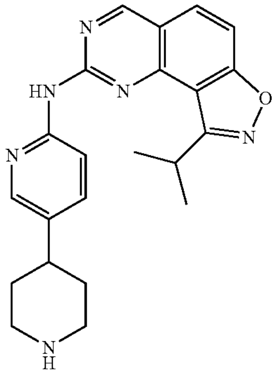 [SMILES: CC(C)c1noc2ccc3cnc(Nc4ccc(C5CCNCC5)cn4)nc3c12] | 9-isopropyl-N-(5-(piperidin-4-yl)pyridin-2-yl)isoxazolo[5,4-H] quinazolin-2-amine | $^1$H NMR (hydrochloride, 400 MHz, methanol-d, ppm) δ 9.15 (s, 1H), 8.60-8.52 (m, 2H), 8.25 (d, J = 2.4 Hz, 1H), 7.81 (d, J = 8.8 Hz, 1H), 7.57 (dd, J = 8.6, 2.4 Hz, 1H), 7.52 (d, J = 8.8 Hz, 1H), 4.23 (s, 2H), 4.11-4.01 (m, 1H), 2.83 (s, 2H), 2.71 (s, 1H), 1.81 (d, J = 13.0 Hz, 2H), 1.65 (td, J = 13.0, 4.6 Hz, 2H), 1.61 (d, J = 6.9 Hz, 6H) | 389.3 |
| I-15 | 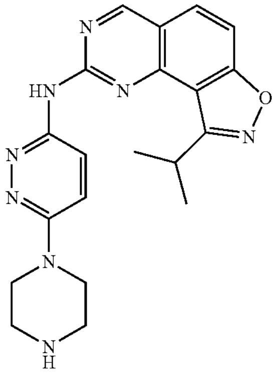 [SMILES: CC(C)c1noc2ccc3cnc(Nc4ccc(N5CCNCC5)nn4)nc3c12] | 9-isopropyl-N-(6-(piperazin-1-yl)pyridazin-3-yl)isoxazolo[5,4-H]quinazolin-2-amine | $^1$H NMR (hydrochloride, 400 MHz, methanol-d, ppm) δ 9.15 (s, 1H), 8.63 (d, J = 9.8 Hz, 1H), 7.81 (d, J = 8.9 Hz, 1H), 7.54 (d, J = 8.8 Hz, 1H), 7.05 (d, J = 9.8 Hz, 1H), 4.01 (p, J = 7.0 Hz, 1H), 3.60 (s, 8H), 1.58 (d, J = 7.0 Hz, 6H) | 391.2 |
| I-16 | 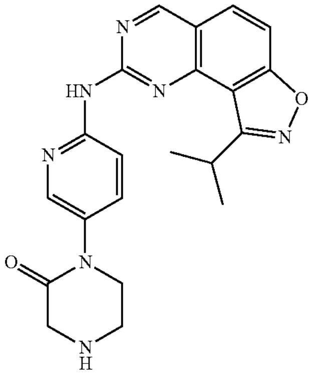 [SMILES: CC(C)c1noc2ccc3cnc(Nc4ccc(N5CCNCC5=O)cn4)nc3c12] | 1-(6-((9-isopropylisoxazolo[5,4-H]quinazolin-2-yl)amino) pyridin-3-yl)piperazin-2-one | $^1$H NMR (hydrochloride, 400 MHz, methanol-d, ppm) δ 9.18 (s, 1H), 8.71 (d, J = 8.9 Hz, 1H), 8.53 (s, 1H), 8.31 (d, J = 2.6 Hz, 1H), 7.84 (d, J = 8.9 Hz, 1H), 7.72 (dd, J = 8.9, 2.7 Hz, 1H), 7.51 (d, J = 8.9 Hz, 1H), 4.28 (s, 2H), 4.03 (p, J = 6.9 Hz, 1H), 3.85-3.76 (m, 4H), 1.61 (d, J = 6.9 Hz, 6H) | 404.2 |
| I-17 | 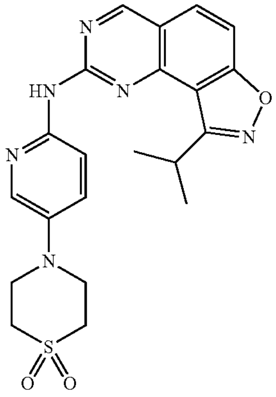 [SMILES: CC(C)c1noc2ccc3cnc(Nc4ccc(N5CCS(=O)(=O)CC5)cn4)nc3c12] | 4-(6-((9-isopropylisoxazolo[5,4-H]quinazolin-2-yl)amino) pyridin-3-yl)thiomorpholine 1,1-dioxide | $^1$H NMR (400 MHz, Chloroform-d, ppm) δ 9.16 (s, 1H), 8.57 (d, J = 9.0 Hz, 1H), 8.22 (s, 1H), 8.11 (d, J = 3.0 Hz, 1H), 7.85 (d, J = 8.8 Hz, 1H), 7.56 (d, J = 8.8 Hz, 1H), 7.40 (dd, J = 9.0, 3.0 Hz, 1H), 4.06 (p, J = 7.0 Hz, 1H), 3.80 (t, J = 5.3 Hz, 4H), 3.21 (t, J = 5.2 Hz, 4H), 1.63 (d, J = 6.9 Hz, 6H) | 439.2 |

By referring to the synthetic method of I-1 in Example I-1, compounds 1-2 (hydrochloride, 60.3 mg, 137.4 μmmol, 68%), I-3 (hydrochloride, 45.2 mg, 103.0 μmmol, 51%), I-14 (hydrochloride, 67.7 mg, 159.6 μmmol, 79%), I-15 (hydrochloride, 47.3 mg, 111.1 μmmol, 55%), and I-16 (hydrochloride, 16.9 mg, 38.4 μmmol, 19%) were prepared from 7a (50 mg, 202.0 μmmol).

By referring to the synthetic method of I-1a in Example I-1, compounds I-4 (38.1 mg, 94.5 μmmol, 46.8%), I-5 (68.7 mg, 164.7 μmmol, 81.6%), I-6 (56.4 mg, 130.8 μmmol, 64.8%), I-7 (38.5 mg, 89.3 μmmol, 44.2%), I-8 (45.4 mg, 116.4 μmmol, 57.6%), I-9 (50.4 mg, 116.9 μmmol, 57.9%), I-10 (30.0 mg, 69.9 μmmol, 34.6%), I-11 (50.2 mg, 112.8 μmmol, 55.8%), I-12 (57.3 mg, 132.9 μmmol, 65.8%), I-13 (17.4 mg, 40.4 μmmol, 20.0%), and I-17 (15.1 mg, 34.5 μmmol, 17.1%) were prepared from 7a (50 mg, 202.0 μmmol).

Preparation of intermediate 2-chloro-9-isobutyl-isoxazolo[5,4-H]quinazoline (7b)

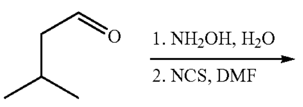

1b

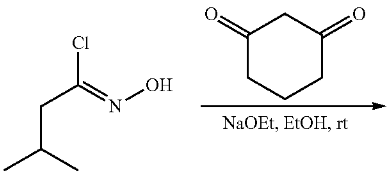

2b

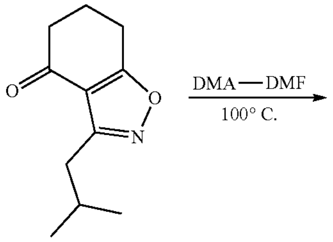

3b

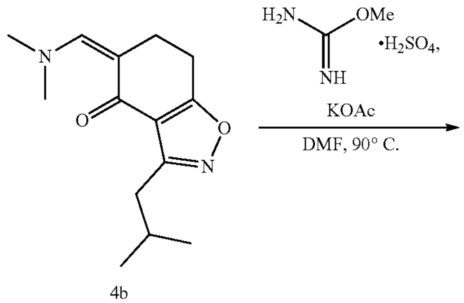

4b

-continued

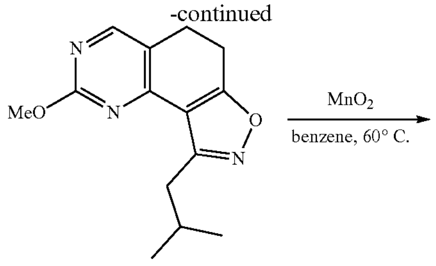

5b

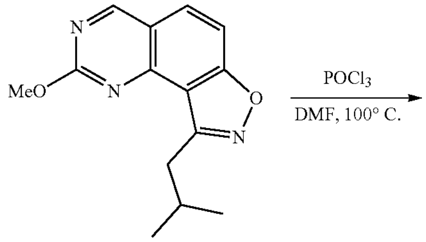

6b

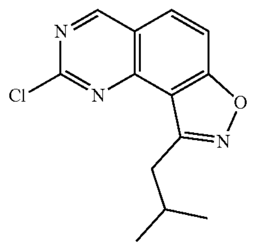

7b

By referring to the synthetic method of 7a in Example I-1, 7b (1.9 g, 7.28 mmol, 7-step total yield: 6.3%) was prepared from isovaleraldehyde 1b (10 g, 116.1 mmol) through 7-step reaction.

3b LC-MS (ESI), $C_{11}H_{16}NO_2$ $[M+H]^+$: m/z=194.1.

4b LC-MS (ESI), $C_{14}H_{21}N_2O_2$ $[M+H]^+$: m/z=249.2.

5b $^1H$ NMR (400 MHz, Chloroform-d) δ 8.23 (d, J=1.1 Hz, 1H), 3.98 (d, J=1.2 Hz, 3H), 3.05 (d, J=1.0 Hz, 4H), 2.91 (d, J=1.3 Hz, 2H), 2.26 (ddd, J=14.3, 7.2, 6.0 Hz, 1H), 0.97 (dd, J=6.6, 1.2 Hz, 6H).

6b $^1H$ NMR (400 MHz, Chloroform-d) δ 9.24 (s, 1H), 7.92 (d, J=8.9 Hz, 1H), 7.63 (d, J=8.9 Hz, 1H), 4.19 (s, 3H), 3.26 (d, J=7.2 Hz, 2H), 2.54 (dp, J=13.7, 6.8 Hz, 1H), 1.06 (d, J=6.6 Hz, 6H).

7b $^1H$ NMR (400 MHz, Chloroform-d) δ 9.32 (s, 1H), 8.02 (d, J=8.9 Hz, 1H), 7.85 (d, J=9.0 Hz, 1H), 3.26 (d, J=7.0 Hz, 2H), 2.45 (dt, J=13.6, 6.8 Hz, 1H), 1.09 (d, J=6.7 Hz, 6H).

TABLE 2

| Examples I-18 to I-21 | | | | |
|---|---|---|---|---|
| No. | Chemical structure | Chemical Name | Hydrogen spectrum ($^1H$ NMR) | LC-MS (ESI) $[M + H]^+$ |
| I-18 | 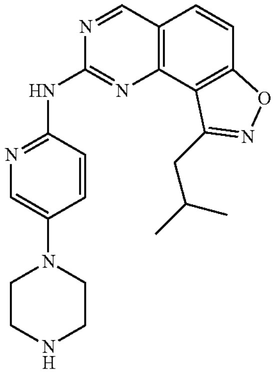 [SMILES: CC(C)Cc1noc2ccc3cnc(Nc4ccc(N5CCNCC5)cn4)nc3c12] | 9-isobutyl-N-(5-(piperazin-1-yl) pyridin-2-yl)isoxazolo[5,4-H]quinazolin-2-amine | $^1H$ NMR (hydrochloride, 400 MHz, methanol-d, ppm) δ 9.11 (s, 1H), 8.51 (d, J = 9.0 Hz, 1H), 8.08 (s, 1H), 8.03 (d, J = 2.9 Hz, 1H), 7.81 (d, J = 8.9 Hz, 1H), 7.51 (d, J = 8.8 Hz, 1H), 7.36 (dd, J = 9.0, 3.0 Hz, 1H), 3.65-3.56 (m, 4H), 3.29 (d, J = 7.4 Hz, 2H), 3.09 (t, J = 5.1 Hz, 4H), 2.43 (dq, J = 13.6, 6.8 Hz, 1H), 1.03 (d, J = 6.7 Hz, 6H) | 404.3 |
| I-19 | 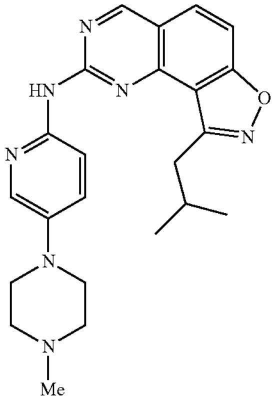 [SMILES: CC(C)Cc1noc2ccc3cnc(Nc4ccc(N5CCN(C)CC5)cn4)nc3c12] | 9-isobutyl-N-(5-(4-methylpiperazin-1-yl)pyridin-2-yl)isoxazolo[5,4-H] quinazolin-2-amine | $^1$NMR (400 MHz, Chloroform-d, ppm) δ 9.13 (s, 1H), 8.45 (d, J = 9.0 Hz, 1H), 8.18 (s, 1H), 8.08 (d, J = 2.9 Hz, 1H), 7.81 (d, J = 8.9 Hz, 1H), 7.51 (d, J = 8.9 Hz, 1H), 7.39 (dd, J = 9.0, 3.0 Hz, 1H), 3.33 (d, J = 7.4 Hz, 2H), 3.27-3.17 (m, 4H), 2.63 (dd, J = 6.0, 4.0 Hz, 4H), 2.48 (dq, J = 13.6, 6.8 Hz, 1H), 2.38 (s, 3H), 1.05 (d, J = 6.6 Hz, 6H) | 418.2 |
| I-20 | 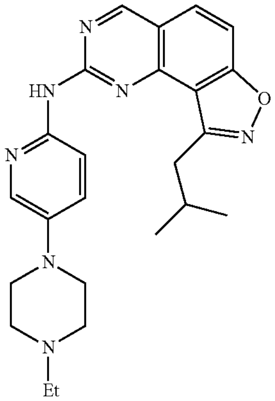 [SMILES: CCN1CCN(c2ccc(Nc3ncc4ccc5onc(CC(C)C)c5c4n3)nc2)CC1] | N-(5-(4-ethylpiperazin-1-yl)pyridin-2-yl)-9-isobutylisoxazolo[5,4-H] quinazolin-2-amine | $^1$NMR (400 MHz, Chloroform-d, ppm) δ 9.13 (s, 1H), 8.45 (d, J = 9.1 Hz, 1H), 8.17 (s, 1H), 8.08 (d, J = 2.9 Hz, 1H), 7.81 (d, J = 8.8 Hz, 1H), 7.52 (s, 1H), 7.40 (dd, J = 9.1, 3.0 Hz, 1H), 3.33 (d, J = 7.4 Hz, 2H), 3.27-3.21 (m, 4H), 2.67 (t, J = 5.1 Hz, 4H), 2.50 (dq, J = 10.1, 7.0 Hz, 2H), 1.15 (t, J = 7.2 Hz, 3H), 1.05 (d, J = 6.6 Hz, 6H) | 432.3 |

TABLE 2-continued

| Examples I-18 to I-21 | | | | |
|---|---|---|---|---|
| No. | Chemical structure | Chemical Name | Hydrogen spectrum ($^1$H NMR) | LC-MS (ESI) $[M + H]^+$ |
| I-21 | 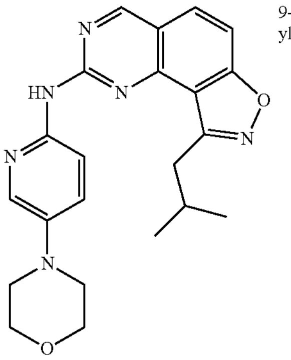 | 9-isobutyl-N-(5-morpholinopyridin-2-yl)isoxazolo[5,4-H]quinazolin-2-amine | $^1$H NMR (400 MHz, Chloroform-d, ppm) δ 9.14 (s, 1H), 8.48 (d, J = 9.0 Hz, 1H), 8.26 (s, 1H), 8.08 (d, J = 2.9 Hz, 1H), 7.82 (d, J = 8.8 Hz, 1H), 7.52 (d, J = 8.9 Hz, 1H), 7.38 (dd, J = 9.1, 3.0 Hz, 1H), 3.96-3.87 (m, 4H), 3.33 (d, J = 7.4 Hz, 2H), 3.21-3.14 (m, 4H), 2.48 (hept, J = 6.8 Hz, 1H), 1.06 (d, J = 6.6 Hz, 6H) | 405.1 |

By referring to the synthetic method of I-1 in Example I-1, compound I-18 (hydrochloride, 65.8 mg, 149.8 μmmol, 78%) was prepared from 7b (50 mg, 192.0 μmmol).

By referring to the synthetic method of I-1a in Example I-1, compounds I-19 (51.1 mg, 122.4 μmmol, 63.8%), I-20 (68.4 mg, 158.7 μmmol, 82.7%), and I-21 (53.3 mg, 131.9 μmmol, 68.7%) were prepared from 7b (50 mg, 192.0 μmmol).

Preparation of intermediate 2-chloro-9-cyclopentyl-isoxazolo[5,4-H]quinazoline (7c)

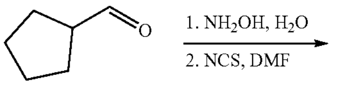

1c

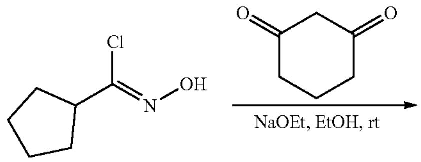

2c

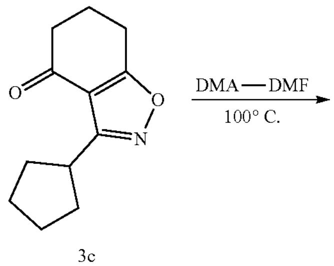

3c

-continued

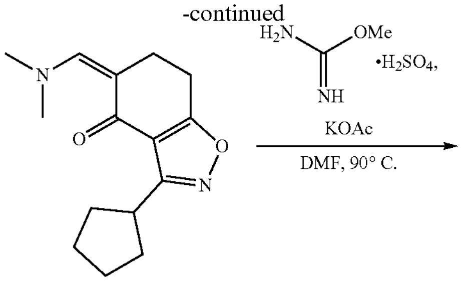

4c

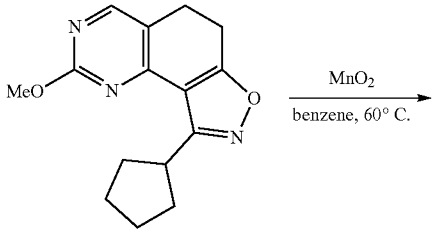

5c

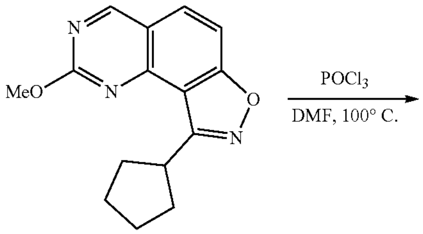

6c

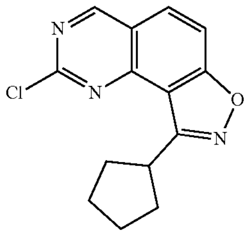

7c

By referring to the synthetic method of 7a in Example I-1, 7c (0.82 g, 3.0 mmol, 7-step total yield: 5.9%) was prepared from cyclopentanecarbaldehyde 1c (5 g, 51.0 mmol) through 7-step reaction.

3c $^1H$ NMR (400 MHz, Chloroform-d) δ 3.01 (t, J=6.3 Hz, 2H), 2.53 (dd, J=7.2, 5.7 Hz, 2H), 2.46 (dq, J=13.3, 6.6 Hz, 2H), 2.38 (dq, J=13.3, 6.6 Hz, 2H), 2.22 (p, J=6.7 Hz, 1H), 2.09 (td, J=13.8, 6.8 Hz, 2H), 1.95 (d, J=8.1 Hz, 4H).

4c LC-MS (ESI), $C_{15}H_{21}N_2O_2$ $[M+H]^+$: m/z=261.3.

5c $^1H$ NMR (400 MHz, Chloroform-d) δ 8.23 (s, 1H), 3.98 (s, 3H), 3.05 (d, J 12 Hz, 4H), 3.26 (d, J=7.2 Hz, 2H), 2.40 (dq, J=13.2, 6.4 Hz, 2H), 2.32 (m, 1H), 2.12 (td, J=13.2, 6.4 Hz, 2H), 1.91 (d, J=8.0 Hz, 4H).

6c $^1H$ NMR (400 MHz, Chloroform-d) δ 9.24 (s, 1H), 7.90 (d, J=8.9 Hz, 1H), 7.60 (d, J=8.9 Hz, 1H), 4.21 (s, 3H), 3.93 (p, J=6.4 Hz, 1H), 2.48 (dq, J=13.2, 6.4 Hz, 2H), 2.21 (td, J=13.2, 6.4 Hz, 2H), 2.01 (d, J=7.2 Hz, 4H).

7c $^1H$ NMR (400 MHz, Chloroform-d) δ 9.33 (s, 1H), 8.04 (d, J=8.8 Hz, 1H), 7.86 (d, J=8.0 Hz, 1H), 4.01 (m, 1H), 2.50 (dq, J=13.0, 6.0 Hz, 2H), 2.25 (td, J=13.0, 6.0 Hz, 2H), 2.08 (d, J=7.2 Hz, 4H).

TABLE 3

Examples I-22 to I-23

| No. | Chemical structure | Chemical Name | Hydrogen spectrum ($^1H$ NMR) | LC-MS (ESI) $[M + H]^+$ |
|---|---|---|---|---|
| I-22 | 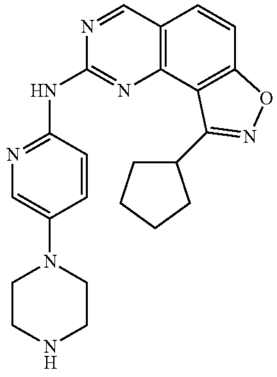 [SMILES: c1cc(Nc2ncc3ccc4onc(C5CCCC5)c4c3n2)ncc1N1CCNCC1] | 9-cyclopentyl-N-(5-(piperazin-1-yl) pyridin-2-yl)isoxazolo[5,4-H] quinazolin-2-amine | $^1H$ NMR (hydrochloride, 400 MHz, methanol-d, ppm) δ 8.82 (s, 1H), 8.28 (d, J = 8.8 Hz, 1H), 7.83 (m, 1H), 7.72 (d, J = 8.8 Hz, 1H), 7.49 (d, J = 8.7 Hz, 1H), 7.36 (dd, J = 8.9, 2.7 Hz, 1H), 3.91 (p, J = 6.9 Hz, 1H), 3.61 (t, J = 4.6 Hz, 2H), 3.11 (t, J = 4.6 Hz, 2H), 2.51 (dq, J = 13.0, 6.8 Hz, 2H), 2.25 (td, J = 13.0, 6.8 Hz, 2H), 2.11 (d, J = 7.0 Hz, 4H) | 416.2 |
| I-23 | 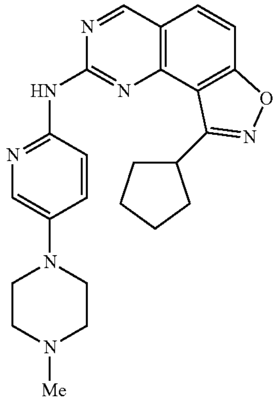 [SMILES: CN1CCN(c2ccc(Nc3ncc4ccc5onc(C6CCCC6)c5c4n3)nc2)CC1] | 9-cyclopentyl-N-(5-(4-methylpiperazin-1-yl)pyridin-2-yl)isoxazolo[5,4-H]quinazolin-2-amine | $^1H$NMR (400 MHz, Chloroform-d) δ 9.10 (s, 1H), 8.56 (d, J = 8.9 Hz, 1H), 8.13 (s, 1H), 8.00 (d, J = 2.8 Hz, 1H), 7.78 (d, J = 8.9 Hz, 1H), 7.49 (d, J = 8.8 Hz, 1H), 7.29 (dd, J =9.0, 2.9 Hz, 1H), 4.17 (p, J = 6.8 Hz, 1H), 3.30-3.24 (m, 4H), 2.61-2.57 (m, 4H), 2.42 (s, 3H), 2.50 (dq, J = 13.4, 6.4 Hz, 2H), 2.12 (td, J = 13.4 6.4 Hz, 2H), 1.96 (d, J = 7.2 Hz, 4H) | 430.1 |

By referring to the synthetic method of I-1 in Example I-1, compound I-22 (hydrochloride, 65.8 mg, 149.8 μmmol, 78%) was prepared from 7c (50 mg, 192.0 μmmol).

By referring to the synthetic method of I-1a in Example I-1, compound I-23 (51.1 mg, 122.4 μmmol, 63.8%) was prepared from 7c (50 mg, 192.0 μmmol).

Example I-24

Preparation of 9-isopropyl-N-(5-(piperazin-1-yl) pyridin-2-yl)-5,6-dihydroisoxazolo[5,4-h]quinazolin-2-amine hydrochloride

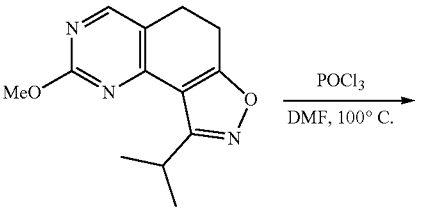

5a

-continued

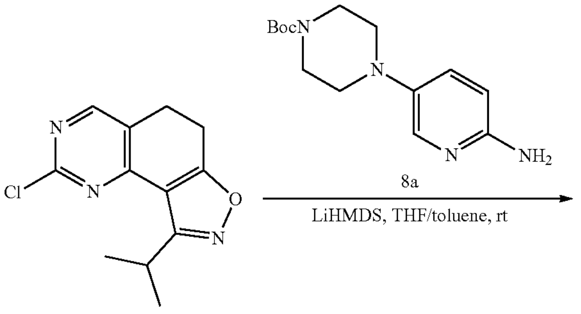

7d

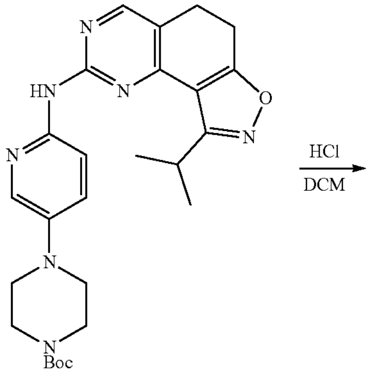

I-24a

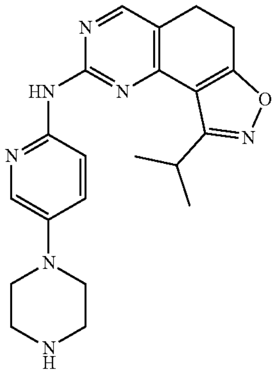

I-24

1): 2-chloro-9-isopropyl-5,6-dihydroisoxazolo[5,4-H]quinazoline (7d)

To a solution of 5a (600 mg, 2.45 mmol) in DMF (15 mL) was slowly added dropwise phosphorus oxychloride (2.28 mL, 24.5 mmol) in an ice-water bath. After the dripping was completed, the reaction was heated to 100° C. and reacted for 3 hours. The reaction was put into ice-water bath again, diluted with ethyl acetate (600 mL), and aqueous sodium hydroxide solution (1 M) was slowly added dropwise with vigorous stirring to adjust the pH to about 8. The organic phase was separated, washed successively with water (20 mL) for three times, saturated brine (30 mL) once, dried (anhydrous sodium sulfate), filtered by suction, and concentrated. The resulting residue was purified by flash silica gel column chromatography (petroleum ether/ethyl acetate=8:1) to give the title compound 7d (294.0 mg, 1.18 mmol, 48%) as a pale yellow solid. $^{1}H$ NMR (400 MHz, Chloroform-d, ppm) δ 8.34 (s, 1H), 3.63 (p, J=6.9 Hz, 1H), 3.12 (s, 4H), 1.43 (d, J=6.9 Hz, 6H).

2): Tert-butyl 4-(6-(((9-isopropyl-5,6-dihydroisoxazolo[5,4-H]quinazolin-2-yl)amino)pyridin-3-yl)piperazin-1-carboxylate (I-24a)

To a solution of tert-butyl 4-(6-aminopyridin-3-yl)piperazin-1-carboxylate 8a (84.9 mg, 0.305 mmol) in toluene (0.8 mL) was slowly added dropwise lithium bis(trimethylsilyl) amide (0.305 mL, 1M in THF, LiHMDS). After the reaction was stirred at room temperature for 30 minutes, 7d (50.5 mg, 0.203 mmol) was added, and the reaction was stirred for another 4 hours. The reaction was quenched by adding aqueous saturated sodium bicarbonate solution (5 mL), and the resulting solution was extracted three times with dichloromethane (8 mL). The organic phases were combined, dried (anhydrous sodium sulfate), filtered by suction, and concentrated. The obtained residue was purified by flash silica gel column chromatography (dichloromethane/methanol=50:1) to give the title compound I-24a (65.8 mg, 0.134 mmol, 66.6%) as a pale yellow solid. $^{1}H$ NMR (400 MHz, Chloroform-d, ppm) δ 8.22 (s, 1H), 7.93 (s, 1H), 7.32 (dd, J=9.1, 3.0 Hz, 1H), 7.26 (s, 1H), 3.65 (m, 1H), 3.60 (t, J=5.1 Hz, 4H), 3.09 (t, J=5.1 Hz, 4H), 3.03 (s, 2H), 1.49 (s, 9H), 1.43 (d, J=6.9 Hz, 6H).

3): 9-isopropyl-N-(5-(piperazin-1-yl)pyridin-2-yl)-5,6-dihydroisoxazolo[5,4-H]quinazolin-2-amine (I-24)

I-24a (65.8 mg, 0.134 mmol) was dissolved in dichloromethane (2 mL), and a solution of hydrogen chloride in 1,4-dioxane (4 N, 0.67 mL) was added. The mixture was stirred at room temperature for 2 hours, and then filtered by suction. The obtained residue was dried in vacuum by oil pump to constant weight to give the title compound I-24 (hydrochloride, 53.2 mg, 93%) as a yellow powder. $^{1}H$ NMR (400 MHz, methanol-d, ppm) δ 8.18 (s, 1H), 7.91 (s, 1H), 7.29 (dd, J=9.1, 3.0 Hz, 1H), 7.18 (s, 1H), 3.68 (p, J 7.0 Hz, 1H), 3.57 (t, J=5.1 Hz, 4H), 3.05 (t, J=5.1 Hz, 4H), 2.99 (s, 2H), 1.40 (d, J=6.9 Hz, 6H).

TABLE 4

| Examples I-25 to I-26 | | | | |
|---|---|---|---|---|
| No. | Chemical structure | Chemical Name | Hydrogen spectrum ($^1H$ NMR) | LC-MS (ESI) $[M + H]^+$ |
| I-25 | 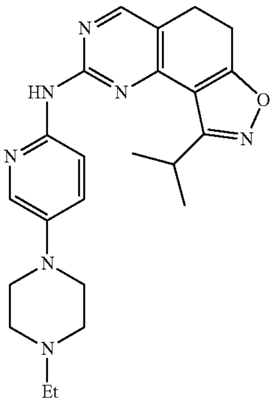 [SMILES: CCN1CCN(c2ccc(Nc3ncc4c(n3)-c3c(C(C)C)noc3CC4)nc2)CC1] | N-(5-(4-ethylpiperazin-1-yl)pyridin-2-yl)-9-isopropyl-5,6-dihydroisoxazolo[5,4-H]quinazolin-2-amine | $^1H$ NMR (400 MHz, Chloroform-d, ppm) δ 8.23-8.18 (m, 2H), 8.00 (d, J = 3.0 Hz, 1H), 7.74 (s, 1H), 7.31 (dd, J = 9.1, 3.0 Hz, 1H), 3.68 (p, J = 6.9 Hz, 1H), 3.25-3.15 (m, 4H), 3.07-3.00 (m, 4H), 2.71-2.60 (m, 4H), 2.55-2.47 (m, 2H), 1.44 (d, J = 6.9 Hz, 6H), 1.14 (t, J = 7.2 Hz, 3H) | 420.3 |
| I-26 | 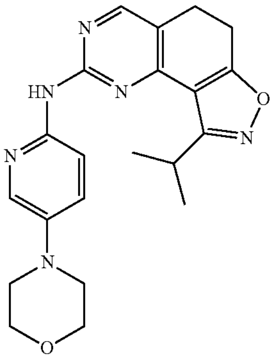 [SMILES: CC(C)c1noc2c1-c1nc(Nc3ccc(N4CCOCC4)cn3)ncc1CC2] | 9-isopropyl-N-(5-morpholinopyridin-2-yl)-5,6-dihydroisoxazolo[5,4-H]quinazolin-2-amine | $^1H$ NMR (400 MHz, Chloroform-d, ppm) δ 8.24 (d, J = 9.1 Hz, 1H), 8.22 (s, 1H), 7.98 (d, J = 3.0 Hz, 1H), 7.77 (s, 1H), 7.29 (dd, J = 9.1, 3.0 Hz, 1H), 3.92-3.86 (m, 4H), 3.69 (p, J = 6.9 Hz, 1H), 3.16-3.11 (m, 4H), 3.06-3.02 (m, 4H), 1.45 (d, J = 6.9 Hz, 6H) | 393.2 |

By referring to the synthetic method of I-24a in Example I-24, compound I-25 (60.3 mg, 143.8 μmmol, 71.6%) and I-26 (45.2 mg, 115.2 μmmol, 57.4%) were prepared from 7d (50 mg, 200.8 μmol).

Example I-27

Preparation of 9-isopropyl-N-(4-(piperazin-1-yl)phenyl)isoxazolo[5,4-H]quinazolin-2-amine (I-27)

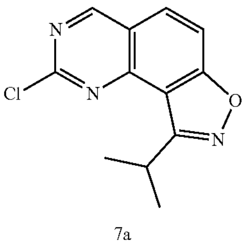

7a

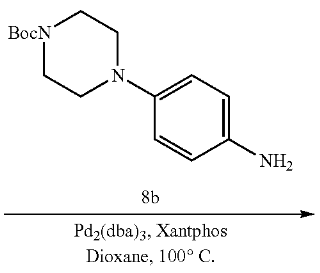

-continued

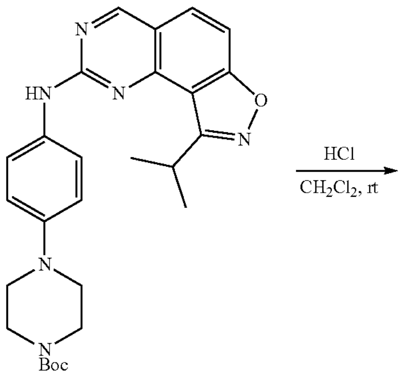

I-27a

-continued

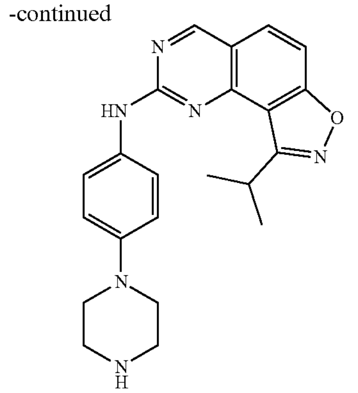

I-27

1): tert-butyl 4-(4-((9-isopropylisoxazolo[5,4-H] quinazolin-2-yl)amino)phenyl)piperazin-1-carboxylate (I-27a)

To a solution of 7a (40 mg, 0.162 mmol) and 8b (89.8 mg, 0.324 mmol) in 1,4-dioxane (1.5 mL) was added tris(dibenzylideneacetone)dipalladium (29.7 mg, 20 mol %) and 4,5-bis(diphenylphosphino)-9,9-dimethylxanthene (23.4 mg, 40.5 μmol) at room temperature. After the addition was completed, the atmosphere was replaced with argon twice, and the temperature was raised to 100° C. and the tube was sealed to react for 4 hours. After cooling to room temperature, the reaction solution was diluted with ethyl acetate (5 mL) and aqueous half-saturated sodium bicarbonate solution (8 mL). The organic layer was separated, and the aqueous layer was extracted with ethyl acetate (5 mL) for 3 times. The organic layers were combined, washed with saturated brine (5 mL), dried over anhydrous sodium sulfate, filtered by suction, and concentrated. The obtained residue was purified by flash silica gel column chromatography (dichloromethane/methanol=80:1 to 20:1) to give the title compound I-27a (29.8 mg, 61.0 μmol, 37.7%) as a pale yellow solid. $^1$H NMR (400 MHz, Chloroform-d, ppm) δ 9.04 (s, 1H), 7.77 (d, J=8.8 Hz, 1H), 7.71-7.65 (m, 2H), 7.46 (d, J=8.8 Hz, 1H), 7.34 (s, 1H), 7.06-6.95 (m, 2H), 4.03 (p, J=6.9 Hz, 1H), 3.63 (t, J=5.1 Hz, 4H), 3.13 (t, J=5.2 Hz, 4H), 1.57 (d, J=7.0 Hz, 6H), 1.49 (s, 9H).

2): 9-isopropyl-N-(4-(piperazin-1-yl)phenyl)isoxazolo[5,4-H]quinazolin-2-amine (I-27)

I-27a (20.0 mg, 0.041 mmol) was dissolved in dichloromethane (2 mL), and a solution of hydrogen chloride in 1,4-dioxane (4 N, 0.15 mL) was added. The mixture was stirred at room temperature for 2 hours, and then filtered by suction. The obtained residue was dried in vacuum by oil pump to constant weight to give the title compound I-27 (hydrochloride, 22.0 mg) as a yellow powder. LC-MS (ESI), $C_{22}H_{25}N_6O$ [M+H]$^+$: m/z=389.1.

TABLE 5

| Examples I-28 to I-37 | | | | |
|---|---|---|---|---|
| No. | Chemical structure | Chemical Name | Hydrogen spectrum ($^1$H NMR) | LC-MS (ESI) [M + H]$^+$ |
| I-28 | 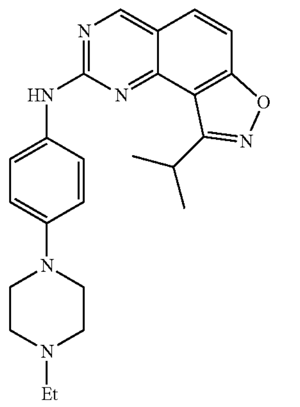 [SMILES: CCN1CCN(c2ccc(Nc3ncc4ccc5onc(C(C)C)c5c4n3)cc2)CC1] | N-(4-(4-ethylpiperazin-1-yl)phenyl)-9-isopropylisoxazolo[5,4-h] quinazolin-2-amine | $^1$H NMR (400 MHz, Chloroform-d, ppm) δ 9.03 (s, 1H), 7.75 (d, J = 8.8 Hz, 1H), 7.69-7.62 (m, 2H), 7.44 (d, J = 8.8 Hz, 1H), 7.37 (s, 1H), 6.99 (d, J = 8.9 Hz, 2H), 4.02 (p, J = 6.9 Hz, 1H), 3.28-3.21 (m, 4H), 2.66 (t, J = 5.0 Hz, 4H), 2.51 (q, J = 7.2 Hz, 2H), 1.56 (d, J = 6.9 Hz, 6H), 1.15 (t, J = 7.2 Hz, 3H) | 417.1 |
| I-29 | 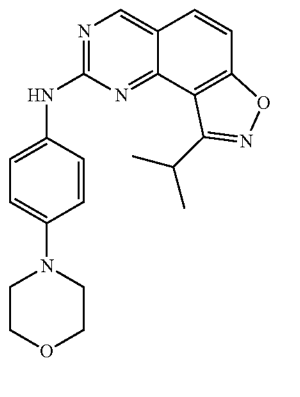 [SMILES: CC(C)c1noc2ccc3cnc(Nc4ccc(N5CCOCC5)cc4)nc3c12] | 9-isopropyl-N-(4-morpholinophenyl) isoxazolo[5,4-H]quinazolin-2-amine | $^1$H NMR (400 MHz, Chloroform-d, ppm) δ 9.04 (s, 1H), 7.77 (d, J = 8.8 Hz, 1H), 7.68 (d, J= 8.9 Hz, 2H), 7.46 (d, J = 8.8 Hz, 1H), 7.31 (s, 1H), 6.97 (d, J = 9.0 Hz, 2H), 4.11-3.98 (m, 1H), 3.95-3.87 (m, 4H), 3.24-3.12 (m, 4H), 1.57 (d, J = 7.2 Hz, 6H) | 390.2 |

TABLE 5-continued

| Examples I-28 to I-37 | | | | |
|---|---|---|---|---|
| No. | Chemical structure | Chemical Name | Hydrogen spectrum ($^1H$ NMR) | LC-MS (ESI) $[M + H]^+$ |
| I-30 | 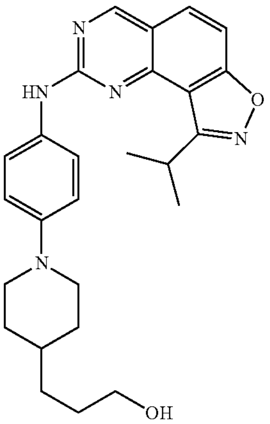 [SMILES: CC(C)c1noc2ccc3cnc(Nc4ccc(N5CCC(CCCO)CC5)cc4)nc3c12] | 3-(1-(4-((9-isopropylisoxazolo[5,4-h]quinazolin-2-yl)amino)phenyl) piperidin-4-yl)propan-1-ol | $^1H$ NMR (400 MHz, Chloroform-d, ppm) δ 9.03 (s, 1H), 7.75 (d, J = 8.8 Hz, 1H), 7.68-7.60 (m, 2H), 7.44 (d, J = 8.8 Hz, 1H), 7.33 (s, 1H), 6.99 (d, J = 9.0 Hz, 2H), 4.03 (p, J = 6.9 Hz, 1H), 3.73-3.62 (m, 4H), 2.76-2.66 (m, 2H), 1.85 (d, J = 9.3 Hz, 2H), 1.67 (s, 6H), 1.39 (m, 4H), 1.28 (m, 1H) | 446.2 |
| I-31 | 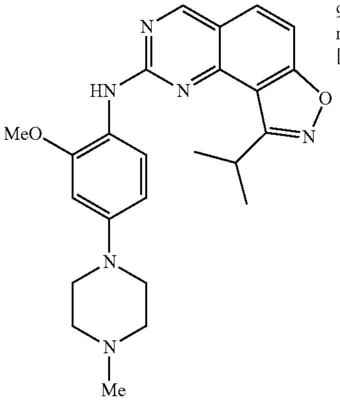 | 9-isopropyl-N-(2-methoxy-4-(4-methylpiperazin-l-yl)phenyl)isoxazolo [5,4-H]quinazolin-2- amine | $^1H$ NMR (400 MHz, Chloroform-d, ppm) δ 9.04 (s, 1H), 8.56 (d, J = 8.7 Hz, 1H), 7.86 (s, 1H), 7.76 (d, J = 8.8 Hz, 1H), 7.45 (d, J = 8.8 Hz, 1H), 6.60 (s, 1H), 4.10 (p, J = 6.9 Hz, 1H), 3.93 (s, 3H), 3.29 (t, J = 5.0 Hz, 4H), 2.74 (s, 4H), 2.46 (s, 3H), 1.61 (d, J = 6.9 Hz, 6H) | 433.1 |
| I-32 | 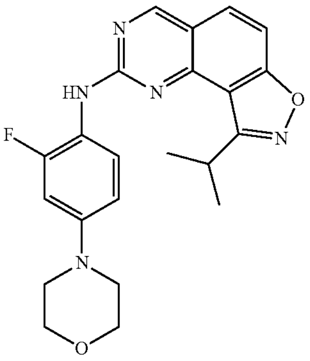 [SMILES: CC(C)c1noc2ccc3cnc(Nc4ccc(N5CCOCC5)cc4F)nc3c12] | N-(2-fluoro-4-morpholinophenyl)-9-isopropylisoxazolo[5,4-h] quinazolin-2-amine | $^1H$ NMR (400 MHz, Chloroform-d, ppm) δ 9.10 (s, 1H), 8.72-8.64 (m, 1H), 8.33 (s, 1H), 7.80 (d, J = 8.8 Hz, 1H), 7.50 (d, J = 8.8 Hz, 1H), 6.95 (d, J = 9.4 Hz, 1H), 4.07 (p, J = 7.0 Hz, 1H), 3.99-3.92 (m, 4H), 3.04-2.91 (m, 4H), 1.61 (d, J = 7.0 Hz, 6H) | 408.2, 409.1 |

TABLE 5-continued

Examples I-28 to I-37

| No. | Chemical structure | Chemical Name | Hydrogen spectrum ($^1H$ NMR) | LC-MS (ESI) $[M + H]^+$ |
|---|---|---|---|---|
| I-33 | 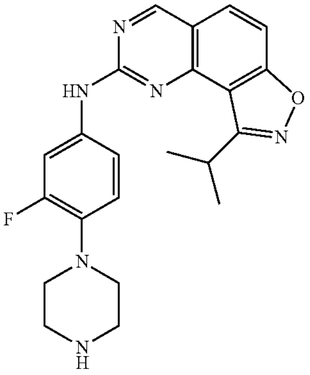 [SMILES: CC(C)c1noc2ccc3cnc(Nc4ccc(N5CCNCC5)c(F)c4)nc3c12] | N-(3-fluoro-4-(piperazin-1-yl) phenyl)-9-isopropylisoxazolo[5,4-H] quinazolin-2-amine | $^1H$ NMR (hydrochloride, 400 MHz, methanol-d, ppm) δ 9.11 (s, 1H), 8.16 (dd, J = 14.4, 2.8 Hz, 1H), 7.91 (d, J = 8.9 Hz, 1H), 7.62 (d, J = 8.9 Hz, 1H), 7.16 (dd, J = 8.9, 2.8 Hz, 1H), 7.03 (t, J = 9.0 Hz, 1H), 4.14 (p, J = 6.8 Hz, 1H), 4.15-3.99 (m, 4H), 3.22-3.17 (m, 4H), 1.59 (d, J = 6.8 Hz, 6H) | 407.2 |
| I-34 | 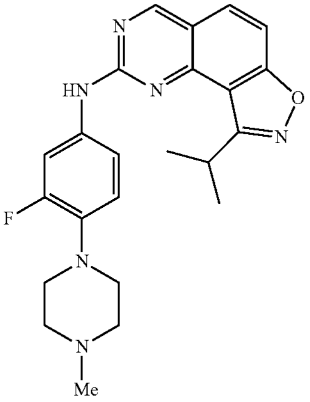 [SMILES: CC(C)c1noc2ccc3cnc(Nc4ccc(N5CCN(C)CC5)c(F)c4)nc3c12] | N-3-fluoro-4-4-methylpiperazin-1-yl)phenyl)-9-isopropylisoxazolo] 5,4-H]quinazolin-2-amine | $^1H$ NMR (400 MHz, dimethyl sulfoxide-d, ppm) δ 10.24 (s, 1H), 9.35 (s, 1H), 8.12 (d, J = 5.8 Hz, 1H), 8.09 (s, 1H), 7.68 (d, J = 8.8 Hz, 1H), 7.46 (dd, J = 8.8, 2.4 Hz, 1H), 4.02 (hept, J = 7.0 Hz, 1H), 3.21 (s, 4H), 3.07 (s, 4H), 2.50 (d, J = 2.1 Hz, 6H) | 421.1 |
| I-35 | 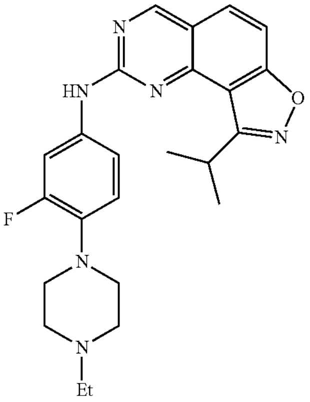 [SMILES: CCN1CCN(c2ccc(Nc3ncc4ccc5onc(C(C)C)c5c4n3)cc2F)CC1] | N-(4-(4-ethylpiperazin-1-yl)-3-fluorophenyl)-9-isopropylisoxazolo[5, 4-H]quinazolin-2-amine | $^1H$ NMR (400 MHz, Chloroform-d, ppm) δ 9.07 (s, 1H), 8.14-8.03 (m, 1H), 7.79 (d, J=8.8 Hz, 1H), 7.50 (d, J = 8.8 Hz, 1H), 7.37 (s, 1H), 7.14-7.06 (m, 1H), 6.98 (t, J = 9.0 Hz, 1H), 4.09 (p, J = 6.9 Hz, 1H), 3.16 (s, 4H), 2.68 (s, 3H), 2.52 (q, J = 7.2 Hz, 2H), 1.60 (d, J = 6.9 Hz, 6H), 1.15 (t, J = 7.2 Hz, 3H) | 435.1 |

TABLE 5-continued

| Examples I-28 to I-37 | | | | |
|---|---|---|---|---|
| No. | Chemical structure | Chemical Name | Hydrogen spectrum ($^1H$ NMR) | LC-MS (ESI) $[M + H]^+$ |
| I-36 | 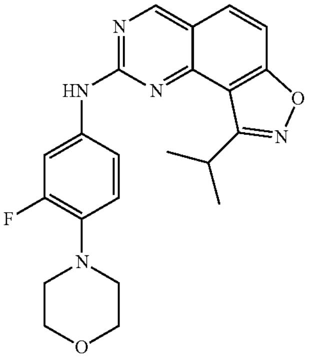 [SMILES: CC(C)c1noc2ccc3cnc(Nc4ccc(N5CCOCC5)c(F)c4)nc3c12] | N-(3-fluoro-4-morpholinophenyl)-9-isopropylisoxazolo[5,4-H]quinazolin-2-amine | $^1H$ NMR (400 MHz, Chloroform-d, ppm) δ 9.07 (s, 1H), 8.10 (dd, J = 14.6, 2.5 Hz, 1H), 7.80 (d, J = 8.8 Hz, 1H), 7.50 (d, J = 8.8 Hz, 1H), 7.45 (s, 1H), 7.11 (dd, J = 8.8, 2.5 Hz, 1H), 6.96 (t, J = 9.0 Hz, 1H), 4.09 (p, J = 6.9 Hz, 1H), 3.95-3.88 (m, 4H), 3.17-3.07 (m, 4H), 1.61 (d, J = 6.9 Hz, 6H) | 408.1 |
| I-37 | 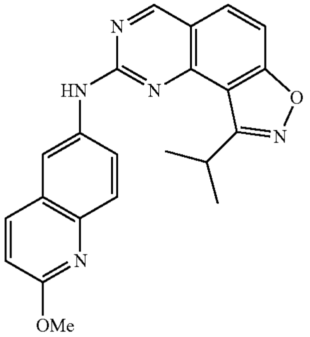 [SMILES: COc1ccc2cc(Nc3ncc4ccc5onc(C(C)C)c5c4n3)ccc2n1] | 9-isopropyl-N-(2-methoxyquinolin-6-yl)isoxazolo[5,4-H]quinazolin-2-amine | $^1H$ NMR (400 MHz, Chloroform-d, ppm) δ 9.18 (s, 1H), 8.13 (d, J = 1.6 Hz, 1H), 7.95 (d, J = 8.8 Hz, 1H), 7.91-7.85 (m, 3H), 7.62-7.55 (m, 2H), 6.96 (d, J = 8.9 Hz, 1H), 6.25 (p, J = 6.7 Hz, 1H), 4.10 (s, 3H), 1.83 (d, J = 6.7 Hz, 6H) | 386.1 |

By referring to the synthetic method of I-27 in Example I-27, compound I-33 (hydrochloride, 11.2 mg, 25.4 μmmol, 21%) was prepared from 7a (30 mg, 0.121 mmol).

By referring to the synthetic method of I-27a in Example I-27, compounds I-28 (18.0 mg, 39.9 μmmol, 33%), I-29 (15.4 mg, 36.3 μmmol, 30%), I-30 (15.7 mg, 32.7 (mmol, 271), 2-31 (6.2 mg, 13.3 μmmol, 11%), I-32 (7.5 mg, 16.9 μmmol, 14%), I-34 (22.6 mg, 49.6 μmmol, 41%), I-35 (23.3 mg, 49.6 μmmol, 36%), I-36 (15.6 mg, 35.1 μmmol, 29%), and I-37 (43.8 mg, 113.8 μmmol, 56.3%) were prepared from 7a (30 mg, 0.121 mmol).

TABLE 6

| Examples I-38 to I-39 | | | | |
|---|---|---|---|---|
| No. | Chemical structure | Chemical Name | Hydrogen spectrum ($^1H$ NMR) | LC-MS (ESI) $[M + H]^+$ |
| I-38 | 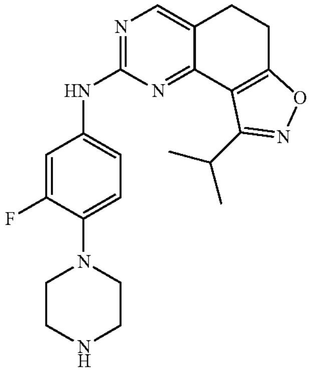 [SMILES: CC(C)c1noc2c1-c1nc(Nc3ccc(N4CCNCC4)c(F)c3)ncc1CC2] | N-(3-fluoro-4-(piperazin-1-yl)phenyl)-9-isopropyl-5,6-dihydroisoxazolo[5,4-H]quinazolin-2-amine | $^1H$ NMR (hydrochloride, 400 MHz, methanol-d, ppm) δ 8.23 (s, 1H), 8.02 (dd, J = 14.0, 2.8 Hz, 1H), 7.09 (dd, J = 8.9, 2.8 Hz, 1H), 7.01 (t, J = 9.0 Hz, 1H), 4.26 (p, J = 6.8 Hz, 1H), 4.19-4.05 (m, 4H), 3.31-3.22 (m, 4H), 3.09-3.02 (m, 4H), 1.61 (d, J = 6.8 Hz, 6H) | 409.2 |

TABLE 6-continued

Examples I-38 to I-39

| No. | Chemical structure | Chemical Name | Hydrogen spectrum ($^1H$ NMR) | LC-MS (ESI) $[M + H]^+$ |
|---|---|---|---|---|
| I-39 | 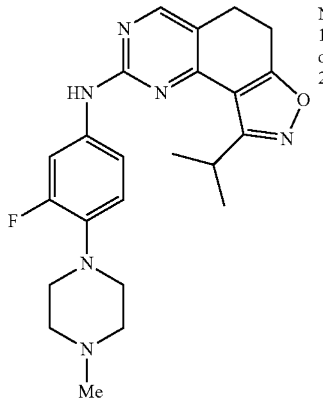 | N-(3-fluoro-4-(4-methylpiperazin-1-yl)phenyl)-9-isopropyl-5,6-dihydroisoxazolo[5,4-H]quinazolin-2-amine | $^1$NMR (400 MHz, Chloroform-d, ppm) δ 9.07 (s, 1H), 8.14-8.03 (m, 1H), 7.37 (s, 1H), 7.14-7.06 (m, 1H), 6.98 (t, J = 8.9 Hz, 1H), 4.09 (p, J = 6.9 Hz, 1H), 3.18-3.11 (m, 4H), 3.08-3.02 (m, 4H), 2.82-2.72 (m, 4H), 2.62 (s, 3H), 1.58 (d, J = 6.9 Hz, 6H) | 423.1 |

By referring to the synthetic method of I-24 in Example I-24, compound I-38 (hydrochloride, 12.3 mg, 27.8 μmmol, 23%) was prepared from 7d (30 mg, 0.120 mmol).

By referring to the synthetic method of I-24a in Example I-24, compound I-39 (18.0 mg, 37.5 μmmol, 31%) was prepared from 7d (30 mg, 0.120 mmol).

Example I-40

Preparation of 3-((9-isopropylisoxazolo[5,4-h]quinazolin-2-yl)amino)benzenesulfonamide (I-40)

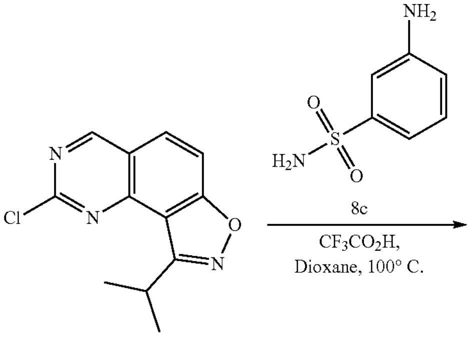

7a

-continued

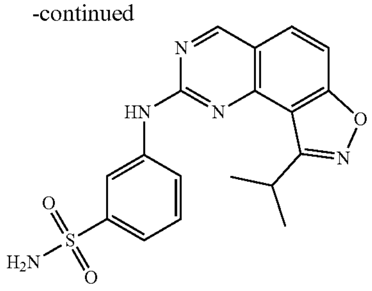

I-40

To a solution of 7a (30 mg, 0.121 mmol) and 8c (41.6 mg, 0.242 mmol) in 1,4-dioxane (1.5 mL), the atmosphere was replaced with argon for 2 times, and trifluoroacetic acid (13.5 μL, 0.182 mmol) was added. The temperature was raised to 100° C. and the tube was sealed to react for 8 hours. After cooling to room temperature, the reaction solution was diluted with ethyl acetate (5 mL) and aqueous half-saturated sodium bicarbonate solution (8 mL). The organic layer was separated, and the aqueous layer was extracted with ethyl acetate (5 mL) for 3 times. The organic layers were combined, washed with saturated brine (5 mL), dried over anhydrous sodium sulfate, filtered by suction, and concentrated. The obtained residue was purified by flash silica gel column chromatography (dichloromethane/methanol=80:1 to 10:1) to give the title compound 3-((9-isopropylisoxazolo[5,4-h]quinazolin-2-yl)amino)benzenesulfonamide I-40 (29.6 mg, 77.4 μmol, 32%) as a pale yellow solid. $^1$H NMR (400 MHz, dimethyl sulfoxide-d, ppm) δ 10.42 (s, 1H), 9.40 (s, 1H), 8.34 (s, 1H), 8.16 (d, J=8.4 Hz, 1H), 8.13 (d, J=8.9 Hz, 1H), 7.72 (d, J=8.8 Hz, 1H), 7.59 (t, J=7.9 Hz, 1H), 7.53 (dt, J=7.8, 1.4 Hz, 1H), 4.07 (p, J=6.9 Hz, 1H), 1.47 (d, J=6.8 Hz, 6H).

TABLE 7

| Examples I-41 to I-44 | | | | |
|---|---|---|---|---|
| No. | Chemical structure | Chemical Name | Hydrogen spectrum ($^1$H NMR) | LC-MS (ESI) $[M + H]^+$ |
| I-41 | 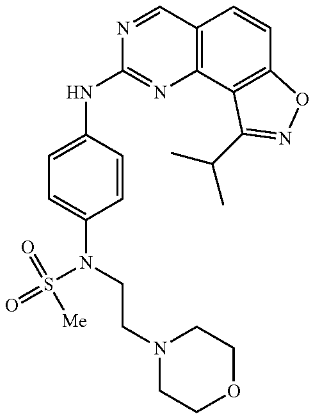 [SMILES: CC(C)c1noc2ccc3cnc(Nc4ccc(N(CCN5CCOCC5)S(C)(=O)=O)cc4)nc3c12] | N-(4-((9-isopropylisoxazolo[5,4-H]quinazolin-2-yl)amino)phenyl)-N-(2-morpholinoethyl) methanesulfonamide | $^1$NMR (400 MHz, Chloroform-d, ppm) δ 9.18 (s, 1H), 7.89 (d, J =8.9 Hz, 1H), 7.65 (d, J = 8.8 Hz, 1H), 7.18 (d, J = 8.9 Hz, 2H), 6.86 (d, J = 8.8 Hz, 2H), 4.12 (p, J = 6.8 Hz, 1H), 3.73 (brs, 4H), 3.42 (t, 2H), , 3.21 (m, 4H), 2.83 (s, 3H), 2.15 (t, 2H), 1.61 (d, J = 6.8 Hz, 6H) | 511.3 |
| I-42 | 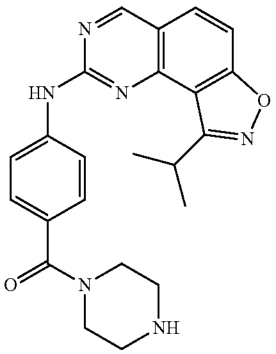 [SMILES: CC(C)c1noc2ccc3cnc(Nc4ccc(C(=O)N5CCNCC5)cc4)nc3c12] | (4-((9-isopropylisoxazolo[5,4-H] quinazolin-2-yl)amino)phenyl) (piperazin-1-yl)methanone | $^1$H NMR (400 MHz, Chloroform-d, ppm) δ 9.09 (s, 1H), 7.81 (d, J = 8.7 Hz, 1H), 7.72 (d, J = 8.6 Hz, 2H), 7.63 (s, 1H), 7.51 (d, J = 8.8 Hz, 1H), 7.32 (d, J = 8.7 Hz, 2H), 4.06 (p, J = 6.9 Hz, 1H), 3.61 (s, 4H), 3.42 (s, 4H), 1.60 (d, J = 6.8 Hz, 6H) | 417.1 |
| I-43 | 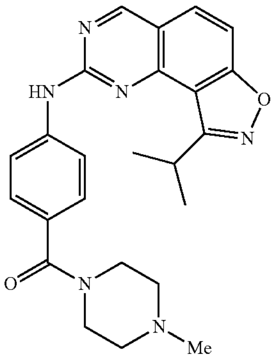 [SMILES: CC(C)c1noc2ccc3cnc(Nc4ccc(C(=O)N5CCN(C)CC5)cc4)nc3c12] | (4-((9-isopropylisoxazolo[5,4-H] quinazolin-2-yl)amino)phenyl) (4-methylpiperazin-1-yl)methanone | $^1$H NMR (400 MHz, Chloroform-d, ppm) δ 9.00 (s, 1H), 7.88 (d, J = 8.8 Hz, 1H), 7.74-7.63 (m, 2H), 7.51 (s, 1H), 7.58 (d, J = 8.9 Hz, 1H), 7.49-7.29 (m, 2H), 4.01 (p, J = 6.7 Hz, 1H), 3.66 (brs, 4H), 2.59 (brs, 4H), 1.85 (d, J = 6.7 Hz, 6H) | 431.2 |
| I-44 | 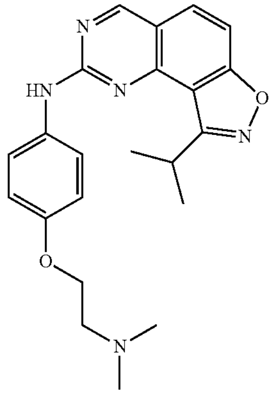 [SMILES: CC(C)c1noc2ccc3cnc(Nc4ccc(OCCN(C)C)cc4)nc3c12] | N-(4-(2-(dimethylamino)ethoxy) phenyl)-9-isopropylisoxazolo[5, 4-h]quinazolin-2-amine | $^1$H NMR (400 MHz, Chloroform-d, ppm) δ 9.03 (s, 1H), 7.80 (d, J = 8.9 Hz, 1H), 7.56 (d, J = 9.0 Hz, 2H), 7.49 (d, J = 8.9 Hz, 1H), 7.29 (s, 1H), 6.87 (d, J =9.0 Hz, 2H), 4.13 (p, J = 6.5 Hz, 1H), 3.91 (t, J = 5.6 Hz, 2H), 2.69 (t, J = 5.3 Hz, 2H), 1.59 (d, J = 6.8 Hz, 6H) | 392.1 |

By referring to the synthetic method of I-40 in Example I-40, compounds I-41 (39.6 mg, 77.8 μmmol, 48%), I-42 (19.5 mg, 47.0 μmmol, 29%), I-43 (21.6 mg, 50.2 μmmol, 31%), and I-44 (27.9 mg, 71.3 μmmol, 44%) were prepared from 7a (40 mg, 0.162 mmol).

Biological Example

Kinase Activity Assay

The inhibitory effect of compounds against the kinase CDK4/cyclin D3 was detected by Caliper Mobility Shift Assay method. The final concentration of the compounds to be tested was set at 10 concentrations starting from 1 μM by 3-fold serial dilution. 5 μL of compounds at 5-fold final concentration and 10 μL of CDK4/cyclin D3 kinase solution at a final concentration of 10 nM was added to a 384-well reaction plate, respectively. The plate was pre-incubated for 10 min at room temperature (with negative control wells containing 10 μL of kinase buffer and 5 μL of 5% DMSO; positive control wells containing 10 μL of kinase solution and 5 μL of 5% DMSO). The reaction was initiated by adding 10 μL of ATP at a final concentration of 250 μM and the corresponding substrate peptide mixture at room temperature for 150 minutes. 30 μL of stop detection solution containing EDTA was added to stop the kinase reaction. Caliper EZ Reader was used to read the conversion rate. Inhibition rate %=(average conversion rate of positive control %−conversion rate of sample %)/(average conversion rate of positive control %−average conversion rate of negative control %). wherein: negative control wells represent the conversion rate readings of wells without enzymatic activity; positive control wells represent conversion readings for wells with no compound inhibition. The log(inhibitor) vs. response—Variable slope of the analysis software GraphPad Prism 5 was used with log concentration value as the X-axis and the percent inhibition rate as the Y-axis to fit the dose-response curve, the IC50 value of each compound on the enzyme activity was thus obtained. Calculation formula: Y=Bottom+(Top−Bottom)/(1+10^((Log IC50−X)*HillSlope)).

The IC50 values for CDK6/Cyclin D3 and CDK2/Cyclin A2 of compounds of the present disclosure were tested in a similar manner.

The results of the enzyme inhibitory activities of the representative compounds of the present disclosure are shown in the table below.

| Compound No. | CDK4/D3 $IC_{50}$ (nM) | CDK6/D3 $IC_{50}$ (nM) | CDK2/A2 $IC_{50}$ (nM) |
|---|---|---|---|
| I-1 | 2 | 7 | |
| I-2 | 6 | 23 | |
| I-3 | 8 | 36 | |
| I-4 | 1 | 4 | |
| I-5 | 1 | 4 | |
| I-6 | 82 | 377 | |
| I-7 | 36 | 176 | |
| I-8 | 5 | 15 | |
| I-9 | 4 | 14 | |
| I-10 | 21 | 67 | |
| I-11 | 8 | 24 | |
| I-12 | 9 | 40 | |
| I-13 | 4 | 12 | |
| I-14 | 4 | 10 | |
| I-15 | 7 | 19 | |
| I-16 | 7 | 25 | |
| I-17 | 5 | 21 | |
| I-18 | 6 | 32 | |
| I-19 | 7 | 37 | |

-continued

| Compound No. | CDK4/D3 $IC_{50}$ (nM) | CDK6/D3 $IC_{50}$ (nM) | CDK2/A2 $IC_{50}$ (nM) |
|---|---|---|---|
| I-20 | 7 | 39 | |
| I-21 | 47 | 245 | |
| I-22 | 7 | 21 | |
| I-23 | 5 | 15 | |
| I-24 | 13 | 82 | |
| I-25 | 11 | 64 | |
| I-26 | 63 | 276 | |
| I-27 | 3 | 8 | 6 |
| I-28 | 2 | 5 | 4 |
| I-29 | 14 | 36 | 10 |
| I-30 | 100 | 245 | 140 |
| I-31 | 98 | 340 | 244 |
| I-32 | 150 | 359 | 294 |
| I-33 | 3 | 7 | 10 |
| I-34 | 3 | 9 | 12 |
| I-35 | 3 | 8 | 10 |
| I-36 | 20 | 34 | 22 |
| I-37 | 34 | 68 | 82 |
| I-38 | 7 | 21 | 10 |
| I-39 | 6 | 17 | 11 |
| I-40 | 2 | 6 | 10 |
| I-41 | 2 | 7 | 12 |
| I-42 | 3 | 9 | 5 |
| I-43 | 1 | 5 | 4 |
| I-44 | 2 | 4 | 10 |

While the present disclosure has been described in detail with reference to the specific preferred embodiments, it cannot be concluded that the specific embodiments of the present disclosure are limited to these descriptions. Those skilled in the art will appreciate that several simple deductions or substitutions may be made without departing from the spirit of the present disclosure, which should be regarded to be within the scope of the present disclosure.

What is claimed is:

1. A compound of formula (I), or a pharmaceutically acceptable salt, an enantiomer, a diastereomer, and a racemate thereof:

(I)

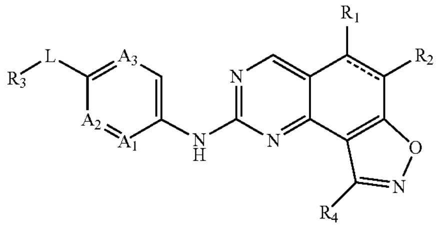

wherein:

⎓ indicates a single bond or a double bond;

$A_1$ is selected from $CR_5$ or N;

$A_2$ is selected from $CR_6$ or N;

$A_3$ is selected from $CR_7$ or N;

$R_1$ is selected from H, D, halogen, —CN, —$OR_a$, —$SR_a$, —$NR_bR_c$, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_6$-10 aryl, or 5- to 10-membered heteroaryl; wherein the said $C_{3-7}$ cycloalkyl or 3- to 7-membered heterocyclyl is optionally substituted by oxo or thioxo;

$R_2$ is selected from H, D, halogen, —CN, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl;

wherein the said $C_{3-7}$ cycloalkyl or 3- to 7-membered heterocyclyl is optionally substituted by oxo or thioxo;

$R_3$ is selected from H, D, halogen, —CN, —$NO_2$, —$OR_a$, —$SR_a$, —$NR_bR_c$, —C(O)$R_a$, —C(O)$OR_a$, —C(O)$NR_bR_c$, —$S(O)_mR_a$, —$S(O)_mOR_a$, —$S(O)_mNR_bR_c$, —O—$C_{1-6}$ alkylene-$R_8$, $C_{1-6}$ alkyl, $C_{1-6}$ haloalkyl, $C_{3-7}$ cycloalkyl, 3- to 11-membered heterocyclyl, $C_{6-10}$ aryl, or 5- to 10-membered heteroaryl, each of which is optionally substituted by 1, 2, 3, 4, or 5 $R_8$ groups;

$R_4$ is selected from H, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl;

L is selected from a chemical bond, —O—, —NH—, —C(O)—, —C(O)NH—, —NHC(O)—, —$C_{1-6}$ alkylene-, —$C_{2-6}$ alkenylene- or —$C_{2-6}$ alkynylene-;

and wherein, $R_5$ is selected from H, D, halogen, —CN, —$OR_a$, —$SR_a$, —$NR_bR_c$, —C(O)$R_a$, —C(O)$OR_a$, C(O)$NR_bR_c$, —$S(O)_mR_a$, —$S(O)_mOR_a$, —$S(O)_mNR_bR_c$, $C_{1-6}$ alkyl or $C_{1-6}$ haloalkyl;

$R_6$ is selected from H, D, halogen, —CN, —$OR_a$, —$SR_a$, —$NR_bR_c$, —C(O)$R_a$, —C(O)$OR_a$, —C(O)$NR_bR_c$, —$S(O)_mR_a$, —$S(O)_mOR_a$, —$S(O)_mNR_bR_c$, $C_{1-6}$ alkyl or $C_{1-6}$ haloalkyl;

$R_7$ is selected from H, D, halogen, —CN, —$OR_a$, —$SR_a$, —$NR_bR_c$, —C(O)$R_a$, —C(O)$OR_a$, —C(O)$NR_bR_c$, —$S(O)_mR_a$, —$S(O)_mOR_a$, —$S(O)_mNR_bR_c$, $C_{1-6}$ alkyl or $C_{1-6}$ haloalkyl;

$R_8$ is selected from H, D, —$NH_2$, —$NHC_{1-6}$ alkyl, —N($C_{1-6}$ alkyl)$_2$, $C_{1-6}$ alkyl, $C_{1-6}$ haloalkyl, —$C_{0-6}$ alkylene-$OR_a$, $C_{3-7}$ cycloalkyl, 3- to 7-membered heterocyclyl, $C_{6-10}$ aryl, or 5- to 10-membered heteroaryl; or two $R_8$ on the same atom are taken together to form oxo or thioxo;

$R_a$ is independently selected from H, —$C_{0-6}$ alkylene-CN, —$C_{0-6}$ alkylene-$NO_2$, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C(O)OR', —$C_{0-6}$ alkylene-C(O)NR"R'", —$C_{0-6}$ alkylene-$S(O)_m$R', —$C_{0-6}$ alkylene-$S(O)_m$OR', —$C_{0-6}$ alkylene-$S(O)_m$NR"R'", $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl;

$R_b$ and $R_c$ are independently selected from H, —$C_{0-6}$ alkylene-CN, —$C_{0-6}$ alkylene-$NO_2$, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C(O)OR', —$C_{0-6}$ alkylene-C(O)NR"R'", —$C_{0-6}$ alkylene-$S(O)_m$R', —$C_{0-6}$ alkylene-$S(O)_m$OR', —$C_{0-6}$ alkylene-$S(O)_m$NR"R'", $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or, $R_b$, $R_c$ and N atom are taken together to form 3- to 7-membered heterocyclyl;

R' is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl;

R" and R'" are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl; or, R", R'" and N atom are taken together to form 3- to 7-membered heterocyclyl;

m represents 0, 1, or 2;

and, $R_1$-$R_2$ and $R_4$-$R_8$ are optionally substituted with 1, 2 or 3 R groups, wherein the R is independently selected from H, —OH, halogen, —$NO_2$, carbonyl, —CN, —$OR_a$, —$SR_a$, —$NR_bR_c$, —C(O)$R_a$, —C(S)$R_a$, —C(O)$OR_a$, —C(S)$OR_a$, —C(O)—$NR_bR_c$, —C(S)—$NR_bR_c$, —O—C(O)$R_a$, —O—C(S)$R_a$, —N($R_b$)—C(O)—$R_a$, —N($R_b$)—C(S)—$R_a$, —$S(O)_mR_a$, —$S(O)_mOR_a$, —$S(O)_mNR_bR_c$, —N($R_b$)—$S(O)_m$—$R_a$, —N($R_b$)$S(O)_m$—$NR_bR_c$, —N(R)C(O)$OR_a$, —N($R_b$)—C(S)$OR_a$, —O—$C_{1-6}$ alkylene-$OR_a$, —C(O)—$C_{1-6}$ alkylene-$NR_bR_c$, —N($R_b$)—C(O)—$NR_bR_c$, —N($R_b$)C(S)—$NR_bR_c$, —O—C(O)—$NR_bR_c$, —O—C(S)—$NR_bR_c$, $C_{1-6}$ alkyl, $C_{1-6}$ haloalkyl, $C_{2-6}$ alkenyl, $C_{2-6}$ alkynyl, $C_{3-7}$ cycloalkyl, 3- to 7-membered heterocyclyl, $C_{6-10}$ aryl, or 5- to 10-membered heteroaryl; wherein the said $C_{1-6}$ alkyl, $C_{1-6}$ haloalkyl, $C_{2-6}$ alkenyl, $C_{2-6}$ alkynyl, $C_{3-7}$ cycloalkyl, 3- to 7-membered heterocyclyl, $C_{6-10}$ aryl or 5- to 10-membered heteroaryl is each further optionally substituted by one or more groups consisting of the following:

—CN, —$NO_2$, carbonyl, —$OR_a$, —$SR_a$, —$NR_bR_c$, —C(O)$R_a$, —C(S)$R_a$, —C(O)$OR_a$, —C(S)$OR_a$, —C(O)—$NR_bR_c$, —C(S)—$NR_bR_c$, —O—C(O)$R_a$, —O—C(S)$R_a$, —N($R_b$)—C(O)—$R_a$, —N($R_b$)—C(S)—$R_a$, —$S(O)_mR_a$, —$S(O)_mOR_a$, —$S(O)_mNR_bR_c$, —N($R_b$)—$S(O)_m$—$R_a$, —N(R)$S(O)_m$—$R_bR_c$, —N($R_b$)—C(O)$OR_a$, —N($R_b$)—C(S)$OR_a$, —O—$C_{1-6}$ alkylene-$OR_a$, —C(O)—$C_{1-6}$ alkylene-$NR_bR_c$, —N($R_b$)—C(O)—$NR_bR_c$, —N(R)—C(S)—$NR_bR_c$, —O—C(O)—$NR_bR_c$ or —O—C(S)—$NR_bR_c$;

$R_a$, $R_b$ and $R_c$ are each further optionally substituted by one or more groups consisting of the following:

$C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl or 5- to 10-membered heteroaryl.

2. The compound according to claim 1, or a pharmaceutically acceptable salt, an enantiomer, a diastereomer, and a racemate thereof, which is a compound of general formula (I-1):

(I-1)

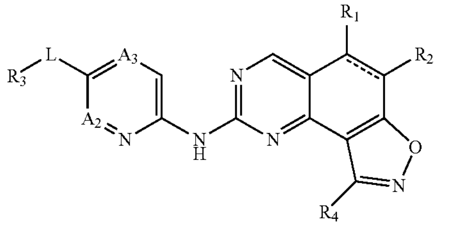

wherein, each group is as defined in claim 1;

alternatively, which is a compound of general formula (I-1-1):

(I-1-1)

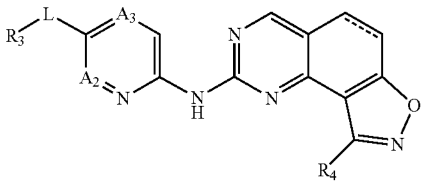

wherein,

⎓ indicates a single bond or a double bond;

$A_2$ is selected from $CR_6$ or N;

$A_3$ is selected from $CR_7$;

L is selected from a chemical bond, —O—, —NH—, —C(O)— or —$C_{1-6}$ alkylene-;

$R_3$ is selected from H, halogen, —CN, $C_{1-6}$ alkyl, $C_{1-6}$ haloalkyl, $C_{3-7}$ cycloalkyl or 3- to 11-membered heterocyclyl, the said group is optionally substituted with 1, 2 or 3 $R_8$ groups; alternatively, $R_3$ is 5- to 6-membered heterocyclyl containing at least one N atom, which is optionally substituted with 1 or 2 $R_8$ groups; alternatively, $R_3$ is piperazinyl, morpholinyl, thiomorpholinyl or piperidinyl, which is optionally substituted with 1 or 2 $R_8$ groups;

$R_4$ is selected from H, $C_{1-6}$ alkyl, $C_{1-6}$ haloalkyl, $C_{3-7}$ cycloalkyl or 3- to 7-membered heterocyclyl;

$R_6$ is selected from H, halogen, —CN, $C_{1-6}$ alkyl or $C_{1-6}$ haloalkyl;

$R_7$ is selected from H, halogen, —CN, $C_{1-6}$ alkyl or $C_{1-6}$ haloalkyl;

$R_8$ is selected from H, —$NH_2$, —$NHC_{1-6}$ alkyl, —$N(C_{1-6}$ alkyl$)_2$, $C_{1-6}$ alkyl, $C_{1-6}$ haloalkyl, —$C_{0-6}$ alkylene-$OR_a$, $C_{3-7}$ cycloalkyl or 3- to 7-membered heterocyclyl; or two $R_8$ on the same atom are taken together to form oxo or thioxo;

alternatively, which is a compound of general formula (I-1-1):

(I-1-1)

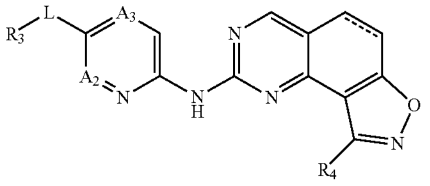

wherein,

⎓ indicates a single bond or a double bond;

$A_2$ is selected from $CR_6$ or N;

$A_3$ is $CR_7$;

L is selected from a chemical bond or $CH_2$;

$R_3$ is selected from 5- to 6-membered heterocyclyl, which is optionally substituted with 1 or 2 $R_8$ groups; alternatively, the 5- to 6-membered heterocyclyl is piperazinyl, morpholinyl, thiomorpholinyl or piperidinyl;

$R_4$ is selected from iPr, iBu or cyclopentyl;

$R_6$ is H or Me;

$R_7$ is H or Me;

$R_8$ is selected from H, Me, Et, iPr, iBu, $NEt_2$, oxo or cyclopropyl.

3. The compound according to claim 1, or a pharmaceutically acceptable salt, an enantiomer, a diastereomer, and a racemate thereof, which is a compound of general formula (I-2):

(I-2)

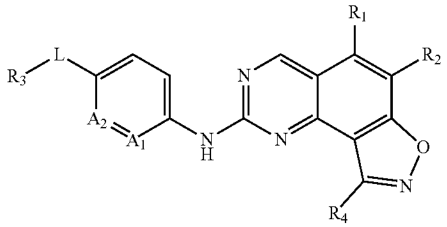

wherein, each group is as defined in claim 1;

alternatively, which is a compound of general formula (I-2-1):

(I-2-1)

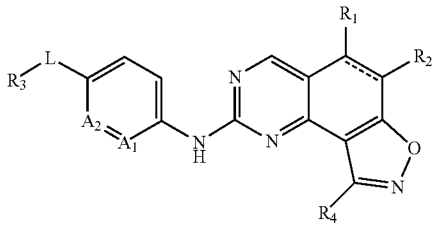

wherein, each group is as defined in claim 1;

alternatively, which is a compound of general formula (I-2-2):

(I-2-2)

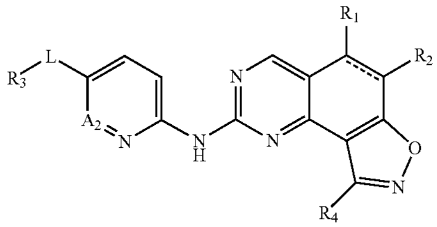

wherein,

⎓ indicates a single bond or a double bond;

$A_2$ is selected from $CR_6$ or N;

L is selected from a chemical bond, —O—, —NH—, —C(O)— or —$C_{1-6}$ alkylene-;

$R_3$ is selected from H, halogen, —CN, $C_{1-6}$ alkyl, $C_{1-6}$ haloalkyl, $C_{3-7}$ cycloalkyl or 3- to 11-membered heterocyclyl, the said group is optionally substituted with 1, 2 or 3 $R_8$ groups; alternatively, $R_3$ is 5- to 6-membered heterocyclyl containing at least one N atom, which is optionally substituted with 1 or 2 $R_8$ groups; alternatively, $R_3$ is piperazinyl, morpholinyl, thiomorpholinyl or piperidinyl, which is optionally substituted with 1 or 2 $R_8$ groups;

$R_4$ is selected from H, $C_{1-6}$ alkyl, $C_{1-6}$ haloalkyl, $C_{3-7}$ cycloalkyl or 3- to 7-membered heterocyclyl;

$R_6$ is selected from H, halogen, —CN, $C_{1-6}$ alkyl or $C_{1-6}$ haloalkyl;

$R_8$ is selected from H, —$NH_2$, —$NHC_{1-6}$ alkyl, —$N(C_{1-6}$ alkyl$)_2$, $C_{1-6}$ alkyl, $C_{1-6}$ haloalkyl, —$C_{0-6}$ alkylene-$OR_a$, $C_{3-7}$ cycloalkyl or 3- to 7-membered heterocyclyl; or two $R_8$ on the same atom are taken together to form oxo or thioxo;

alternatively, which is a compound of general formula (I-2-2):

(I-2-2)

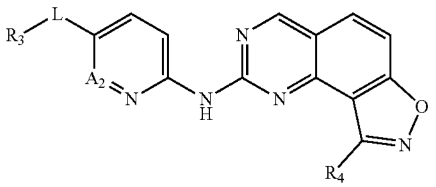

wherein,

⎓ indicates a single bond or a double bond;

$A_2$ is selected from $CR_6$ or N;

L is selected from a chemical bond or $CH_2$;

$R_3$ is selected from 5- to 6-membered heterocyclyl, which is optionally substituted with 1 or 2 $R_8$ groups; alternatively, the 5- to 6-membered heterocyclyl is piperazinyl, morpholinyl, thiomorpholinyl or piperidinyl;

$R_4$ is selected from iPr, iBu or cyclopentyl;

$R_6$ is H or Me;

$R_8$ is selected from H, Me, Et, iPr, iBu, $NEt_2$, oxo or cyclopropyl.

4. The compound according to claim 1, or a pharmaceutically acceptable salt, an enantiomer, a diastereomer, and a racemate thereof, which is a compound of general formula (I-3):

(I-3)

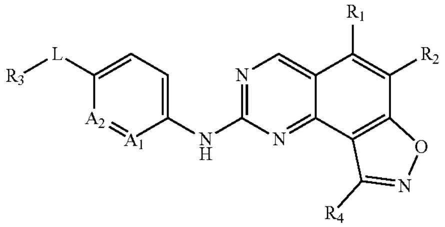

wherein, each group is as defined in claim 1;

alternatively, which is a compound of general formula (I-3-1):

(I-3-1)

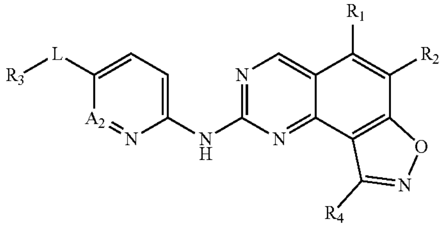

wherein, each group is as defined in claim 1;

alternatively, which is a compound of general formula (I-3-2):

(I-3-2)

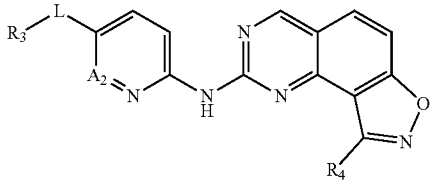

wherein, $A_2$ is selected from $CR_6$ or N;

L is selected from a chemical bond, —O—, —NH—, —C(O)— or —$C_{1-6}$ alkylene-;

$R_3$ is selected from H, halogen, —CN, $C_{1-6}$ alkyl, $C_{1-6}$ haloalkyl, $C_{3-7}$ cycloalkyl or 3- to 11-membered heterocyclyl, the said group is optionally substituted with 1, 2 or 3 $R_8$ groups; alternatively, $R_3$ is 5- to 6-membered heterocyclyl containing at least one N atom, which is optionally substituted with 1 or 2 $R_8$ groups; alternatively, $R_3$ is piperazinyl or piperidinyl, which is optionally substituted with 1 or 2 $R_8$ groups;

$R_4$ is selected from H, $C_{1-6}$ alkyl, $C_{1-6}$ haloalkyl, $C_{3-7}$ cycloalkyl or 3- to 7-membered heterocyclyl;

$R_6$ is selected from H, halogen or —CN;

$R_8$ is selected from H, —$NH_2$, —$NHC_{1-6}$ alkyl, —$N(C_{1-6}$ alkyl$)_2$, $C_{1-6}$ alkyl, $C_{1-6}$ haloalkyl or —$C_{0-6}$ alkylene-$OR_a$; or two $R_8$ on the same atom are taken together to form oxo or thioxo;

alternatively, which is a compound of general formula (I-3-2):

(I-3-2)

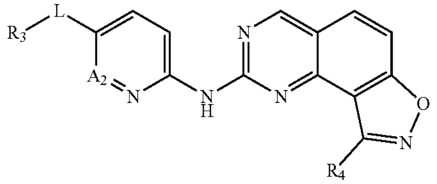

wherein, $A_2$ is selected from $CR_6$ or N;

L is selected from a chemical bond or $CH_2$;

$R_3$ is 5- to 6-membered heterocyclyl, the said group is optionally substituted with 1 or 2 $R_8$ groups; alternatively, the 5- to 6-membered heterocyclyl is piperazinyl or piperidinyl;

$R_4$ is selected from iPr, iBu or cyclopentyl;

$R_6$ is H;

$R_8$ is selected from H, Me, Et, iPr, iBu, $NEt_2$ or oxo.

5. The compound according to claim 1, or a pharmaceutically acceptable salt, an enantiomer, a diastereomer, and a racemate thereof, which is a compound of general formula (I-4):

(I-4)

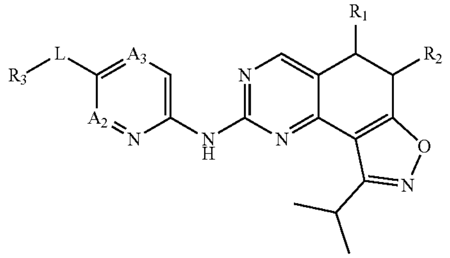

wherein, each group is as defined in claim 1;

alternatively, which is a compound of general formula (I-4-1):

(I-4-1)

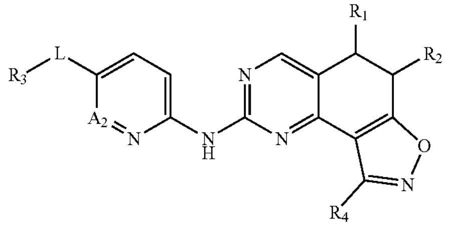

wherein, each group is as defined in claim 1;

alternatively, which is a compound of general formula (I-4-2):

(I-4-2)

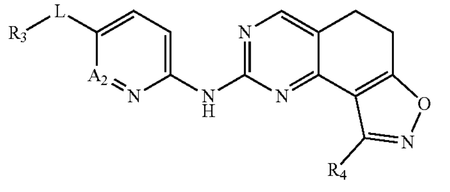

wherein, $A_2$ is selected from $CR_6$ or N;

L is selected from a chemical bond, —O—, —NH—, —C(O)— or —$C_{1-6}$ alkylene-;

$R_3$ is selected from H, halogen, —CN, $C_{1-6}$ alkyl, $C_{1-6}$ haloalkyl, $C_{3-7}$ cycloalkyl or 3- to 11-membered heterocyclyl, the said group is optionally substituted with 1, 2 or 3 $R_8$ groups; alternatively, $R_3$ is 5- to 6-membered heterocyclyl containing at least one N atom, which is optionally substituted with 1 or 2 $R_8$ groups; alternatively, $R_3$ is piperazinyl, morpholinyl, thiomorpholinyl or piperidinyl, which is optionally substituted with 1 or 2 $R_8$ groups;

$R_4$ is selected from H, $C_{1-6}$ alkyl, $C_{1-6}$ haloalkyl, $C_{3-7}$ cycloalkyl or 3- to 7-membered heterocyclyl;

$R_6$ is selected from H, halogen, —CN, $C_{1-6}$ alkyl or $C_{1-6}$ haloalkyl;

$R_8$ is selected from H, —$NH_2$, —$NHC_{1-6}$ alkyl, —N($C_{1-6}$ alkyl)$_2$, $C_{1-6}$ alkyl, $C_{1-6}$ haloalkyl, —$C_{0-6}$ alkylene-$OR_a$, $C_{3-7}$ cycloalkyl or 3- to 7-membered heterocyclyl; or two $R_8$ on the same atom are taken together to form oxo or thioxo;

alternatively, which is a compound of general formula (I-4-3):

(I-4-3)

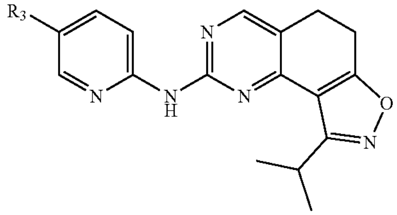

wherein, $R_3$ is 5- to 6-membered heterocyclyl, the said group is optionally substituted with 1 or 2 $R_8$ groups; alternatively, the 5- to 6-membered heterocyclyl is piperazinyl or morpholinyl;

$R_8$ is selected from H or Et.

6. The compound according to claim 1, or a pharmaceutically acceptable salt, an enantiomer, a diastereomer, a racemate thereof, and mixtures thereof, which is a compound of general formula (I-5) or (I-5-1):

(I-5)

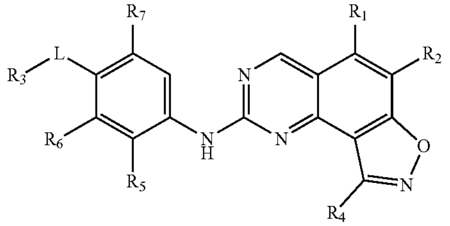

or (I-5-1)

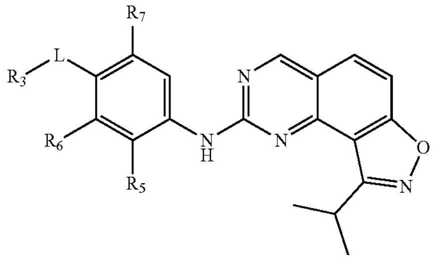

wherein, $\overline{\overline{\ \ }}$ indicates a single bond or a double bond;

$R_1$ is selected from H, D, halogen, —CN, —$OR_a$, $C_{1-6}$ alkyl or $C_{1-6}$ haloalkyl;

$R_2$ is selected from H, D, halogen, —CN, —$OR_a$, $C_{1-6}$ alkyl or $C_{1-6}$ haloalkyl;

$R_3$ is —$NR_bR_c$, —O—$C_{1-6}$ alkylene-$R_8$ or 4- to 7-membered heterocyclyl optionally substituted by 1, 2 or 3 $R_8$ groups;

L is selected from a chemical bond, —C(O)—, —C(O)NH— or —NHC(O)—;

$R_4$ is selected from $C_{1-6}$ alkyl, $C_{1-6}$ haloalkyl, $C_{3-7}$ cycloalkyl or 3- to 7-membered heterocyclyl;

$R_5$ is selected from H, D, halogen, $OR_a$, —$NR_bR_c$, —$S(O)_mR_a$, —$S(O)_mOR_a$ or —$S(O)_mNR_bR_c$;

$R_6$ is selected from H, D, halogen, —$S(O)_mR_a$, —$S(O)_mOR_a$ or —$S(O)_mNR_bR_c$;

$R_7$ is selected from H, D, halogen, —$S(O)_mR_a$, —$S(O)_mOR_a$ or —$S(O)_mNR_bR_c$;

$R_8$ is independently selected from H, D, —$NH_2$, —$NHC_{1-6}$ alkyl, —N($C_{1-6}$ alkyl)$_2$, $C_{1-6}$ alkyl or $C_{1-6}$ haloalkyl;

$R_8$ is optionally substituted with 1, 2 or 3 R groups, wherein the R is independently selected from H, —OH, halogen, —$NO_2$, carbonyl, —CN, —$OR_a$, —$SR_a$ or —$NR_bR_c$;

$R_a$ is independently selected from H, —$NH_2$, —$NHC_{1-6}$ alkyl, —$N(C_{1-6}$ alkyl$)_2$, $C_{1-6}$ alkyl or $C_{1-6}$ haloalkyl;

$R_b$ and $R_c$ are independently selected from H, —$C_{0-6}$ alkylene-$S(O)_mR'$, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl or —$C_{0-6}$ alkylene-3- to 7-membered heterocyclyl; or, $R_b$, $R_c$ and N atom are taken together to form 3- to 7-membered heterocyclyl;

R' is independently selected from H, $C_{1-6}$ alkyl, $C_{2-6}$ alkenyl, $C_{2-6}$ alkynyl or $C_{1-6}$ haloalkyl;

m represents 0, 1, or 2.

7. The compound of formula (I-5) or (I-5-1) according to claim 6, or a pharmaceutically acceptable salt, an enantiomer, a diastereomer, and a racemate, thereof, wherein, ⎓ indicates a single bond or a double bond;

$R_1$ is selected from H, D, halogen, —CN or —$OR_a$;

$R_2$ is selected from H, D, halogen, —CN or —$OR_a$;

$R_3$ is —$NR_bR_c$, —O—$C_{1-6}$ alkylene-$R_8$ or 5- to 6-membered heterocyclyl optionally substituted by 1 or 2 $R_8$ groups;

L is selected from a chemical bond, —C(O)—, —C(O)NH— or —NHC(O)—;

$R_4$ is selected from $C_{1-6}$ alkyl, $C_{1-6}$ haloalkyl, $C_{3-7}$ cycloalkyl or 3- to 7-membered heterocyclyl;

$R_5$ is selected from H, D, halogen or $OR_a$;

$R_6$ is selected from H, D or halogen;

$R_7$ is selected from H, D or halogen;

$R_8$ is independently selected from H, D, —$NH_2$, —$NHC_{1-6}$ alkyl, —$N(C_{1-6}$ alkyl$)_2$, $C_{1-6}$ alkyl or $C_{1-6}$ haloalkyl;

$R_8$ is optionally substituted with 1, 2 or 3 R groups, wherein the R is independently selected from H, —OH, halogen, —$NO_2$, carbonyl, —CN, —$OR_a$, —$SR_a$ or —$N_bR_c$;

$R_a$ is independently selected from H, —$NH_2$, —$NHC_{1-6}$ alkyl, —$N(C_{1-6}$ alkyl$)_2$, $C_{1-6}$ alkyl or $C_{1-6}$ haloalkyl;

$R_b$ and $R_c$ are independently selected from H, —$C_{0-6}$ alkylene-$S(O)_mR'$, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl or —$C_{0-6}$ alkylene-3- to 7-membered heterocyclyl; or, $R_b$, $R_c$ and N atom are taken together to form 3- to 7-membered heterocyclyl;

R' is independently selected from H, $C_{1-6}$ alkyl, $C_{2-6}$ alkenyl, $C_{2-6}$ alkynyl or $C_{1-6}$ haloalkyl;

m represents 0, 1, or 2.

8. The compound of formula (I-5) or (I-5-1) according to claim 6, or a pharmaceutically acceptable salt, an enantiomer, a diastereomer, and a racemate thereof, wherein, ⎓ indicates a single bond or a double bond;

$R_1$ is selected from H or D;

$R_2$ is selected from H or D;

$R_3$ is selected from —$NR_bR_c$, —O—$C_{1-6}$ alkylene-$R_8$, piperazinyl or morpholinyl, the said group is optionally substituted with 1 $R_8$ group;

L is selected from a chemical bond or —C(O)—;

$R_4$ is selected from $C_{1-6}$ alkyl or $C_{1-6}$ haloalkyl;

$R_5$ is selected from H, D, F or OMe;

$R_6$ is selected from H, D or F;

$R_7$ is selected from H, D or F;

$R_8$ is independently selected from H, D, —$NH_2$, —$NHC_{1-6}$ alkyl, —$N(C_{1-6}$ alkyl$)_2$, $C_{1-6}$ alkyl or $C_{1-6}$ haloalkyl;

$R_8$ is optionally substituted with 1, 2 or 3 R groups, wherein the R is independently selected from H, —OH, halogen, —$NO_2$, carbonyl, —CN, —$OR_a$, —$SR_a$ or —$NR_bR_c$;

$R_a$ is independently selected from H, $C_{1-6}$ alkyl or $C_{1-6}$ haloalkyl;

$R_b$ and $R_c$ are independently selected from H, —$C_{0-6}$ alkylene-$S(O)_mR'$, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl or —$C_{0-6}$ alkylene-3- to 7-membered heterocyclyl; or, $R_b$, $R_c$ and N atom are taken together to form 3- to 7-membered heterocyclyl;

R' is independently selected from H, $C_{1-6}$ alkyl, $C_{2-6}$ alkenyl, $C_{2-6}$ alkynyl or $C_{1-6}$ haloalkyl;

m represents 0, 1, or 2.

9. The compound according to claim 1, or a pharmaceutically acceptable salt, an enantiomer, a diastereomer, and a racemate thereof, which is a compound of general formula (I-6) or (I-6-1):

(I-6)

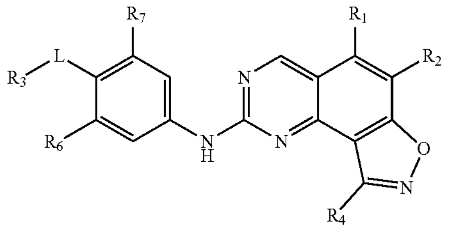

or (I-6-1)

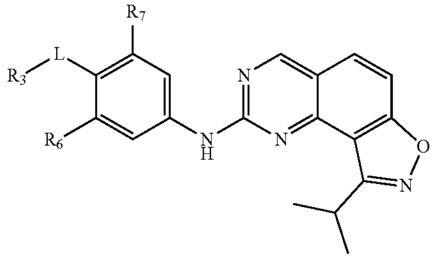

wherein,

⎓ indicates a single bond or a double bond;

$R_1$ is selected from H, D, halogen, —CN, —$OR_a$, $C_{1-6}$ alkyl or $C_{1-6}$ haloalkyl;

$R_2$ is selected from H, D, halogen, —CN, —$OR_a$, $C_{1-6}$ alkyl or $C_{1-6}$ haloalkyl;

$R_3$ is —$NR_bR_c$, —O—$C_{1-6}$ alkylene-$R_8$ or 4- to 7-membered heterocyclyl optionally substituted by 1, 2 or 3 $R_8$ groups;

L is selected from a chemical bond, —C(O)—, —C(O)NH— or —NHC(O)—;

$R_4$ is selected from $C_{1-6}$ alkyl, $C_{1-6}$ haloalkyl, $C_{3-7}$ cycloalkyl or 3- to 7-membered heterocyclyl;

$R_6$ is selected from H, D, halogen, —$S(O)_mR_a$, —$S(O)_mOR_a$ or —$S(O)_mNR_bR_c$;

$R_7$ is selected from H, D, halogen, —$S(O)_mR_a$, —$S(O)_mOR_a$ or —$S(O)_mNR_bR_c$;

$R_8$ is independently selected from H, D, —$NH_2$, —$NHC_{1-6}$ alkyl, —$N(C_{1-6}$ alkyl$)_2$, $C_{1-6}$ alkyl or $C_{1-6}$ haloalkyl;

$R_a$ is independently selected from H, —$NH_2$, —$NHC_{1-6}$ alkyl, —$N(C_{1-6}$ alkyl$)_2$, $C_{1-6}$ alkyl or $C_{1-6}$ haloalkyl;

$R_b$ and $R_c$ are independently selected from H, —$C_{0-6}$ alkylene-$S(O)_mR'$, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl or —$C_{0-6}$ alkylene-3- to 7-membered heterocyclyl; or, $R_b$, $R_c$ and N atom are taken together to form 3- to 7-membered heterocyclyl;

R' is independently selected from H, $C_{1-6}$ alkyl, $C_{2-6}$ alkenyl, $C_{2-6}$ alkynyl or $C_{1-6}$ haloalkyl;

m represents 0, 1, or 2.

10. The compound of formula (I-6) or (I-6-1) according to claim 9, or a pharmaceutically acceptable salt, an enantiomer, a diastereomer, and a racemate, thereof, wherein, ⎓ indicates a single bond or a double bond;

$R_1$ is selected from H, D, halogen, —CN or —$OR_a$;

$R_2$ is selected from H, D, halogen, —CN or —$OR_a$;

$R_3$ is —O—$C_{1-6}$ alkylene-$R_8$ or 5- to 6-membered heterocyclyl optionally substituted by 1 or 2 $R_8$ groups;

L is selected from a chemical bond, —C(O)—, —C(O)NH— or —NHC(O)—;

$R_4$ is selected from $C_{1-6}$ alkyl, $C_{1-6}$ haloalkyl, $C_{3-7}$ cycloalkyl or 3- to 7-membered heterocyclyl;

$R_6$ is selected from H, D or halogen;

$R_7$ is selected from H, D or halogen;

$R_8$ is independently selected from H, D, —$NH_2$, —$NHC_{1-6}$ alkyl, —$N(C_{1-6}$ alkyl$)_2$, $C_{1-6}$ alkyl or $C_{1-6}$ haloalkyl;

$R_a$ is independently selected from H, $C_{1-6}$ alkyl or $C_{1-6}$ haloalkyl.

11. The compound of formula (I-6) or (I-6-1) according to claim 9, or a pharmaceutically acceptable salt, an enantiomer, a diastereomer, and a racemate, thereof, wherein, ⎓ indicates a single bond or a double bond;

$R_1$ is selected from H or D;

$R_2$ is selected from H or D;

$R_3$ is selected from —O—$C_{1-6}$ alkylene-$R_8$, piperazinyl or morpholinyl, the said group is optionally substituted with 1 $R_8$ group;

L is selected from a chemical bond or —C(O)—;

$R_4$ is selected from $C_{1-6}$ alkyl or $C_{1-6}$ haloalkyl;

$R_6$ is selected from H, D or F;

$R_7$ is selected from H, D or F;

$R_8$ is independently selected from H, D, —$NH_2$, —$NHC_{1-6}$ alkyl, —$N(C_{1-6}$ alkyl$)_2$, $C_{1-6}$ alkyl or $C_{1-6}$ haloalkyl.

12. The compound according to claim 1, or a pharmaceutically acceptable salt, an enantiomer, a diastereomer, and a racemate thereof, which is a compound of general formula (I-7) or (I-7-1):

(I-7)

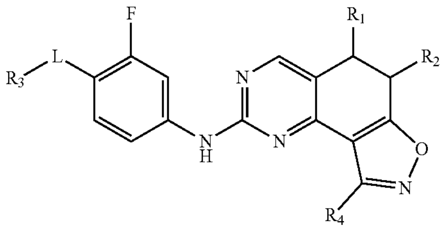

or

-continued (I-7-1)

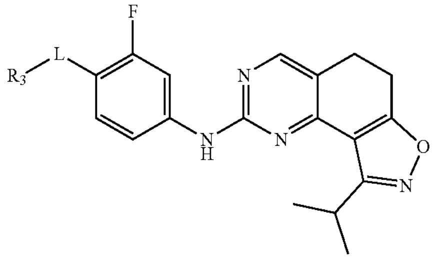

wherein, $R_1$ is selected from H, D, halogen, —CN, —$OR_a$, $C_{1-6}$ alkyl or $C_{1-6}$ haloalkyl;

$R_2$ is selected from H, D, halogen, —CN, —$OR_a$, $C_{1-6}$ alkyl or $C_{1-6}$ haloalkyl;

$R_3$ is 5- to 6-membered heterocyclyl optionally substituted with 1, 2 or 3 $R_8$ groups;

L is selected from a chemical bond, —C(O)—, —C(O)NH— or —NHC(O)—;

$R_4$ is selected from $C_{1-6}$ alkyl, $C_{1-6}$ haloalkyl, $C_{3-7}$ cycloalkyl or 3- to 7-membered heterocyclyl;

$R_8$ is independently selected from H, D, —$NH_2$, —$NHC_{1-6}$ alkyl, —$N(C_{1-6}$ alkyl$)_2$, $C_{1-6}$ alkyl or $C_{1-6}$ haloalkyl;

$R_a$ is independently selected from H, $C_{1-6}$ alkyl or $C_{1-6}$ haloalkyl.

13. The compound of formula (I-7) or (I-7-1) according to claim 12, or a pharmaceutically acceptable salt, an enantiomer, a diastereomer, and a racemate, thereof, wherein, $R_1$ is selected from H, D, halogen, —CN or —$OR_a$;

$R_2$ is selected from H, D, halogen, —CN or —$OR_a$;

$R_3$ is 5- to 6-membered heterocyclyl optionally substituted with 1 or 2 $R_8$ groups;

L is selected from a chemical bond, —C(O)—, —C(O)NH— or —NHC(O)—;

$R_4$ is selected from $C_{1-6}$ alkyl, $C_{1-6}$ haloalkyl, $C_{3-7}$ cycloalkyl or 3- to 7-membered heterocyclyl;

$R_8$ is independently selected from H, D, $C_{1-6}$ alkyl or $C_{1-6}$ haloalkyl;

$R_a$ is independently selected from H, $C_{1-6}$ alkyl or $C_{1-6}$ haloalkyl.

14. The compound of formula (I-7) or (I-7-1) according to claim 12, or a pharmaceutically acceptable salt, an enantiomer, a diastereomer, and a racemate, thereof, wherein, $R_1$ is selected from H or D;

$R_2$ is selected from H or D;

$R_3$ is piperazinyl or morpholinyl optionally substituted with one $R_8$ group;

L is selected from a chemical bond or —C(O)—;

$R_4$ is selected from $C_{1-6}$ alkyl or $C_{1-6}$ haloalkyl;

$R_8$ is selected from H, D, $C_{1-6}$ alkyl or $C_{1-6}$ haloalkyl.

15. The compound according to claim 1, or a pharmaceutically acceptable salt, an enantiomer, a diastereomer, and a racemate thereof, which is a compound of general formula (I-8) or (I-8-1):

(I-8)

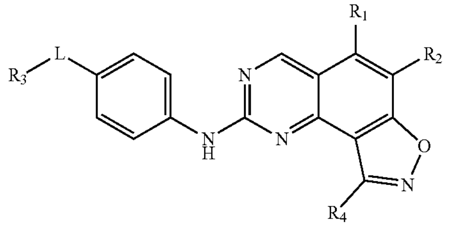

or (I-8-1)

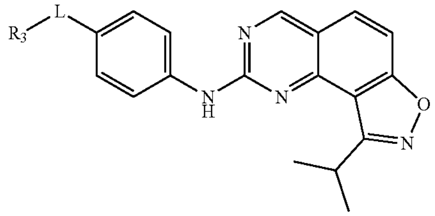

wherein, $R_1$ is selected from H, D, halogen, —CN, —$OR_a$, $C_{1-6}$ alkyl or $C_{1-6}$ haloalkyl;

$R_2$ is selected from H, D, halogen, —CN, —$OR_a$, $C_{1-6}$ alkyl or $C_{1-6}$ haloalkyl;

$R_3$ is 5- to 6-membered heterocyclyl optionally substituted with 1, 2 or 3 $R_8$ groups;

L is selected from a chemical bond, —C(O)—, —C(O)NH— or —NHC(O)—;

$R_4$ is selected from $C_{1-6}$ alkyl, $C_{1-6}$ haloalkyl, $C_{3-7}$ cycloalkyl or 3- to 7-membered heterocyclyl;

$R_8$ is independently selected from H, D, —$NH_2$, —$NHC_{1-6}$ alkyl, —$N(C_{1-6}$ alkyl$)_2$, $C_{1-6}$ alkyl or $C_{1-6}$ haloalkyl;

$R_a$ is independently selected from H, $C_{1-6}$ alkyl or $C_{1-6}$ haloalkyl.

16. The compound of formula (I-8) or (I-8-1) according to claim 15, or a pharmaceutically acceptable salt, an enantiomer, a diastereomer, and a racemate, thereof, wherein, $R_1$ is selected from H, D, halogen, —CN or —$OR_a$;

$R_2$ is selected from H, D, halogen, —CN or —$OR_a$;

$R_3$ is 5- to 6-membered heterocyclyl optionally substituted with 1 or 2 $R_8$ groups;

L is selected from a chemical bond, —C(O)—, —C(O)NH— or —NHC(O)—;

$R_4$ is selected from $C_{1-6}$ alkyl, $C_{1-6}$ haloalkyl, $C_{3-7}$ cycloalkyl or 3- to 7-membered heterocyclyl;

$R_8$ is independently selected from H, D, $C_{1-6}$ alkyl or $C_{1-6}$ haloalkyl;

$R_a$ is independently selected from H, $C_{1-6}$ alkyl or $C_{1-6}$ haloalkyl.

17. The compound of formula (I-8) or (I-8-1) according to claim 15, or a pharmaceutically acceptable salt, an enantiomer, a diastereomer, and a racemate, thereof, wherein, $R_1$ is selected from H or D;

$R_2$ is selected from H or D;

$R_3$ is piperazinyl or morpholinyl optionally substituted with one $R_8$ group;

L is selected from a chemical bond or —C(O)—;

$R_4$ is selected from $C_{1-6}$ alkyl or $C_{1-6}$ haloalkyl;

$R_8$ is selected from H, D, $C_{1-6}$ alkyl or $C_{1-6}$ haloalkyl.

18. The compound according to claim 1, or a pharmaceutically acceptable salt, an enantiomer, a diastereomer, and a racemate thereof, which is a compound of general formula (I-9) or (I-9-1):

(I-9)

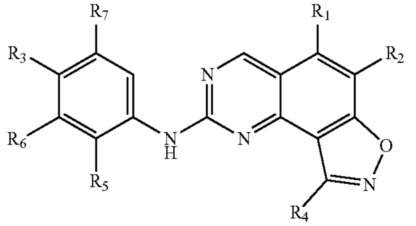

or (I-9-1)

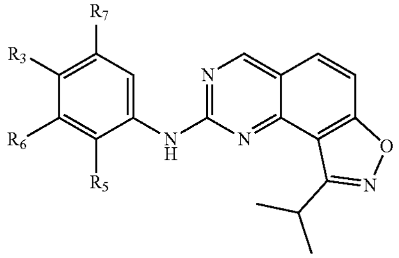

wherein,

⎓ indicates a single bond or a double bond;

$R_1$ is selected from H, D, halogen, —CN, —$OR_a$, —$SR_a$, —$NR_bR_c$, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_6$-10 aryl, or 5- to 10-membered heteroaryl; wherein the said $C_{3-7}$ cycloalkyl or 3- to 7-membered heterocyclyl is optionally substituted by oxo or thioxo;

$R_2$ is selected from H, D, halogen, —CN, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl; wherein the said $C_{3-7}$ cycloalkyl or 3- to 7-membered heterocyclyl is optionally substituted by oxo or thioxo;

$R_3$ is selected from H, D, halogen, —CN, —$NO_2$, —$OR_a$, —$SR_a$, —$NR_bR_c$, —C(O)$R_a$, —C(O)$OR_a$, —C(O)$NR_bR_c$, —$S(O)_mR_a$, —$S(O)_mOR_a$, —$S(O)_mNR_bR_c$, —O—$C_{1-6}$ alkylene-$R_8$, $C_{1-6}$ alkyl, $C_{1-6}$ haloalkyl, $C_{3-7}$ cycloalkyl, 3- to 11-membered heterocyclyl, $C_{6-10}$ aryl, or 5- to 10-membered heteroaryl, each of which is optionally substituted by 1, 2, 3, 4, or 5 $R_8$ groups;

$R_4$ is selected from H, D, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl, or 5- to 10-membered heteroaryl;

$R_5$ is selected from H, D, halogen, —CN, —$OR_a$, —$SR_a$, —$NR_bR_c$, —C(O)$R_a$, —C(O)$OR_a$, —C(O)$NR_bR_c$, —$S(O)_mR_a$, —$S(O)_mOR_a$, —$S(O)_mNR_bR_c$, $C_{1-6}$ alkyl or $C_{1-6}$ haloalkyl;

$R_6$ is selected from H, D, halogen, —CN, —$OR_a$, —$SR_a$, —$NR_bR_c$, —C(O)$R_a$, —C(O)$OR_a$, —C(O)$NR_bR_c$, —$S(O)_mR_a$, —$S(O)_mOR_a$, —$S(O)_mNR_bR_c$, $C_{1-6}$ alkyl or $C_{1-6}$ haloalkyl;

$R_7$ is selected from H, D, halogen, —CN, —$OR_a$, —$SR_a$, —$NR_bR_c$, —C(O)$R_a$, —C(O)$OR_a$, —C(O)$NR_bR_c$, —$S(O)_mR_a$, —$S(O)_mOR_a$, —$S(O)_mNR_bR_c$, $C_{1-6}$ alkyl or $C_{1-6}$ haloalkyl;

$R_8$ is selected from H, D, —$NH_2$, —$NHC_{1-6}$ alkyl, —$N(C_{1-6}$ alkyl$)_2$, $C_{1-6}$ alkyl, $C_{1-6}$ haloalkyl, —$C_{0-6}$ alkylene-$OR_a$, $C_{3-7}$ cycloalkyl, 3- to 7-membered heterocyclyl, $C_{6-10}$ aryl, or 5- to 10-membered heteroaryl; or two $R_8$ on the same atom are taken together to form oxo or thioxo;

$R_a$ is independently selected from H, —$C_{0-6}$ alkylene-CN, —$C_{0-6}$ alkylene-$NO_2$, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C(O)OR', —$C_{0-6}$ alkylene-C(O)NR"R'", —$C_{0-6}$ alkylene-$S(O)_m$R', —$C_{0-6}$ alkylene-$S(O)_m$OR', —$C_{0-6}$ alkylene-$S(O)_m$NR"R'", $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl;

$R_b$ and $R_c$ are independently selected from H, —$C_{0-6}$ alkylene-CN, —$C_{0-6}$ alkylene-$NO_2$, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C(O)OR', —$C_{0-6}$ alkylene-C(O)NR"R'", —$C_{0-6}$ alkylene-$S(O)_m$R', —$C_{0-6}$ alkylene-$S(O)_m$OR', —$C_{0-6}$ alkylene-$S(O)_m$NR"R'", $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or, $R_b$, $R_c$ and N atom are taken together to form 3- to 7-membered heterocyclyl;

R' is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl;

R" and R'" are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl; or, R", R'" and N atom are taken together to form 3- to 7-membered heterocyclyl;

m represents 0, 1, or 2.

19. The compound of formula (I-9) or (I-9-1) according to claim 18, or a pharmaceutically acceptable salt, an enantiomer, a diastereomer, and a racemate, thereof, wherein, ⎓ indicates a single bond or a double bond;

$R_1$ is selected from H, D, halogen, —CN, —$OR_a$, —$SR_a$, —$NR_bR_c$, $C_{1-6}$ alkyl or $C_{1-6}$ haloalkyl;

$R_2$ is selected from H, D, halogen, —CN, —$OR_a$, —$SR_a$, —$NR_bR_c$, $C_{1-6}$ alkyl or $C_{1-6}$ haloalkyl;

$R_3$ is selected from H, D, halogen, —CN, —$NO_2$, —$OR_a$, —$SR_a$, —$NR_bR_c$, —C(O)$R_a$, —C(O)$OR_a$, —C(O)$NR_bR_c$, —$S(O)_mR_a$, —$S(O)_mOR_a$, —$S(O)_mNR_bR_c$, $C_{1-6}$ alkyl, $C_{1-6}$ haloalkyl, $C_{3-7}$ cycloalkyl or 4- to 7-membered heterocyclyl, the said group is optionally substituted with 1, 2 or 3 $R_8$ groups;

$R_4$ is selected from H, D, $C_{1-6}$ alkyl, $C_{1-6}$ haloalkyl, $C_{3-7}$ cycloalkyl or 3- to 7-membered heterocyclyl;

$R_5$ is selected from H, D, halogen, —CN, —$OR_a$, —$SR_a$, —$NR_bR_c$, $C_{1-6}$ alkyl or $C_{1-6}$ haloalkyl;

$R_6$ is selected from H, D, halogen, —CN, —$OR_a$, —$SR_a$, —$NR_bR_c$, —C(O)$R_a$, —C(O)$OR_a$, —C(O)$NR_bR_c$, —$S(O)_mR_a$, —$S(O)_mOR_a$, —$S(O)_mNR_bR_c$, $C_{1-6}$ alkyl or $C_{1-6}$ haloalkyl;

$R_7$ is selected from H, D, halogen, —CN, —$OR_a$, —$SR_a$, —$NR_bR_c$, —C(O)$R_a$, —C(O)$OR_a$, —C(O)$NR_bR_c$, —$S(O)_mR_a$, —$S(O)_mOR_a$, —$S(O)_mNR_bR_c$, $C_{1-6}$ alkyl or $C_{1-6}$ haloalkyl;

$R_8$ is selected from H, D, —$NH_2$, —$NHC_{1-6}$ alkyl, —N($C_{1-6}$ alkyl)$_2$, $C_{1-6}$ alkyl or $C_{1-6}$ haloalkyl; or two $R_8$ on the same atom are taken together to form oxo or thioxo;

$R_a$ is independently selected from H, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C(O)OR', —$C_{0-6}$ alkylene-C(O)NR"R'", —$C_{0-6}$ alkylene-$S(O)_m$R', —$C_{0-6}$ alkylene-$S(O)_m$OR', —$C_{0-6}$ alkylene-$S(O)_m$NR"R'", $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl or —$C_{0-6}$ alkylene-3- to 7-membered heterocyclyl;

$R_b$ and $R_c$ are independently selected from H, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C(O)OR', —$C_{0-6}$ alkylene-C(O)NR"R'", —$C_{0-6}$ alkylene-$S(O)_m$R', —$C_{0-6}$ alkylene-$S(O)_m$OR', —$C_{0-6}$ alkylene-$S(O)_m$NR"R'", $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl or —$C_{0-6}$ alkylene-3- to 7-membered heterocyclyl; or, $R_b$, $R_c$ and N atom are taken together to form 3- to 7-membered heterocyclyl;

R' is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl;

R" and R'" are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl; or, R", R'" and N atom are taken together to form 3- to 7-membered heterocyclyl;

m represents 0, 1, or 2.

20. The compound of formula (I-9) or (I-9-1) according to claim 18, or a pharmaceutically acceptable salt, an enantiomer, a diastereomer, and a racemate, thereof, wherein, ⎓ indicates a single bond or a double bond;

$R_1$ is selected from H, D, halogen, —CN, —$OR_a$, $C_{1-6}$ alkyl or $C_{1-6}$ haloalkyl;

$R_2$ is selected from H, D, halogen, —CN, —$OR_a$, $C_{1-6}$ alkyl or $C_{1-6}$ haloalkyl;

$R_3$ is selected from H, D, halogen, —CN, —$NO_2$, —$OR_a$, —$SR_a$, —$NR_bR_c$, —C(O)$R_a$, —C(O)$OR_a$, —C(O)$NR_bR_c$, —$S(O)_mR_a$, —$S(O)_mOR_a$, —$S(O)_mNR_bR_c$, $C_{3-7}$ cycloalkyl or 4- to 7-membered heterocyclyl, the said group is optionally substituted with 1 or 2 $R_8$ groups;

$R_4$ is selected from $C_{1-6}$ alkyl, $C_{1-6}$ haloalkyl, $C_{3-7}$ cycloalkyl or 3- to 7-membered heterocyclyl;

$R_5$ is selected from H, D, halogen, —CN, —$OR_a$, —$SR_a$, —$NR_bR_c$, $C_{1-6}$ alkyl or $C_{1-6}$ haloalkyl;

$R_6$ is selected from H, D, halogen, —CN, —$OR_a$, —$SR_a$, —$NR_bR_c$, —C(O)$R_a$, —C(O)$OR_a$, —C(O)$NR_bR_c$, —$S(O)_mR_a$, —$S(O)_mOR_a$, —$S(O)_mNR_bR_c$, $C_{1-6}$ alkyl or $C_{1-6}$ haloalkyl;

$R_7$ is selected from H, D, halogen, —CN, —$OR_a$, —$SR_a$, —$NR_bR_c$, —C(O)$R_a$, —C(O)$OR_a$, —C(O)$NR_bR_c$, —$S(O)_mR_a$, —$S(O)_mOR_a$, —$S(O)_mNR_bR_c$, $C_{1-6}$ alkyl or $C_{1-6}$ haloalkyl;

$R_8$ is selected from H, D, $C_{1-6}$ alkyl or $C_{1-6}$ haloalkyl;

$R_a$ is independently selected from H, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C(O)OR', —$C_{0-6}$ alkylene-C(O)NR"R'", —$C_{0-6}$ alkylene-$S(O)_m$R', —$C_{0-6}$ alkylene-$S(O)_m$OR', —$C_{0-6}$ alkylene-$S(O)_m$NR"R'", $C_{1-6}$ alkyl, $C_{1-6}$ haloalkyl, —$C_{0-6}$ alkylene-$C_{3-7}$ cycloalkyl or —$C_{0-6}$ alkylene-3- to 7-membered heterocyclyl;

$R_b$ and $R_c$ are independently selected from H, —$C_{0-6}$ alkylene-OR', —$C_{0-6}$ alkylene-SR', —$C_{0-6}$ alkylene-NR"R'", —$C_{0-6}$ alkylene-C(O)R', —$C_{0-6}$ alkylene-C(O)OR', —$C_{0-6}$ alkylene-C(O)NR"R'", —$C_{0-6}$ alkylene-$S(O)_mR'$, —$C_{0-6}$ alkylene-$S(O)_mOR'$, —$C_{0-6}$ alkylene-$S(O)_mNR''R'''$, $C_{1-6}$ alkyl, $C_{1-6}$ haloalkyl, —$C_{0-6}$ alkylene-$C_{3-7}$ cycloalkyl or —$C_{0-6}$ alkylene-3- to 7-membered heterocyclyl; or, $R_b$, $R_c$ and N atom are taken together to form 3- to 7-membered heterocyclyl;

R' is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl;

R'' and R''' are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl; or, R'', R''' and N atom are taken together to form 3- to 7-membered heterocyclyl;

m represents 0, 1, or 2.

21. The compound of formula (I-9) or (I-9-1) according to claim 18, or a pharmaceutically acceptable salt, an enantiomer, a diastereomer, and a racemate, thereof, wherein, $\overset{\text{---}}{=}$ indicates a single bond or a double bond;

$R_1$ is selected from H or D;

$R_2$ is selected from H or D;

$R_3$ is selected from H, D, —$OR_a$, —$NR_bR_c$, —$C(O)R_a$, —$C(O)OR_a$, —$C(O)NR_bR_c$, —$S(O)_mR_a$, —$S(O)_mOR_a$, —$S(O)_mNR_bR_c$, $C_4$-6 cycloalkyl or 5- to 6-membered heterocyclyl, the said group is optionally substituted with 1 $R_8$ group;

$R_4$ is selected from $C_{1-6}$ alkyl, $C_{1-6}$ haloalkyl, $C_{3-7}$ cycloalkyl or 3- to 7-membered heterocyclyl;

$R_5$ is selected from H, D, halogen, —$OR_a$, —$SR_a$ or —$NR_bR_c$;

$R_6$ is selected from H, D, halogen, —$C(O)R_a$, —$C(O)OR_a$, —$C(O)NR_bR_c$, —$S(O)_mR_a$, —$S(O)_mOR_a$ or —$S(O)_mNR_bR_c$;

$R_7$ is selected from H, D, halogen, —$C(O)R_a$, —$C(O)OR_a$, —$C(O)NR_bR_c$, —$S(O)_mR_a$, —$S(O)_mOR_a$ or —$S(O)_mNR_bR_c$;

$R_8$ is selected from H, D, $C_{1-6}$ alkyl or $C_{1-6}$ haloalkyl;

$R_a$ is independently selected from H, —$C_{0-6}$ alkylene-OR', —$C_{0-6}$ alkylene-NR''R''', —$C_{0-6}$ alkylene-C(O)R', —$C_{0-6}$ alkylene-$S(O)_mR'$, $C_{1-6}$ alkyl, $C_{1-6}$ haloalkyl, —$C_{0-6}$ alkylene-$C_{3-7}$ cycloalkyl or —$C_{0-6}$ alkylene-3- to 7-membered heterocyclyl;

$R_b$ and $R_c$ are independently selected from H, —$C_{0-6}$ alkylene-OR', —$C_{0-6}$ alkylene-NR''R''', —$C_{0-6}$ alkylene-C(O)R', —$C_{0-6}$ alkylene-$S(O)_mR'$, $C_{1-6}$ alkyl, $C_{1-6}$ haloalkyl, —$C_{0-6}$ alkylene-$C_{3-7}$ cycloalkyl or —$C_{0-6}$ alkylene-3- to 7-membered heterocyclyl; or, $R_b$, $R_c$ and N atom are taken together to form 5- to 6-membered heterocyclyl;

R' is independently selected from H, $C_{1-6}$ alkyl or $C_{1-6}$ haloalkyl;

R'' and R''' are independently selected from H, $C_{1-6}$ alkyl or $C_{1-6}$ haloalkyl; or, R'', R''' and N atom are taken together to form 5- to 6-membered heterocyclyl;

m represents 0, 1, or 2.

22. A compound, or a pharmaceutically acceptable salt, an enantiomer, a diastereomer, and a racemate thereof, wherein the said compound is selected from the group consisting of:

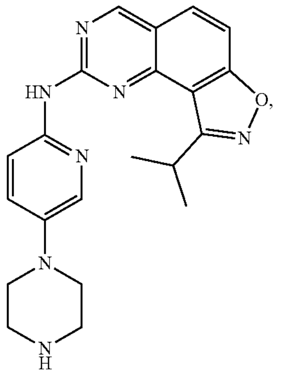
,

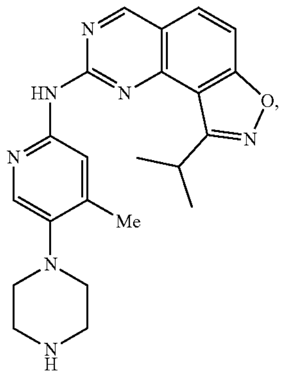
,

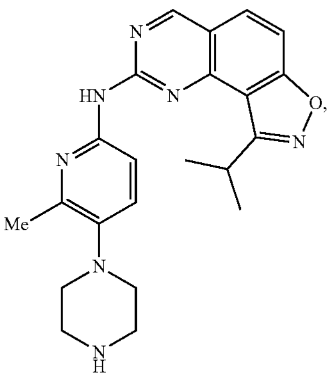
,

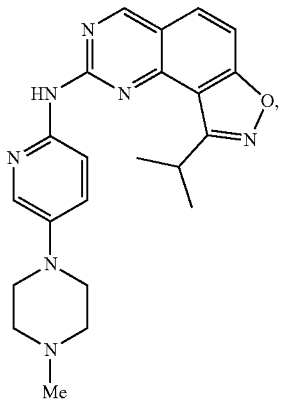

-continued
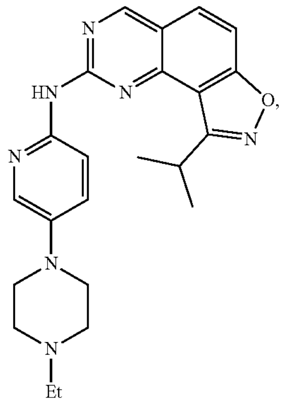
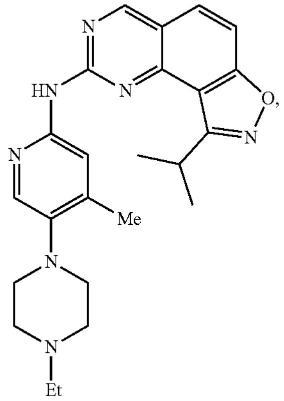
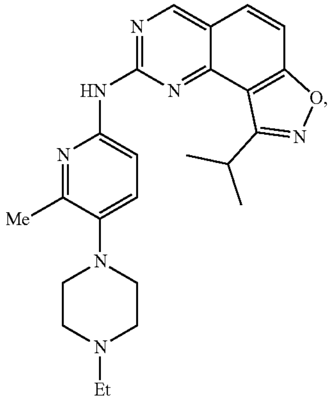
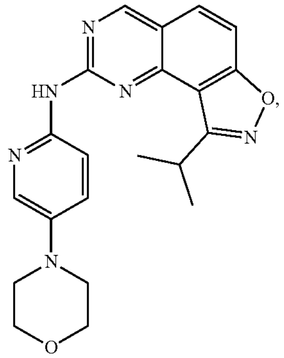
-continued
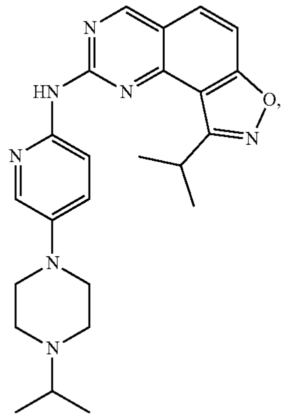
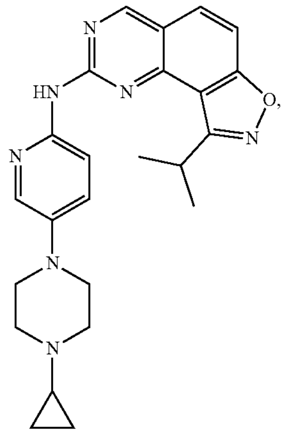
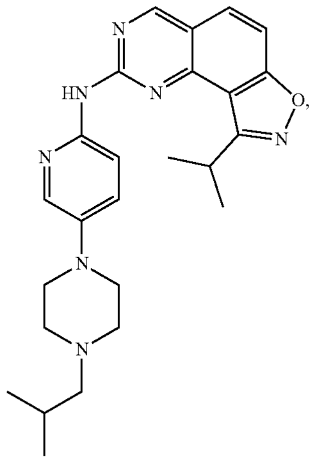
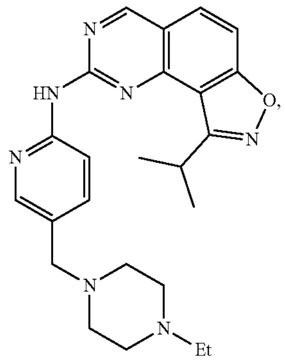

-continued
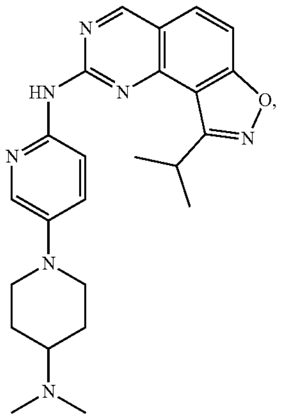
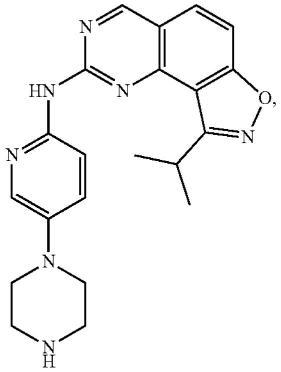
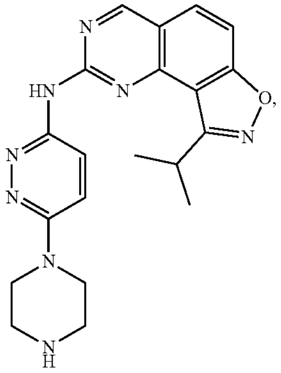
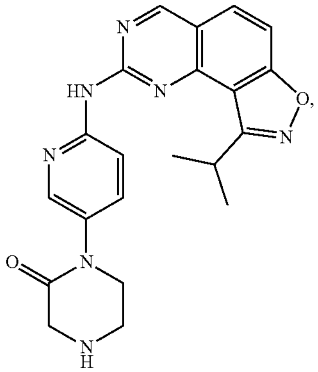
-continued
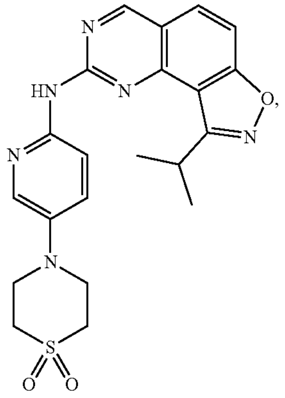
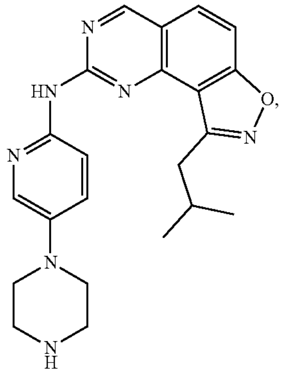
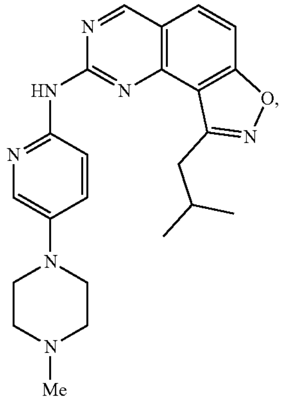
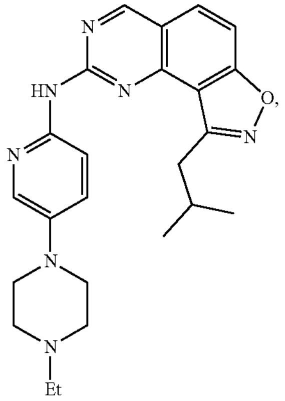

-continued
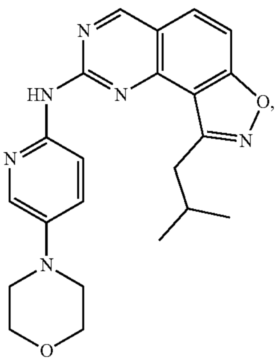
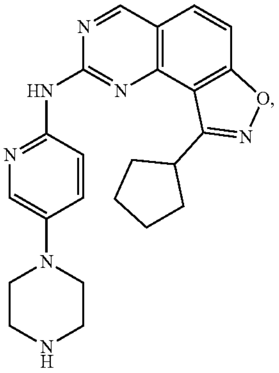
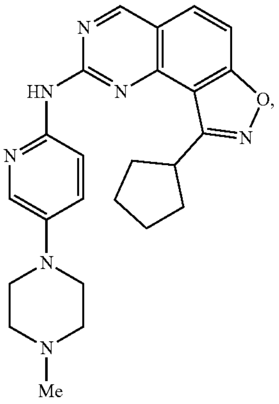
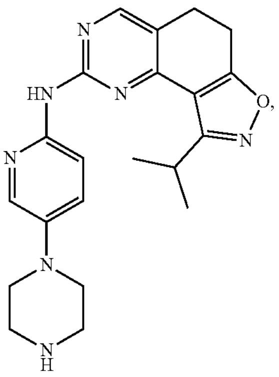
-continued
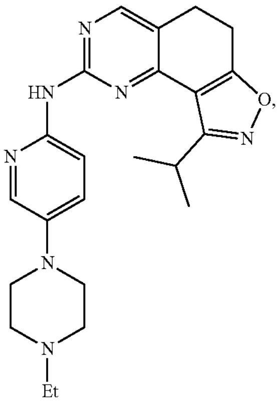
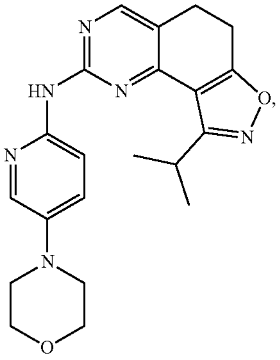
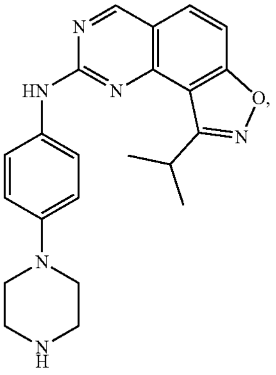
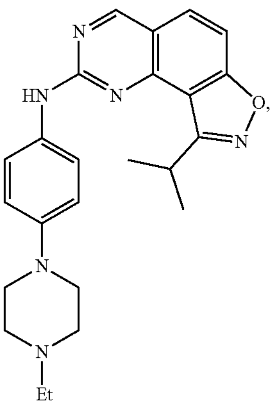

-continued
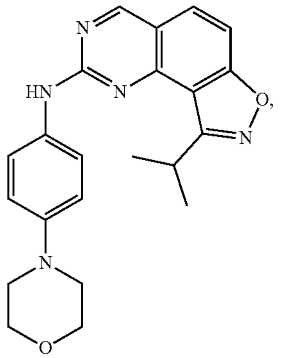
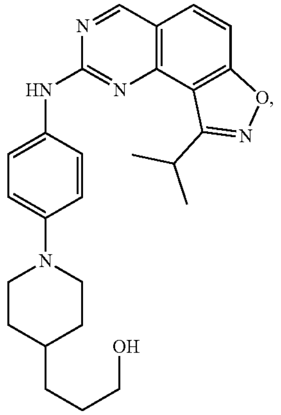
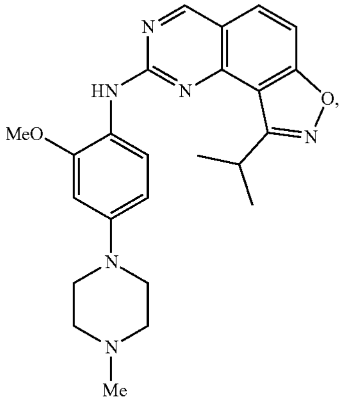
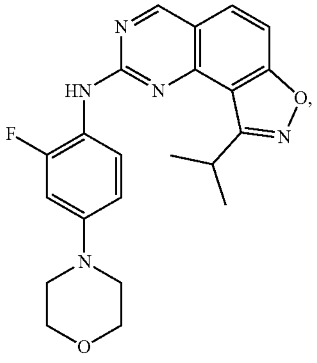
-continued
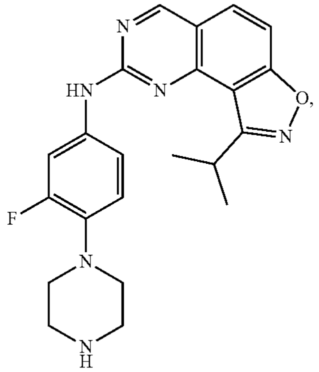
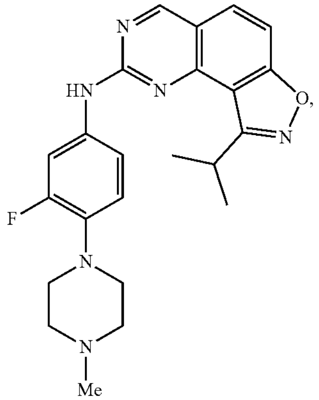
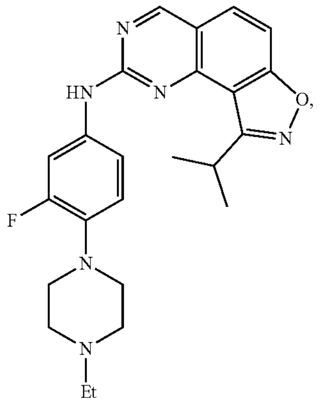
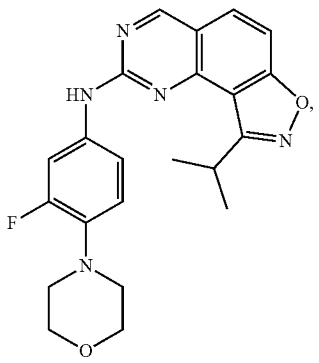

-continued
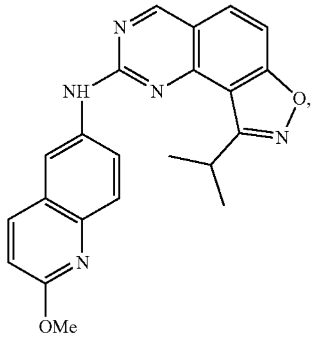
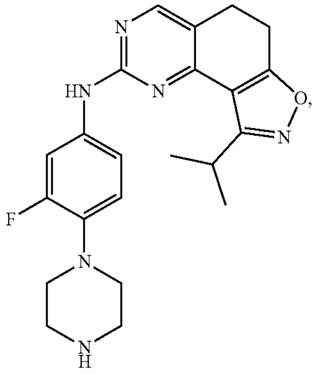
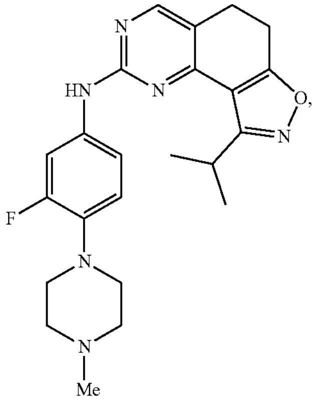
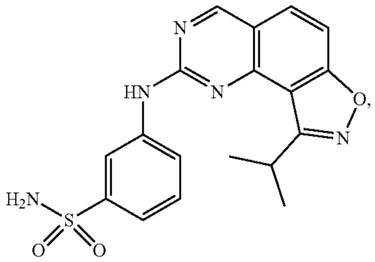
-continued
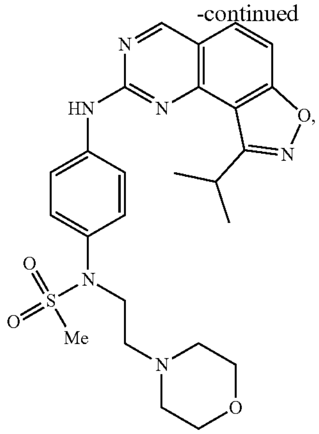
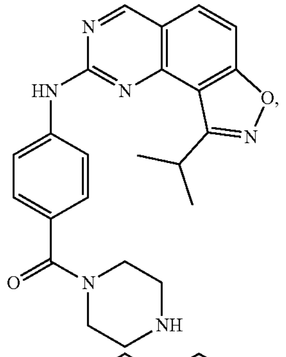
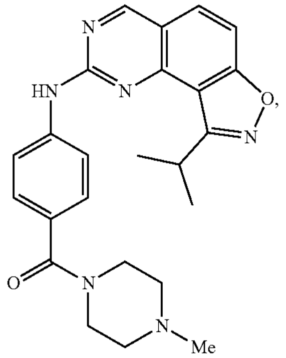
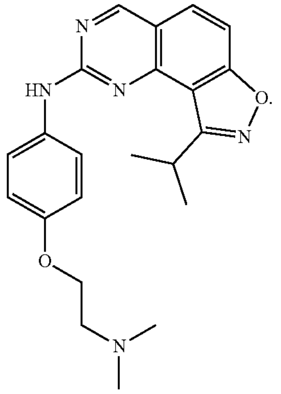
23. A pharmaceutical composition, comprising a compound according to claim 1, or a pharmaceutically acceptable salt, an enantiomer, a diastereomer, and a racemate thereof, and pharmaceutically acceptable excipient(s).
* * * * *